US009493518B2

(12) United States Patent
Chong et al.

(10) Patent No.: US 9,493,518 B2
(45) Date of Patent: Nov. 15, 2016

(54) COMPOSITIONS AND METHODS FOR TREATING CLOSTRIDIUM DIFFICILE-ASSOCIATED DISEASES

(71) Applicant: National Health Research Institutes, Miaoli County (TW)

(72) Inventors: Pele Choi-Sing Chong, Miaoli County (TW); Jui-Hsin Huang, Miaoli County (TW); Chih-Hsiang Leng, Miaoli County (TW)

(73) Assignee: National Health Research Institutes, Zhunan Town (TW)

( * ) Notice: Subject to any disclaimer, the term of this patent is extended or adjusted under 35 U.S.C. 154(b) by 0 days.

(21) Appl. No.: 14/209,987

(22) Filed: Mar. 13, 2014

(65) Prior Publication Data

US 2014/0271700 A1 Sep. 18, 2014

Related U.S. Application Data

(60) Provisional application No. 61/782,390, filed on Mar. 14, 2013.

(51) Int. Cl.

*A61K 39/39* (2006.01)
*C07K 14/33* (2006.01)
*A61K 38/48* (2006.01)

(Continued)

(52) U.S. Cl.

CPC ............... *C07K 14/33* (2013.01); *A61K 39/08* (2013.01); *A61K 39/39* (2013.01); *G01N 33/56911* (2013.01); *A61K 2039/543* (2013.01); *A61K 2039/55544* (2013.01); *A61K 2039/55566* (2013.01); *C07K 2319/40* (2013.01); *C12N 2799/026* (2013.01); *G01N 2333/33* (2013.01)

(58) Field of Classification Search

CPC ....................................................... A61K 39/08
USPC ....................................................... 424/247.1
See application file for complete search history.

(56) References Cited

U.S. PATENT DOCUMENTS 7,811,584 B2 * 10/2010 Steward ............ A61K 38/4886 424/184.1
8,206,940 B2 * 6/2012 Feng .................. G01N 33/5014 424/167.1

(Continued)

FOREIGN PATENT DOCUMENTS

WO 98/59053 * 12/1998 ............ C12N 15/31
WO WO-2008/152429 12/2008

(Continued)

OTHER PUBLICATIONS

Demarest, Stephen J. et al, Journal of Molecular Biology, vol. 346, pp. 1197-1206, 2005, Structural Characterization of the Cell Wall Binding Domains of Clostridium difficile toxins A and B; Evidence that Ca2+ Plays a Role in Toxin A Cell Surface Association.*

(Continued)

*Primary Examiner* — Albert Navarro
*Assistant Examiner* — Ginny Portner
(74) *Attorney, Agent, or Firm* — Cesari and McKenna LLP

(57) ABSTRACT

Described herein are isolated polypeptides each containing one or more receptor-binding sites of toxin A (tcdA) of *Clostridium difficile* (Cd), nucleic acids encoding the polypeptides, and methods of using the polypeptides and nucleic acids.

8 Claims, 23 Drawing Sheets

Consensus *tcdA*-RBD sequence (911 amino acids)

HMGFNSENELDRDHLGFKIIDNKTYYYDEDSKLVKGLININNSLFYFDPIESNLVTGWQTINGKKYYFDINTGAASTSYKIINGKHFYFNNNGVMQLGVFKGPDGFE
YFAPANTQNNNIEGQAIVYQSKFLTLNGKKYYFDNDSKAVTGWRIINNEKYYFNPNNAIAAVGLQVIDNNKYYFNPDTAIISKGWQTVNGSRYYFDTDTAIAFNGYK
TIDGKHFYFDSDCVVKIGVFSGSNGFEYFAPANTYNNNIEGQAIVYQSKFLTLNGKKYYFDNNSKAVTGWQTIDSKKYYFNTNTAEAATGWQTIDGKKYYFNTNTAE
AATGWQTIDGKKYYFNTNTSIASTGYTIINGKYFYFNTDGIMQIGVFKVPNGFEYFAPANTHNNNIEGQAILYQNKFLTLNGKKYYFGSDSKAITGWQTIDGKKYYF
NPNNAIAATHLCTINNDKYYFSYDGILQNGYITIERNNFYFDANNESKMVTGVFKGPNGFEYFAPANTHNNNIEGQAIVYQNKFLTLNGKKYYFDNDSKAVTGWQTI
DSKKYYFNLNTAVAVTGWQTIDGEKYYFNLNTAEAATGWQTIDGKRYYFNTNTYIASTGYTIINGKHFYFNTDGIMQIGVFKGPDGFEYFAPANTHNNNIEGQAILY
QNKFLTLNGKKYYFGSDSKAVTGLRTIDGKKYYFNTNTAVAVTGWQTINGKKYYFNTNTYIASTGYTIISGKHFYFNTDGIMQIGVFKGPDGFEYFAPANTDANNIE
GQAIRYQNRFLYLHDNIYYFGNDSKAATGWATIDGNRYYFEPNTAMGANGYKTIDNKNFYFRNGLPQIGVFKGPNGFEYFAPANTDANNIDGQAIRYQNRFLHLLGK
IYYFGNNSKAVTGWQTINSKVYYFMPDTAMAAAGGLFEIDGVIYFFGVDGVKAPGIYGLE

(51) Int. Cl.

| | |
|---|---|
| ***C12N 9/52*** | (2006.01) |
| ***G01N 33/569*** | (2006.01) |
| ***A61K 39/08*** | (2006.01) |
| *A61K 39/00* | (2006.01) |

(56) References Cited

U.S. PATENT DOCUMENTS

| | | | | |
|---|---|---|---|---|
| 8,658,767 B2 * | 2/2014 | Leng | C12P 21/02 424/188.1 |
| 8,748,151 B2 * | 6/2014 | Frevert | C07K 14/33 424/94.1 |
| 8,771,990 B2 * | 7/2014 | Leng | C12P 21/02 435/252.33 |
| 2009/0087478 A1 * | 4/2009 | Hansen et al. | 424/450 |
| 2009/0221499 A1 | 9/2009 | Chih-Hsiang et al. | |
| 2010/0310522 A1 * | 12/2010 | Gasson et al. | 424/93.6 |
| 2011/0053244 A1 * | 3/2011 | Oyler | C07K 14/33 435/188 |
| 2012/0121607 A1 * | 5/2012 | Shone et al. | 424/167.1 |
| 2012/0134972 A1 * | 5/2012 | Mayer et al. | 424/93.21 |
| 2012/0276132 A1 * | 11/2012 | Feng | A61K 39/08 424/192.1 |
| 2012/0282293 A1 * | 11/2012 | Galen | A61K 39/08 424/200.1 |
| 2013/0330371 A1 * | 12/2013 | Anderson et al. | 424/190.1 |

FOREIGN PATENT DOCUMENTS

| | | | | |
|---|---|---|---|---|
| WO | 2010/094970 | * | 8/2010 | A61K 39/40 |
| WO | 2011/060431 | * | 5/2011 | |
| WO | WO-2012/046061 | | 4/2012 | |

OTHER PUBLICATIONS

Ward, Stephen J. et al, Immunogenicity of a *Salmonella typhimurium* aroA aroD Vaccine Expressing a Nontoxic Domain of Clostridium difficile Toxin A.*

Sauerborn, M. et al, FEMS Microbiology Letters, vol. 155, 1995, p. 45-54.*

Ho, Jason G. S. et al, PNAS Dec. 20, 2005, vol. 102(51), pp. 18373-18378.*

Greco, Antonio et al, Brief Communications, Nature Structural and Molecular Biology, vol. 13(5), May 2006, pp. 460-461.*

Perelle, Sylvie et al, Infection and Immunity, Apr. 1997, vol. 65(4), pp. 1402-1407.*

Frisch, Cornelia et al, Biochemical and Biophysical Research Communications, vol. 300, pp. 706-711, 2003.*

Greco, A et al, 2006, Nat. Struct. Mol. Biol. vol. 13, pp. 460-461.*

Ho, Jason G.S. et al, PNAS, Dec. 20, 2005, vol. 102(51), pp. 18373-18378.*

Von Eichel-Streiber, C et al, Journal of General Microbiology, 1989, vol. 135, pp. 55-64.*

Dove, C. H. et al, Infection and Immunity, Feb. 1990, pp. 480-488, vol. 58(2), Molecular Characterization of the Clostridium difficile Toxin A Gene.*

Rupnik, Maja, FEMS Microbiology Rev, vol. 32, 2008, pp. 541-555.*

Letourneur, Odile et al, Protein Expression and PUrification, vol. 31, 2003, pp. 276-285, Molecular cloning, overexpression in *Escherichia coli*, and purification of 6X his-tagged C-terminal domain of Clostridium difficile toxins A and B.*

Aboudola et al "*Clostridium difficile* Vaccine and Serum Immunoglobulin G Antibody Response to Toxin A" Infection and Immunity vol. 71, pp. 1608-1610. 2003.

Belyi et al "Construction of a Fusion Protein Carrying Antigenic Determinants of Enteric Clostridial Toxins" FEMS Microbiology Letters vol. 225, pp. 325-329. 2003.

Kotloff et al "Safety and Immunogenicity of Increasing Doses of a *Clostridium difficile* Toxoid Vaccine Administered to Healthy Adults" Infection and Immunity vol. 69, pp. 988-995. 2001.

Greenberg et al "Phase I Dose Finding Studies of an Adjuvanted *Clostridium difficile* Toxoid Vaccine" Vaccine vol. 30, pp. 2245-2249. 2012.

Leav et al "Serum Anti-Toxin B Antibody Correlates with Protection from Recurrent *Clostridium difficile* Infection (CDI)" Vaccine vol. 28, pp. 965-969. 2010.

Seregin et al "Adenovirus-Based Vaccination Against *Clostridium difficile* Toxin A Allows for Rapid Humoral Immunity and Complete Protection from Toxin A Lethal Challenge in Mice" Vaccine vol. 30, pp. 1492-1501. 2012.

Gardiner et al "A DNA Vaccine Targeting the Receptor-Binding Domain of *Clostridium difficile* Toxin A" Vaccine vol. 27, pp. 3598-3604. 2009.

Permpoonpattana et al "Immunization with *Bacillus* Spores Expressing Toxin A Peptide Repeats Protects Against Infection with *Clostridium difficile* Strains Producing Toxins A and B" Infection and Immunity vol. 79, pp. 2295-2302. 2011.

NCBI GenBank Accesion No. CBA61156.1, (2009), "Toxin A [Peptoclostridium difficile CD196]", (Retrieved from the Internet on Sep. 17, 2014, /ncbi.nlm.nih.gov/protein/CBA61156>).

NCBI GenBank Accesion No. AAC08437.1, (1999), "Truncated toxin A [Peptoclostridium defficile]", (Retrieved from the Internet on Sep. 17, 2014, /ncbi.nlm.nih.gov/protein/AAC08437>).

NCBI GenBank Accesion No. CAC03681.1, (2000), "Toxin A [,partial [Peptoclostridium difficile CD196]", (Retrieved from the Internet on Sep. 17, 2014, /ncbi.nlm.nih.gov/protein/ CAC03681>).

NCBI GenBank Accesion No. CAA36094.1, (1990), "unnamed protein product [[Peptoclostridium difficile CD196]", (Retrieved from the Internet on Sep. 17, 2014, /ncbi.nlm.nih.gov/protein/ CAA36094>).

International Search Report for PCT/CA2014/000255, issued Jun. 17, 2014.

* cited by examiner

FIG. 1

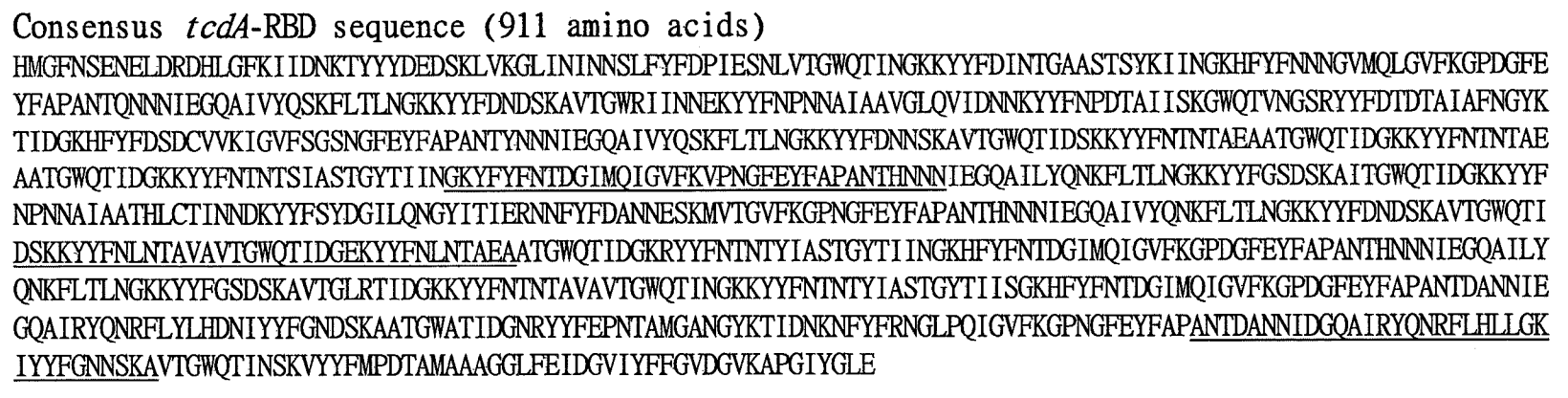

Consensus *tcdA*-RBD sequence (911 amino acids)

HMGFNSENELDRDHLGFKIIDNKTYYYDEDSKLVKGLININNSLFYFDPIESNLVTGWQTINGKKYYFDINTGAASTSYKIINGKHFYFNNNGVMQLGVFKGPDGFE
YFAPANTQNNNIEGQAIVYQSKFLTLNGKKYYFDNDSKAVTGWRIINNEKYYFNPNNAIAAVGLQVIDNNKYYFNPDTAIISKGWQTVNGSRYYFDTDTAIAFNGYK
TIDGKHFYFDSDCVVKIGVFSGSNGFEYFAPANTYNNNIEGQAIVYQSKFLTLNGKKYYFDNNSKAVTGWQTIDSKKYYFNTNTAEAATGWQTIDGKKYYFNTNTAE
AATGWQTIDGKKYYFNTNTSIASTGYTIINGKYFYFNTDGIMQIGVFKVPNGFEYFAPANTHNNNIEGQAILYQNKFLTLNGKKYYFGSDSKAITGWQTIDGKKYYF
NPNNAIAATHLCTINNDKYYFSYDGILQNGYITIERNNFYFDANNESKMVTGVFKGPNGFEYFAPANTHNNNIEGQAIVYQNKFLTLNGKKYYFDNDSKAVTGWQTI
DSKKYYFNLNTAVAVTGWQTIDGEKYYFNLNTAEAATGWQTIDGKRYYFNTNTYIASTGYTIINGKHFYFNTDGIMQIGVFKGPDGFEYFAPANTHNNNIEGQAILY
QNKFLTLNGKKYYFGSDSKAVTGLRTIDGKKYYFNTNTAVAVTGWQTINGKKYYFNTNTYIASTGYTIISGKHFYFNTDGIMQIGVFKGPDGFEYFAPANTDANNIE
GQAIRYQNRFLYLHDNIYYFGNDSKAATGWATIDGNRYYFEPNTAMGANGYKTIDNKNFYFRNGLPQIGVFKGPNGFEYFAPANTDANNIDGQAIRYQNRFLHLLGK
IYYFGNNSKAVTGWQTINSKVYYFMPDTAMAAAGGLFEIDGVIYFFGVDGVKAPGIYGLE

SEQUENCE LISTING

<160> NUMBER OF SEQ ID NOS: 36

<210> SEQ ID NO 1
<211> LENGTH: 2733
<212> TYPE: DNA
<213> ORGANISM: Artificial sequence
<220> FEATURE:
<223> OTHER INFORMATION: Synthetic polynucleotide

<400> SEQUENCE: 1
tttaatagcg agaatgaact ggatcgtgat catctgggct tcaaaatcat cgataataaa 60
acctattatt atgatgaaga tagcaaactg gtgaaaggcc tgattaacat taacaacagc 120
ctgttttact tcgatccgat tgaaagcaat ctggttaccg gttggcagac cattaacggc 180

-continued

```
aaaaaatatt attttgatat taataccggt gcagccagca ccagctataa aattatcaac    240
ggcaagcatt tctatttcaa taataatggc gtgatgcagc tgggcgtttt taaaggtccg    300
gatggttttg aatattttgc accggcaaat acccagaaca ataatattga aggtcaggcc    360
attgtgtatc agagcaaatt tctgaccctg aacggtaaaa aatactactt cgacaacgat    420
agcaaagcag tgaccggttg gcgcattatt aacaacgaga aatattattt caatccgaat    480
aacgccattg cagcagttgg tctgcaggtt attgacaaca ataaatatta ctttaacccg    540
gacaccgcca ttattagcaa aggctggcag accgttaatg gtagccgtta ttatttcgat    600
accgataccg cgattgcctt taatggctat aaaaccatcg acggcaaaca cttctatttt    660
gatagcgatt gcgtggtgaa aattggtgtt tttagcggta gcaacggctt tgaatacttt    720
gcccctgcca atacctacaa caacaacatc gaaggccagg caatcgttta tcagtcaaaa    780
ttcctgacgc tgaatgggaa aaaatattac tttgacaata acagcaaagc cgttacggga    840
tggcagacaa ttgatagcaa aaaatactac ttcaatacca ataccgcaga agcagcaaca    900
ggttggcaga cgatcgatgg taaaaaatat tatttcaaca cgaacacagc cgaagcagcc    960
accggctggc aaaccattga tggaaaaaaa tattacttca atacaaatac gagcattgcc   1020
agcaccggtt ataccattat caacggcaaa tatttctact tcaacaccga tggcattatg   1080
cagattggtg tgttcaaagt gccgaatggc tttgagtatt tcgctccggc taacacccat   1140
aataacaata ttgagggcca ggcgatcctg tatcagaata aattcctgac actgaacggc   1200
aaaaaatact atttcggcag cgattcaaaa gcaattacag gttggcaaac aattgacggg   1260
aaaaagtact attttaatcc gaacaatgcg atcgcagcaa cccatctgtg taccattaat   1320
aacgataaat actactttag ctatgacggc atcctgcaga atggctatat caccattgaa   1380
cgcaacaact tttactttga tgccaacaac gaaagcaaaa tggtgaccgg tgtttttaaa   1440
ggccctaatg gcttcgaata cttcgcacca gcgaatacgc ataacaataa catcgagggt   1500
caagcgattg tctaccagaa taaatttctg actctgaatg gtaaaaaata ttacttcgat   1560
aatgattcaa aagccgtgac cggatggcaa actatcgatt caaaaaaata ctactttaac   1620
ctgaacaccg cagttgcagt tacagggtgg caaaccatcg acggtgagaa atactacttc   1680
aatctgaata cagccgaagc cgctactgga tggcagacga ttgacggaaa acgctattat   1740
tttaatacca acacctatat tgcgagcaca ggctatacca tcattaatgg taaacacttc   1800
tactttaaca cggacggtat catgcaaatc ggcgtgttta aaggcccaga cggtttcgag   1860
tactttgcgc cagcaaacac ccacaataat aacatcgaag gacaagccat cctgtatcaa   1920
aacaaatttc tgacgctgaa tggcaaaaaa tactacttcg gtagtgatag caaagctgtt   1980
acaggtctgc gtaccatcga cggaaaaaaa tattacttta atactaacac ggcagtggca   2040
gtgacgggct ggcaaacgat caacgggaaa aaatactact tcaacaccaa cacgtatatt   2100
gcctcaaccg gctatacaat tatcagcggt aaacactttt atttcaatac agatgggatc   2160
atgcagatcg gagttttcaa aggacctgat ggattcgagt attttgctcc tgcgaatacc   2220
gatgccaata acattgaggg acaggcaatt cgctatcaga atcgttttct gtatctgcac   2280
gataatattt attattttgg caatgattcc aaagcggcaa ccggttgggc caccattgat   2340
ggtaatcgtt attattttga gccgaatacc gcaatgggtg ccaatggtta taaaacgatt   2400
gataacaaaa acttttattt tcgcaacggc ctgccgcaga ttggcgtatt caaaggtcct   2460
aacggttttg agtacttcgc tccagccaat acagatgcaa ataatatcga cggccaggcc   2520
atccgctacc agaaccgctt cctgcatctg ctgggtaaaa tctattattt cggcaacaac   2580
```

-continued

```
agcaaagcgg taactggttg gcaaaccatc aatagcaaag tgtattattt catgccggat   2640

acagcaatgg cagcagccgg tggtctgttt gaaattgatg gtgtgatcta tttctttggt   2700

gtggatggtg ttaaagcacc gggtatttat ggc                                2733


<210> SEQ ID NO 2
<211> LENGTH: 911
<212> TYPE: PRT
<213> ORGANISM: Artificial sequence
<220> FEATURE:
<223> OTHER INFORMATION: Synthetic polypeptide

<400> SEQUENCE: 2

Phe Asn Ser Glu Asn Glu Leu Asp Arg Asp His Leu Gly Phe Lys Ile
1               5                   10                  15

Ile Asp Asn Lys Thr Tyr Tyr Tyr Asp Glu Asp Ser Lys Leu Val Lys
            20                  25                  30

Gly Leu Ile Asn Ile Asn Asn Ser Leu Phe Tyr Phe Asp Pro Ile Glu
        35                  40                  45

Ser Asn Leu Val Thr Gly Trp Gln Thr Ile Asn Gly Lys Lys Tyr Tyr
    50                  55                  60

Phe Asp Ile Asn Thr Gly Ala Ala Ser Thr Ser Tyr Lys Ile Ile Asn
65                  70                  75                  80

Gly Lys His Phe Tyr Phe Asn Asn Asn Gly Val Met Gln Leu Gly Val
                85                  90                  95

Phe Lys Gly Pro Asp Gly Phe Glu Tyr Phe Ala Pro Ala Asn Thr Gln
            100                 105                 110

Asn Asn Asn Ile Glu Gly Gln Ala Ile Val Tyr Gln Ser Lys Phe Leu
        115                 120                 125

Thr Leu Asn Gly Lys Lys Tyr Tyr Phe Asp Asn Asp Ser Lys Ala Val
    130                 135                 140

Thr Gly Trp Arg Ile Ile Asn Asn Glu Lys Tyr Tyr Phe Asn Pro Asn
145                 150                 155                 160

Asn Ala Ile Ala Ala Val Gly Leu Gln Val Ile Asp Asn Asn Lys Tyr
                165                 170                 175

Tyr Phe Asn Pro Asp Thr Ala Ile Ile Ser Lys Gly Trp Gln Thr Val
            180                 185                 190

Asn Gly Ser Arg Tyr Tyr Phe Asp Thr Asp Thr Ala Ile Ala Phe Asn
        195                 200                 205

Gly Tyr Lys Thr Ile Asp Gly Lys His Phe Tyr Phe Asp Ser Asp Cys
    210                 215                 220

Val Val Lys Ile Gly Val Phe Ser Gly Ser Asn Gly Phe Glu Tyr Phe
225                 230                 235                 240

Ala Pro Ala Asn Thr Tyr Asn Asn Asn Ile Glu Gly Gln Ala Ile Val
                245                 250                 255

Tyr Gln Ser Lys Phe Leu Thr Leu Asn Gly Lys Lys Tyr Tyr Phe Asp
            260                 265                 270

Asn Asn Ser Lys Ala Val Thr Gly Trp Gln Thr Ile Asp Ser Lys Lys
        275                 280                 285

Tyr Tyr Phe Asn Thr Asn Thr Ala Glu Ala Ala Thr Gly Trp Gln Thr
    290                 295                 300

Ile Asp Gly Lys Lys Tyr Tyr Phe Asn Thr Asn Thr Ala Glu Ala Ala
305                 310                 315                 320

Thr Gly Trp Gln Thr Ile Asp Gly Lys Lys Tyr Tyr Phe Asn Thr Asn
                325                 330                 335
```

-continued

```
Thr Ser Ile Ala Ser Thr Gly Tyr Thr Ile Ile Asn Gly Lys Tyr Phe
            340                 345                 350

Tyr Phe Asn Thr Asp Gly Ile Met Gln Ile Gly Val Phe Lys Val Pro
        355                 360                 365

Asn Gly Phe Glu Tyr Phe Ala Pro Ala Asn Thr His Asn Asn Asn Ile
    370                 375                 380

Glu Gly Gln Ala Ile Leu Tyr Gln Asn Lys Phe Leu Thr Leu Asn Gly
385                 390                 395                 400

Lys Lys Tyr Tyr Phe Gly Ser Asp Ser Lys Ala Ile Thr Gly Trp Gln
                405                 410                 415

Thr Ile Asp Gly Lys Lys Tyr Tyr Phe Asn Pro Asn Asn Ala Ile Ala
            420                 425                 430

Ala Thr His Leu Cys Thr Ile Asn Asn Asp Lys Tyr Tyr Phe Ser Tyr
        435                 440                 445

Asp Gly Ile Leu Gln Asn Gly Tyr Ile Thr Ile Glu Arg Asn Asn Phe
    450                 455                 460

Tyr Phe Asp Ala Asn Asn Glu Ser Lys Met Val Thr Gly Val Phe Lys
465                 470                 475                 480

Gly Pro Asn Gly Phe Glu Tyr Phe Ala Pro Ala Asn Thr His Asn Asn
                485                 490                 495

Asn Ile Glu Gly Gln Ala Ile Val Tyr Gln Asn Lys Phe Leu Thr Leu
            500                 505                 510

Asn Gly Lys Lys Tyr Tyr Phe Asp Asn Asp Ser Lys Ala Val Thr Gly
        515                 520                 525

Trp Gln Thr Ile Asp Ser Lys Lys Tyr Tyr Phe Asn Leu Asn Thr Ala
    530                 535                 540

Val Ala Val Thr Gly Trp Gln Thr Ile Asp Gly Glu Lys Tyr Tyr Phe
545                 550                 555                 560

Asn Leu Asn Thr Ala Glu Ala Ala Thr Gly Trp Gln Thr Ile Asp Gly
                565                 570                 575

Lys Arg Tyr Tyr Phe Asn Thr Asn Thr Tyr Ile Ala Ser Thr Gly Tyr
            580                 585                 590

Thr Ile Ile Asn Gly Lys His Phe Tyr Phe Asn Thr Asp Gly Ile Met
        595                 600                 605

Gln Ile Gly Val Phe Lys Gly Pro Asp Gly Phe Glu Tyr Phe Ala Pro
    610                 615                 620

Ala Asn Thr His Asn Asn Asn Ile Glu Gly Gln Ala Ile Leu Tyr Gln
625                 630                 635                 640

Asn Lys Phe Leu Thr Leu Asn Gly Lys Lys Tyr Tyr Phe Gly Ser Asp
                645                 650                 655

Ser Lys Ala Val Thr Gly Leu Arg Thr Ile Asp Gly Lys Lys Tyr Tyr
            660                 665                 670

Phe Asn Thr Asn Thr Ala Val Ala Val Thr Gly Trp Gln Thr Ile Asn
        675                 680                 685

Gly Lys Lys Tyr Tyr Phe Asn Thr Asn Thr Tyr Ile Ala Ser Thr Gly
    690                 695                 700

Tyr Thr Ile Ile Ser Gly Lys His Phe Tyr Phe Asn Thr Asp Gly Ile
705                 710                 715                 720

Met Gln Ile Gly Val Phe Lys Gly Pro Asp Gly Phe Glu Tyr Phe Ala
                725                 730                 735

Pro Ala Asn Thr Asp Ala Asn Asn Ile Glu Gly Gln Ala Ile Arg Tyr
            740                 745                 750
```

-continued

```
Gln Asn Arg Phe Leu Tyr Leu His Asp Asn Ile Tyr Tyr Phe Gly Asn
        755                 760                 765

Asp Ser Lys Ala Ala Thr Gly Trp Ala Thr Ile Asp Gly Asn Arg Tyr
    770                 775                 780

Tyr Phe Glu Pro Asn Thr Ala Met Gly Ala Asn Gly Tyr Lys Thr Ile
785                 790                 795                 800

Asp Asn Lys Asn Phe Tyr Phe Arg Asn Gly Leu Pro Gln Ile Gly Val
                805                 810                 815

Phe Lys Gly Pro Asn Gly Phe Glu Tyr Phe Ala Pro Ala Asn Thr Asp
            820                 825                 830

Ala Asn Asn Ile Asp Gly Gln Ala Ile Arg Tyr Gln Asn Arg Phe Leu
        835                 840                 845

His Leu Leu Gly Lys Ile Tyr Tyr Phe Gly Asn Asn Ser Lys Ala Val
    850                 855                 860

Thr Gly Trp Gln Thr Ile Asn Ser Lys Val Tyr Tyr Phe Met Pro Asp
865                 870                 875                 880

Thr Ala Met Ala Ala Ala Gly Gly Leu Phe Glu Ile Asp Gly Val Ile
                885                 890                 895

Tyr Phe Phe Gly Val Asp Gly Val Lys Ala Pro Gly Ile Tyr Gly
            900                 905                 910


<210> SEQ ID NO 3
<211> LENGTH: 1233
<212> TYPE: DNA
<213> ORGANISM: Artificial sequence
<220> FEATURE:
<223> OTHER INFORMATION: Synthetic polynucleotide

<400> SEQUENCE: 3

tttaatagcg agaatgaact ggatcgtgat catctgggct tcaaaatcat cgataataaa     60

acctattatt atgatgaaga tagcaaactg gtgaaaggcc tgattaacat taacaacagc    120

ctgttttact tcgatccgat tgaaagcaat ctggttaccg gttggcagac cattaacggc    180

aaaaaatatt attttgatat taataccggt gcagccagca ccagctataa aattatcaac    240

ggcaagcatt tctatttcaa taataatggc gtgatgcagc tgggcgtttt taaaggtccg    300

gatggttttg aatattttgc accggcaaat acccagaaca ataatattga aggtcaggcc    360

attgtgtatc agagcaaatt tctgaccctg aacggtaaaa aatactactt cgacaacgat    420

agcaaagcag tgaccggttg gcgcattatt aacaacgaga aatattattt caatccgaat    480

aacgccattg cagcagttgg tctgcaggtt attgacaaca ataaatatta ctttaacccg    540

gacaccgcca ttattagcaa aggctggcag accgttaatg gtagccgtta ttatttcgat    600

accgataccg cgattgcctt taatggctat aaaaccatcg acggcaaaca cttctatttt    660

gatagcgatt gcgtggtgaa aattggtgtt tttagcggta gcaacggctt tgaatacttt    720

gcccctgcca atacctacaa caacaacatc gaaggccagg caatcgttta tcagtcaaaa    780

ttcctgacgc tgaatgggaa aaaatattac tttgacaata acagcaaagc cgttacggga    840

tggcagacaa ttgatagcaa aaaatactac ttcaatacca ataccgcaga agcagcaaca    900

ggttggcaga cgatcgatgg taaaaaatat tatttcaaca cgaacacagc cgaagcagcc    960

accggctggc aaaccattga tggaaaaaaa tattacttca atacaaatac gagcattgcc   1020

agcaccggtt ataccattat caacggcaaa tatttctact tcaacaccga tggcattatg   1080

cagattggtg tgttcaaagt gccgaatggc tttgagtatt tcgctccggc taacacccat   1140

aataacaata ttgagggcca ggcgatcctg tatcagaata aattcctgac actgaacggc   1200
```

aaaaaatact atttcggcag cgattcaaaa gca 1233

<210> SEQ ID NO 4
<211> LENGTH: 411
<212> TYPE: PRT
<213> ORGANISM: Artificial sequence
<220> FEATURE:
<223> OTHER INFORMATION: Synthetic polypeptide

<400> SEQUENCE: 4

Phe Asn Ser Glu Asn Glu Leu Asp Arg Asp His Leu Gly Phe Lys Ile
1 5 10 15

Ile Asp Asn Lys Thr Tyr Tyr Tyr Asp Glu Asp Ser Lys Leu Val Lys
20 25 30

Gly Leu Ile Asn Ile Asn Asn Ser Leu Phe Tyr Phe Asp Pro Ile Glu
35 40 45

Ser Asn Leu Val Thr Gly Trp Gln Thr Ile Asn Gly Lys Lys Tyr Tyr
50 55 60

Phe Asp Ile Asn Thr Gly Ala Ala Ser Thr Ser Tyr Lys Ile Ile Asn
65 70 75 80

Gly Lys His Phe Tyr Phe Asn Asn Asn Gly Val Met Gln Leu Gly Val
85 90 95

Phe Lys Gly Pro Asp Gly Phe Glu Tyr Phe Ala Pro Ala Asn Thr Gln
100 105 110

Asn Asn Asn Ile Glu Gly Gln Ala Ile Val Tyr Gln Ser Lys Phe Leu
115 120 125

Thr Leu Asn Gly Lys Lys Tyr Tyr Phe Asp Asn Asp Ser Lys Ala Val
130 135 140

Thr Gly Trp Arg Ile Ile Asn Asn Glu Lys Tyr Tyr Phe Asn Pro Asn
145 150 155 160

Asn Ala Ile Ala Ala Val Gly Leu Gln Val Ile Asp Asn Asn Lys Tyr
165 170 175

Tyr Phe Asn Pro Asp Thr Ala Ile Ile Ser Lys Gly Trp Gln Thr Val
180 185 190

Asn Gly Ser Arg Tyr Tyr Phe Asp Thr Asp Thr Ala Ile Ala Phe Asn
195 200 205

Gly Tyr Lys Thr Ile Asp Gly Lys His Phe Tyr Phe Asp Ser Asp Cys
210 215 220

Val Val Lys Ile Gly Val Phe Ser Gly Ser Asn Gly Phe Glu Tyr Phe
225 230 235 240

Ala Pro Ala Asn Thr Tyr Asn Asn Asn Ile Glu Gly Gln Ala Ile Val
245 250 255

Tyr Gln Ser Lys Phe Leu Thr Leu Asn Gly Lys Lys Tyr Tyr Phe Asp
260 265 270

Asn Asn Ser Lys Ala Val Thr Gly Trp Gln Thr Ile Asp Ser Lys Lys
275 280 285

Tyr Tyr Phe Asn Thr Asn Thr Ala Glu Ala Ala Thr Gly Trp Gln Thr
290 295 300

Ile Asp Gly Lys Lys Tyr Tyr Phe Asn Thr Asn Thr Ala Glu Ala Ala
305 310 315 320

Thr Gly Trp Gln Thr Ile Asp Gly Lys Lys Tyr Tyr Phe Asn Thr Asn
325 330 335

Thr Ser Ile Ala Ser Thr Gly Tyr Thr Ile Ile Asn Gly Lys Tyr Phe
340 345 350

-continued

```
Tyr Phe Asn Thr Asp Gly Ile Met Gln Ile Gly Val Phe Lys Val Pro
        355                 360                 365

Asn Gly Phe Glu Tyr Phe Ala Pro Ala Asn Thr His Asn Asn Asn Ile
    370                 375                 380

Glu Gly Gln Ala Ile Leu Tyr Gln Asn Lys Phe Leu Thr Leu Asn Gly
385                 390                 395                 400

Lys Lys Tyr Tyr Phe Gly Ser Asp Ser Lys Ala
                405                 410


<210> SEQ ID NO 5
<211> LENGTH: 1155
<212> TYPE: DNA
<213> ORGANISM: Artificial sequence
<220> FEATURE:
<223> OTHER INFORMATION: Synthetic polynucleotide

<400> SEQUENCE: 5

gccgaagcag ccaccggctg gcaaaccatt gatggaaaaa aatattactt caatacaaat      60

acgagcattg ccagcaccgg ttataccatt atcaacggca aatatttcta cttcaacacc     120

gatggcatta tgcagattgg tgtgttcaaa gtgccgaatg gctttgagta tttcgctccg     180

gctaacaccc ataataacaa tattgagggc caggcgatcc tgtatcagaa taaattcctg     240

acactgaacg gcaaaaaata ctatttcggc agcgattcaa aagcaattac aggttggcaa     300

acaattgacg ggaaaaagta ctattttaat ccgaacaatg cgatcgcagc aacccatctg     360

tgtaccatta ataacgataa atactacttt agctatgacg gcatcctgca gaatggctat     420

atcaccattg aacgcaacaa cttttacttt gatgccaaca acgaaagcaa aatggtgacc     480

ggtgttttta aaggccctaa tggcttcgaa tacttcgcac cagcgaatac gcataacaat     540

aacatcgagg gtcaagcgat tgtctaccag aataaatttc tgactctgaa tggtaaaaaa     600

tattacttcg ataatgattc aaaagccgtg accggatggc aaactatcga ttcaaaaaaa     660

tactacttta acctgaacac cgcagttgca gttacagggt ggcaaaccat cgacggtgag     720

aaatactact tcaatctgaa tacagccgaa gccgctactg gatggcagac gattgacgga     780

aaacgctatt attttaatac caacacctat attgcgagca caggctatac catcattaat     840

ggtaaacact tctactttaa cacggacggt atcatgcaaa tcggcgtgtt taaaggccca     900

gacggtttcg agtactttgc gccagcaaac acccacaata ataacatcga aggacaagcc     960

atcctgtatc aaaacaaatt tctgacgctg aatggcaaaa aatactactt cggtagtgat    1020

agcaaagctg ttacaggtct gcgtaccatc gacggaaaaa aatattactt taatactaac    1080

acggcagtgg cagtgacggg ctggcaaacg atcaacggga aaaaatacta cttcaacacc    1140

aacacgtata ttgcc                                                     1155


<210> SEQ ID NO 6
<211> LENGTH: 385
<212> TYPE: PRT
<213> ORGANISM: Artificial sequence
<220> FEATURE:
<223> OTHER INFORMATION: Synthetic polypeptide

<400> SEQUENCE: 6

Ala Glu Ala Ala Thr Gly Trp Gln Thr Ile Asp Gly Lys Lys Tyr Tyr
1               5                   10                  15

Phe Asn Thr Asn Thr Ser Ile Ala Ser Thr Gly Tyr Thr Ile Ile Asn
            20                  25                  30

Gly Lys Tyr Phe Tyr Phe Asn Thr Asp Gly Ile Met Gln Ile Gly Val
```

```
        35                  40                  45

Phe Lys Val Pro Asn Gly Phe Glu Tyr Phe Ala Pro Ala Asn Thr His
    50                  55                  60

Asn Asn Asn Ile Glu Gly Gln Ala Ile Leu Tyr Gln Asn Lys Phe Leu
65                  70                  75                  80

Thr Leu Asn Gly Lys Lys Tyr Tyr Phe Gly Ser Asp Ser Lys Ala Ile
                85                  90                  95

Thr Gly Trp Gln Thr Ile Asp Gly Lys Lys Tyr Tyr Phe Asn Pro Asn
            100                 105                 110

Asn Ala Ile Ala Ala Thr His Leu Cys Thr Ile Asn Asn Asp Lys Tyr
        115                 120                 125

Tyr Phe Ser Tyr Asp Gly Ile Leu Gln Asn Gly Tyr Ile Thr Ile Glu
    130                 135                 140

Arg Asn Asn Phe Tyr Phe Asp Ala Asn Asn Glu Ser Lys Met Val Thr
145                 150                 155                 160

Gly Val Phe Lys Gly Pro Asn Gly Phe Glu Tyr Phe Ala Pro Ala Asn
                165                 170                 175

Thr His Asn Asn Asn Ile Glu Gly Gln Ala Ile Val Tyr Gln Asn Lys
            180                 185                 190

Phe Leu Thr Leu Asn Gly Lys Lys Tyr Tyr Phe Asp Asn Asp Ser Lys
        195                 200                 205

Ala Val Thr Gly Trp Gln Thr Ile Asp Ser Lys Lys Tyr Tyr Phe Asn
    210                 215                 220

Leu Asn Thr Ala Val Ala Val Thr Gly Trp Gln Thr Ile Asp Gly Glu
225                 230                 235                 240

Lys Tyr Tyr Phe Asn Leu Asn Thr Ala Glu Ala Ala Thr Gly Trp Gln
                245                 250                 255

Thr Ile Asp Gly Lys Arg Tyr Tyr Phe Asn Thr Asn Thr Tyr Ile Ala
            260                 265                 270

Ser Thr Gly Tyr Thr Ile Ile Asn Gly Lys His Phe Tyr Phe Asn Thr
        275                 280                 285

Asp Gly Ile Met Gln Ile Gly Val Phe Lys Gly Pro Asp Gly Phe Glu
    290                 295                 300

Tyr Phe Ala Pro Ala Asn Thr His Asn Asn Asn Ile Glu Gly Gln Ala
305                 310                 315                 320

Ile Leu Tyr Gln Asn Lys Phe Leu Thr Leu Asn Gly Lys Lys Tyr Tyr
                325                 330                 335

Phe Gly Ser Asp Ser Lys Ala Val Thr Gly Leu Arg Thr Ile Asp Gly
            340                 345                 350

Lys Lys Tyr Tyr Phe Asn Thr Asn Thr Ala Val Ala Val Thr Gly Trp
        355                 360                 365

Gln Thr Ile Asn Gly Lys Lys Tyr Tyr Phe Asn Thr Asn Thr Tyr Ile
    370                 375                 380

Ala
385


<210> SEQ ID NO 7
<211> LENGTH: 1164
<212> TYPE: DNA
<213> ORGANISM: Artificial sequence
<220> FEATURE:
<223> OTHER INFORMATION: Synthetic polynucleotide

<400> SEQUENCE: 7

aaagccgtga ccggatggca aactatcgat tcaaaaaaat actactttaa cctgaacacc      60
```

```
gcagttgcag ttacagggtg gcaaaccatc gacggtgaga aatactactt caatctgaat    120

acagccgaag ccgctactgg atggcagacg attgacggaa aacgctatta ttttaatacc    180

aacacctata ttgcgagcac aggctatacc atcattaatg gtaaacactt ctactttaac    240

acggacggta tcatgcaaat cggcgtgttt aaaggcccag acggtttcga gtactttgcg    300

ccagcaaaca cccacaataa taacatcgaa ggacaagcca tcctgtatca aaacaaattt    360

ctgacgctga atggcaaaaa atactacttc ggtagtgata gcaaagctgt tacaggtctg    420

cgtaccatcg acggaaaaaa atattacttt aatactaaca cggcagtggc agtgacgggc    480

tggcaaacga tcaacgggaa aaaatactac ttcaacacca acacgtatat tgcctcaacc    540

ggctatacaa ttatcagcgg taaacacttt tatttcaata cagatgggat catgcagatc    600

ggagttttca aaggacctga tggattcgag tattttgctc ctgcgaatac cgatgccaat    660

aacattgagg gacaggcaat tcgctatcag aatcgttttc tgtatctgca cgataatatt    720

tattattttg gcaatgattc caaagcggca accggttggg ccaccattga tggtaatcgt    780

tattattttg agccgaatac cgcaatgggt gccaatggtt ataaaacgat tgataacaaa    840

aacttttatt ttcgcaacgg cctgccgcag attggcgtat tcaaaggtcc taacggtttt    900

gagtacttcg ctccagccaa tacagatgca aataatatcg acggccaggc catccgctac    960

cagaaccgct tcctgcatct gctgggtaaa atctattatt tcggcaacaa cagcaaagcg   1020

gtaactggtt ggcaaaccat caatagcaaa gtgtattatt tcatgccgga tacagcaatg   1080

gcagcagccg gtggtctgtt tgaaattgat ggtgtgatct atttctttgg tgtggatggt   1140

gttaaagcac cgggtattta tggc                                          1164


<210> SEQ ID NO 8
<211> LENGTH: 388
<212> TYPE: PRT
<213> ORGANISM: Artificial sequence
<220> FEATURE:
<223> OTHER INFORMATION: Synthetic polypeptide

<400> SEQUENCE: 8

Lys Ala Val Thr Gly Trp Gln Thr Ile Asp Ser Lys Lys Tyr Tyr Phe
1               5                   10                  15

Asn Leu Asn Thr Ala Val Ala Val Thr Gly Trp Gln Thr Ile Asp Gly
            20                  25                  30

Glu Lys Tyr Tyr Phe Asn Leu Asn Thr Ala Glu Ala Ala Thr Gly Trp
        35                  40                  45

Gln Thr Ile Asp Gly Lys Arg Tyr Tyr Phe Asn Thr Asn Thr Tyr Ile
    50                  55                  60

Ala Ser Thr Gly Tyr Thr Ile Ile Asn Gly Lys His Phe Tyr Phe Asn
65                  70                  75                  80

Thr Asp Gly Ile Met Gln Ile Gly Val Phe Lys Gly Pro Asp Gly Phe
                85                  90                  95

Glu Tyr Phe Ala Pro Ala Asn Thr His Asn Asn Asn Ile Glu Gly Gln
            100                 105                 110

Ala Ile Leu Tyr Gln Asn Lys Phe Leu Thr Leu Asn Gly Lys Lys Tyr
        115                 120                 125

Tyr Phe Gly Ser Asp Ser Lys Ala Val Thr Gly Leu Arg Thr Ile Asp
    130                 135                 140

Gly Lys Lys Tyr Tyr Phe Asn Thr Asn Thr Ala Val Ala Val Thr Gly
145                 150                 155                 160
```

```
Trp Gln Thr Ile Asn Gly Lys Lys Tyr Tyr Phe Asn Thr Asn Thr Tyr
                165                 170                 175

Ile Ala Ser Thr Gly Tyr Thr Ile Ile Ser Gly Lys His Phe Tyr Phe
            180                 185                 190

Asn Thr Asp Gly Ile Met Gln Ile Gly Val Phe Lys Gly Pro Asp Gly
        195                 200                 205

Phe Glu Tyr Phe Ala Pro Ala Asn Thr Asp Ala Asn Asn Ile Glu Gly
    210                 215                 220

Gln Ala Ile Arg Tyr Gln Asn Arg Phe Leu Tyr Leu His Asp Asn Ile
225                 230                 235                 240

Tyr Tyr Phe Gly Asn Asp Ser Lys Ala Ala Thr Gly Trp Ala Thr Ile
                245                 250                 255

Asp Gly Asn Arg Tyr Tyr Phe Glu Pro Asn Thr Ala Met Gly Ala Asn
            260                 265                 270

Gly Tyr Lys Thr Ile Asp Asn Lys Asn Phe Tyr Phe Arg Asn Gly Leu
        275                 280                 285

Pro Gln Ile Gly Val Phe Lys Gly Pro Asn Gly Phe Glu Tyr Phe Ala
    290                 295                 300

Pro Ala Asn Thr Asp Ala Asn Asn Ile Asp Gly Gln Ala Ile Arg Tyr
305                 310                 315                 320

Gln Asn Arg Phe Leu His Leu Leu Gly Lys Ile Tyr Tyr Phe Gly Asn
                325                 330                 335

Asn Ser Lys Ala Val Thr Gly Trp Gln Thr Ile Asn Ser Lys Val Tyr
            340                 345                 350

Tyr Phe Met Pro Asp Thr Ala Met Ala Ala Ala Gly Gly Leu Phe Glu
        355                 360                 365

Ile Asp Gly Val Ile Tyr Phe Phe Gly Val Asp Gly Val Lys Ala Pro
    370                 375                 380

Gly Ile Tyr Gly
385
```

<210> SEQ ID NO 9
<211> LENGTH: 36
<212> TYPE: PRT
<213> ORGANISM: Artificial sequence
<220> FEATURE:
<223> OTHER INFORMATION: Synthetic polypeptide

<400> SEQUENCE: 9

```
Gly Lys Tyr Phe Tyr Phe Asn Thr Asp Gly Ile Met Gln Ile Gly Val
1               5                   10                  15

Phe Lys Val Pro Asn Gly Phe Glu Tyr Phe Ala Pro Ala Asn Thr His
            20                  25                  30

Asn Asn Asn Ile
        35
```

<210> SEQ ID NO 10
<211> LENGTH: 35
<212> TYPE: PRT
<213> ORGANISM: Artificial sequence
<220> FEATURE:
<223> OTHER INFORMATION: Synthetic polypeptide

<400> SEQUENCE: 10

```
Asp Ser Lys Lys Tyr Tyr Phe Asn Leu Asn Thr Ala Val Ala Val Thr
1               5                   10                  15

Gly Trp Gln Thr Ile Asp Gly Glu Lys Tyr Tyr Phe Asn Leu Asn Thr
            20                  25                  30
```

-continued

```
Ala Glu Ala
        35


<210> SEQ ID NO 11
<211> LENGTH: 35
<212> TYPE: PRT
<213> ORGANISM: Artificial sequence
<220> FEATURE:
<223> OTHER INFORMATION: Synthetic polypeptide

<400> SEQUENCE: 11

Ala Asn Thr Asp Ala Asn Asn Ile Asp Gly Gln Ala Ile Arg Tyr Gln
1               5                   10                  15

Asn Arg Phe Leu His Leu Leu Gly Lys Ile Tyr Tyr Phe Gly Asn Asn
            20                  25                  30

Ser Lys Ala
        35


<210> SEQ ID NO 12
<211> LENGTH: 39
<212> TYPE: PRT
<213> ORGANISM: Artificial sequence
<220> FEATURE:
<223> OTHER INFORMATION: Synthetic polypeptide

<400> SEQUENCE: 12

Ala Lys Ser Tyr Phe Leu Ser Asp Asp Gly Glu Ser Ile Leu Glu Leu
1               5                   10                  15

Asn Lys Tyr Arg Ile Pro Glu Arg Leu Lys Asn Lys Glu Lys Val Lys
            20                  25                  30

Val Thr Phe Ile Gly His Gly
        35


<210> SEQ ID NO 13
<211> LENGTH: 41
<212> TYPE: PRT
<213> ORGANISM: Artificial sequence
<220> FEATURE:
<223> OTHER INFORMATION: Synthetic polypeptide

<400> SEQUENCE: 13

Glu Lys Asn Leu His Phe Val Trp Ile Gly Gly Glu Val Ser Asp Ile
1               5                   10                  15

Ala Leu Glu Tyr Ile Lys Gln Trp Ala Asp Ile Asn Ala Glu Tyr Asn
            20                  25                  30

Ile Lys Leu Trp Tyr Asp Ser Glu Ala
        35                  40


<210> SEQ ID NO 14
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 14

Gly Val Tyr Leu Asp Val Asp Met Leu Pro Gly Ile His Ser Asp Leu
1               5                   10                  15

Phe Lys Thr Ile Ser Arg Pro Ser Ser Ile Gly Leu Asp Arg Trp Glu
            20                  25                  30

Met Ile Lys Leu Glu Ala
        35
```

<210> SEQ ID NO 15
<211> LENGTH: 34
<212> TYPE: PRT
<213> ORGANISM: Artificial sequence
<220> FEATURE:
<223> OTHER INFORMATION: Synthetic polypeptide

<400> SEQUENCE: 15

```
Gly Ala Tyr Ala Ser Ala Tyr Tyr Asp Phe Ile Asn Leu Gln Glu Asn
1               5                   10                  15

Thr Ile Glu Lys Thr Leu Lys Ala Ser Asp Leu Ile Glu Phe Lys Phe
            20                  25                  30

Pro Glu
```

<210> SEQ ID NO 16
<211> LENGTH: 34
<212> TYPE: PRT
<213> ORGANISM: Artificial sequence
<220> FEATURE:
<223> OTHER INFORMATION: Synthetic polypeptide

<400> SEQUENCE: 16

```
Ile Leu His Asp Lys Ala Thr Ser Val Val Asn Tyr Phe Asn His Leu
1               5                   10                  15

Ser Glu Ser Lys Lys Tyr Gly Pro Leu Lys Thr Glu Asp Asp Lys Ile
            20                  25                  30

Leu Val
```

<210> SEQ ID NO 17
<211> LENGTH: 29
<212> TYPE: PRT
<213> ORGANISM: Artificial sequence
<220> FEATURE:
<223> OTHER INFORMATION: Synthetic polypeptide

<400> SEQUENCE: 17

```
Leu Pro Asn Ala Pro Ser Arg Val Phe Trp Trp Glu Thr Gly Ala Val
1               5                   10                  15

Pro Gly Leu Arg Ser Leu Glu Asn Asp Gly Thr Arg Leu
            20                  25
```

<210> SEQ ID NO 18
<211> LENGTH: 42
<212> TYPE: PRT
<213> ORGANISM: Artificial sequence
<220> FEATURE:
<223> OTHER INFORMATION: Synthetic polypeptide

<400> SEQUENCE: 18

```
Gly Ala Ile Ser Lys Thr Ser Gln Lys Ser Ile Ile His Tyr Lys Lys
1               5                   10                  15

Asp Ser Lys Asn Ile Leu Glu Phe Tyr Asn Asp Ser Thr Leu Glu Phe
            20                  25                  30

Asn Ser Lys Asp Phe Ile Ala Glu Asp Ile
        35                  40
```

<210> SEQ ID NO 19
<211> LENGTH: 121
<212> TYPE: PRT
<213> ORGANISM: Neisseria meningitidis

<400> SEQUENCE: 19

```
Met Lys Lys Leu Leu Ile Ala Ala Met Met Ala Ala Ala Leu Ala Ala
1               5                   10                  15

Cys Ser Gln Glu Ala Lys Gln Glu Val Lys Glu Ala Val Gln Ala Val
            20                  25                  30

Glu Ser Asp Val Lys Asp Thr Ala Ala Ser Ala Ala Glu Ser Ala Ala
        35                  40                  45

Ser Ala Val Glu Glu Ala Lys Asp Gln Val Lys Asp Ala Ala Ala Asp
    50                  55                  60

Ala Lys Ala Ser Ala Glu Glu Ala Val Thr Glu Ala Lys Glu Ala Val
65                  70                  75                  80

Thr Glu Ala Lys Glu Ala Val Thr Glu Ala Lys Glu Ala Val Thr Glu
                85                  90                  95

Ala Ala Lys Asp Thr Leu Asn Lys Ala Ala Asp Ala Thr Gln Glu Ala
            100                 105                 110

Ala Asp Lys Met Lys Asp Ala Ala Lys
        115                 120


<210> SEQ ID NO 20
<211> LENGTH: 39
<212> TYPE: PRT
<213> ORGANISM: Artificial sequence
<220> FEATURE:
<223> OTHER INFORMATION: Synthetic polypeptide

<400> SEQUENCE: 20

Lys Lys Leu Leu Ile Ala Ala Met Met Ala Ala Ala Leu Ala Ala Cys
1               5                   10                  15

Ser Gln Glu Ala Lys Gln Glu Val Lys Glu Ala Val Gln Ala Val Glu
            20                  25                  30

Ser Asp Val Lys Asp Thr Ala
        35


<210> SEQ ID NO 21
<211> LENGTH: 2751
<212> TYPE: DNA
<213> ORGANISM: Artificial sequence
<220> FEATURE:
<223> OTHER INFORMATION: Synthetic polynucleotide
<220> FEATURE:
<221> NAME/KEY: CDS
<222> LOCATION: (1)..(2751)

<400> SEQUENCE: 21

cat atg gga tcc ttt aat agc gag aat gaa ctg gat cgt gat cat ctg       48
His Met Gly Ser Phe Asn Ser Glu Asn Glu Leu Asp Arg Asp His Leu
1               5                   10                  15

ggc ttc aaa atc atc gat aat aaa acc tat tat tat gat gaa gat agc       96
Gly Phe Lys Ile Ile Asp Asn Lys Thr Tyr Tyr Tyr Asp Glu Asp Ser
            20                  25                  30

aaa ctg gtg aaa ggc ctg att aac att aac aac agc ctg ttt tac ttc      144
Lys Leu Val Lys Gly Leu Ile Asn Ile Asn Asn Ser Leu Phe Tyr Phe
        35                  40                  45

gat ccg att gaa agc aat ctg gtt acc ggt tgg cag acc att aac ggc      192
Asp Pro Ile Glu Ser Asn Leu Val Thr Gly Trp Gln Thr Ile Asn Gly
    50                  55                  60

aaa aaa tat tat ttt gat att aat acc ggt gca gcc agc acc agc tat      240
Lys Lys Tyr Tyr Phe Asp Ile Asn Thr Gly Ala Ala Ser Thr Ser Tyr
65                  70                  75                  80

aaa att atc aac ggc aag cat ttc tat ttc aat aat aat ggc gtg atg      288
Lys Ile Ile Asn Gly Lys His Phe Tyr Phe Asn Asn Asn Gly Val Met
```

-continued

```
                85                  90                  95

cag ctg ggc gtt ttt aaa ggt ccg gat ggt ttt gaa tat ttt gca ccg      336
Gln Leu Gly Val Phe Lys Gly Pro Asp Gly Phe Glu Tyr Phe Ala Pro
            100                 105                 110

gca aat acc cag aac aat aat att gaa ggt cag gcc att gtg tat cag      384
Ala Asn Thr Gln Asn Asn Asn Ile Glu Gly Gln Ala Ile Val Tyr Gln
        115                 120                 125

agc aaa ttt ctg acc ctg aac ggt aaa aaa tac tac ttc gac aac gat      432
Ser Lys Phe Leu Thr Leu Asn Gly Lys Lys Tyr Tyr Phe Asp Asn Asp
    130                 135                 140

agc aaa gca gtg acc ggt tgg cgc att att aac aac gag aaa tat tat      480
Ser Lys Ala Val Thr Gly Trp Arg Ile Ile Asn Asn Glu Lys Tyr Tyr
145                 150                 155                 160

ttc aat ccg aat aac gcc att gca gca gtt ggt ctg cag gtt att gac      528
Phe Asn Pro Asn Asn Ala Ile Ala Ala Val Gly Leu Gln Val Ile Asp
                165                 170                 175

aac aat aaa tat tac ttt aac ccg gac acc gcc att att agc aaa ggc      576
Asn Asn Lys Tyr Tyr Phe Asn Pro Asp Thr Ala Ile Ile Ser Lys Gly
            180                 185                 190

tgg cag acc gtt aat ggt agc cgt tat tat ttc gat acc gat acc gcg      624
Trp Gln Thr Val Asn Gly Ser Arg Tyr Tyr Phe Asp Thr Asp Thr Ala
        195                 200                 205

att gcc ttt aat ggc tat aaa acc atc gac ggc aaa cac ttc tat ttt      672
Ile Ala Phe Asn Gly Tyr Lys Thr Ile Asp Gly Lys His Phe Tyr Phe
    210                 215                 220

gat agc gat tgc gtg gtg aaa att ggt gtt ttt agc ggt agc aac ggc      720
Asp Ser Asp Cys Val Val Lys Ile Gly Val Phe Ser Gly Ser Asn Gly
225                 230                 235                 240

ttt gaa tac ttt gcc cct gcc aat acc tac aac aac aac atc gaa ggc      768
Phe Glu Tyr Phe Ala Pro Ala Asn Thr Tyr Asn Asn Asn Ile Glu Gly
                245                 250                 255

cag gca atc gtt tat cag tca aaa ttc ctg acg ctg aat ggg aaa aaa      816
Gln Ala Ile Val Tyr Gln Ser Lys Phe Leu Thr Leu Asn Gly Lys Lys
            260                 265                 270

tat tac ttt gac aat aac agc aaa gcc gtt acg gga tgg cag aca att      864
Tyr Tyr Phe Asp Asn Asn Ser Lys Ala Val Thr Gly Trp Gln Thr Ile
        275                 280                 285

gat agc aaa aaa tac tac ttc aat acc aat acc gca gaa gca gca aca      912
Asp Ser Lys Lys Tyr Tyr Phe Asn Thr Asn Thr Ala Glu Ala Ala Thr
    290                 295                 300

ggt tgg cag acg atc gat ggt aaa aaa tat tat ttc aac acg aac aca      960
Gly Trp Gln Thr Ile Asp Gly Lys Lys Tyr Tyr Phe Asn Thr Asn Thr
305                 310                 315                 320

gcc gaa gca gcc acc ggc tgg caa acc att gat gga aaa aaa tat tac     1008
Ala Glu Ala Ala Thr Gly Trp Gln Thr Ile Asp Gly Lys Lys Tyr Tyr
                325                 330                 335

ttc aat aca aat acg agc att gcc agc acc ggt tat acc att atc aac     1056
Phe Asn Thr Asn Thr Ser Ile Ala Ser Thr Gly Tyr Thr Ile Ile Asn
            340                 345                 350

ggc aaa tat ttc tac ttc aac acc gat ggc att atg cag att ggt gtg     1104
Gly Lys Tyr Phe Tyr Phe Asn Thr Asp Gly Ile Met Gln Ile Gly Val
        355                 360                 365

ttc aaa gtg ccg aat ggc ttt gag tat ttc gct ccg gct aac acc cat     1152
Phe Lys Val Pro Asn Gly Phe Glu Tyr Phe Ala Pro Ala Asn Thr His
    370                 375                 380

aat aac aat att gag ggc cag gcg atc ctg tat cag aat aaa ttc ctg     1200
Asn Asn Asn Ile Glu Gly Gln Ala Ile Leu Tyr Gln Asn Lys Phe Leu
385                 390                 395                 400

aca ctg aac ggc aaa aaa tac tat ttc ggc agc gat tca aaa gca att     1248
```

-continued

```
Thr Leu Asn Gly Lys Lys Tyr Tyr Phe Gly Ser Asp Ser Lys Ala Ile
                405                 410                 415

aca ggt tgg caa aca att gac ggg aaa aag tac tat ttt aat ccg aac      1296
Thr Gly Trp Gln Thr Ile Asp Gly Lys Lys Tyr Tyr Phe Asn Pro Asn
            420                 425                 430

aat gcg atc gca gca acc cat ctg tgt acc att aat aac gat aaa tac      1344
Asn Ala Ile Ala Ala Thr His Leu Cys Thr Ile Asn Asn Asp Lys Tyr
        435                 440                 445

tac ttt agc tat gac ggc atc ctg cag aat ggc tat atc acc att gaa      1392
Tyr Phe Ser Tyr Asp Gly Ile Leu Gln Asn Gly Tyr Ile Thr Ile Glu
    450                 455                 460

cgc aac aac ttt tac ttt gat gcc aac aac gaa agc aaa atg gtg acc      1440
Arg Asn Asn Phe Tyr Phe Asp Ala Asn Asn Glu Ser Lys Met Val Thr
465                 470                 475                 480

ggt gtt ttt aaa ggc cct aat ggc ttc gaa tac ttc gca cca gcg aat      1488
Gly Val Phe Lys Gly Pro Asn Gly Phe Glu Tyr Phe Ala Pro Ala Asn
                485                 490                 495

acg cat aac aat aac atc gag ggt caa gcg att gtc tac cag aat aaa      1536
Thr His Asn Asn Asn Ile Glu Gly Gln Ala Ile Val Tyr Gln Asn Lys
            500                 505                 510

ttt ctg act ctg aat ggt aaa aaa tat tac ttc gat aat gat tca aaa      1584
Phe Leu Thr Leu Asn Gly Lys Lys Tyr Tyr Phe Asp Asn Asp Ser Lys
        515                 520                 525

gcc gtg acc gga tgg caa act atc gat tca aaa aaa tac tac ttt aac      1632
Ala Val Thr Gly Trp Gln Thr Ile Asp Ser Lys Lys Tyr Tyr Phe Asn
    530                 535                 540

ctg aac acc gca gtt gca gtt aca ggg tgg caa acc atc gac ggt gag      1680
Leu Asn Thr Ala Val Ala Val Thr Gly Trp Gln Thr Ile Asp Gly Glu
545                 550                 555                 560

aaa tac tac ttc aat ctg aat aca gcc gaa gcc gct act gga tgg cag      1728
Lys Tyr Tyr Phe Asn Leu Asn Thr Ala Glu Ala Ala Thr Gly Trp Gln
                565                 570                 575

acg att gac gga aaa cgc tat tat ttt aat acc aac acc tat att gcg      1776
Thr Ile Asp Gly Lys Arg Tyr Tyr Phe Asn Thr Asn Thr Tyr Ile Ala
            580                 585                 590

agc aca ggc tat acc atc att aat ggt aaa cac ttc tac ttt aac acg      1824
Ser Thr Gly Tyr Thr Ile Ile Asn Gly Lys His Phe Tyr Phe Asn Thr
        595                 600                 605

gac ggt atc atg caa atc ggc gtg ttt aaa ggc cca gac ggt ttc gag      1872
Asp Gly Ile Met Gln Ile Gly Val Phe Lys Gly Pro Asp Gly Phe Glu
    610                 615                 620

tac ttt gcg cca gca aac acc cac aat aat aac atc gaa gga caa gcc      1920
Tyr Phe Ala Pro Ala Asn Thr His Asn Asn Asn Ile Glu Gly Gln Ala
625                 630                 635                 640

atc ctg tat caa aac aaa ttt ctg acg ctg aat ggc aaa aaa tac tac      1968
Ile Leu Tyr Gln Asn Lys Phe Leu Thr Leu Asn Gly Lys Lys Tyr Tyr
                645                 650                 655

ttc ggt agt gat agc aaa gct gtt aca ggt ctg cgt acc atc gac gga      2016
Phe Gly Ser Asp Ser Lys Ala Val Thr Gly Leu Arg Thr Ile Asp Gly
            660                 665                 670

aaa aaa tat tac ttt aat act aac acg gca gtg gca gtg acg ggc tgg      2064
Lys Lys Tyr Tyr Phe Asn Thr Asn Thr Ala Val Ala Val Thr Gly Trp
        675                 680                 685

caa acg atc aac ggg aaa aaa tac tac ttc aac acc aac acg tat att      2112
Gln Thr Ile Asn Gly Lys Lys Tyr Tyr Phe Asn Thr Asn Thr Tyr Ile
    690                 695                 700

gcc tca acc ggc tat aca att atc agc ggt aaa cac ttt tat ttc aat      2160
Ala Ser Thr Gly Tyr Thr Ile Ile Ser Gly Lys His Phe Tyr Phe Asn
705                 710                 715                 720
```

```
aca gat ggg atc atg cag atc gga gtt ttc aaa gga cct gat gga ttc      2208
Thr Asp Gly Ile Met Gln Ile Gly Val Phe Lys Gly Pro Asp Gly Phe
                725                 730                 735

gag tat ttt gct cct gcg aat acc gat gcc aat aac att gag gga cag      2256
Glu Tyr Phe Ala Pro Ala Asn Thr Asp Ala Asn Asn Ile Glu Gly Gln
            740                 745                 750

gca att cgc tat cag aat cgt ttt ctg tat ctg cac gat aat att tat      2304
Ala Ile Arg Tyr Gln Asn Arg Phe Leu Tyr Leu His Asp Asn Ile Tyr
        755                 760                 765

tat ttt ggc aat gat tcc aaa gcg gca acc ggt tgg gcc acc att gat      2352
Tyr Phe Gly Asn Asp Ser Lys Ala Ala Thr Gly Trp Ala Thr Ile Asp
    770                 775                 780

ggt aat cgt tat tat ttt gag ccg aat acc gca atg ggt gcc aat ggt      2400
Gly Asn Arg Tyr Tyr Phe Glu Pro Asn Thr Ala Met Gly Ala Asn Gly
785                 790                 795                 800

tat aaa acg att gat aac aaa aac ttt tat ttt cgc aac ggc ctg ccg      2448
Tyr Lys Thr Ile Asp Asn Lys Asn Phe Tyr Phe Arg Asn Gly Leu Pro
                805                 810                 815

cag att ggc gta ttc aaa ggt cct aac ggt ttt gag tac ttc gct cca      2496
Gln Ile Gly Val Phe Lys Gly Pro Asn Gly Phe Glu Tyr Phe Ala Pro
            820                 825                 830

gcc aat aca gat gca aat aat atc gac ggc cag gcc atc cgc tac cag      2544
Ala Asn Thr Asp Ala Asn Asn Ile Asp Gly Gln Ala Ile Arg Tyr Gln
        835                 840                 845

aac cgc ttc ctg cat ctg ctg ggt aaa atc tat tat ttc ggc aac aac      2592
Asn Arg Phe Leu His Leu Leu Gly Lys Ile Tyr Tyr Phe Gly Asn Asn
    850                 855                 860

agc aaa gcg gta act ggt tgg caa acc atc aat agc aaa gtg tat tat      2640
Ser Lys Ala Val Thr Gly Trp Gln Thr Ile Asn Ser Lys Val Tyr Tyr
865                 870                 875                 880

ttc atg ccg gat aca gca atg gca gca gcc ggt ggt ctg ttt gaa att      2688
Phe Met Pro Asp Thr Ala Met Ala Ala Ala Gly Gly Leu Phe Glu Ile
                885                 890                 895

gat ggt gtg atc tat ttc ttt ggt gtg gat ggt gtt aaa gca ccg ggt      2736
Asp Gly Val Ile Tyr Phe Phe Gly Val Asp Gly Val Lys Ala Pro Gly
            900                 905                 910

att tat ggc ctc gag                                                  2751
Ile Tyr Gly Leu Glu
        915


<210> SEQ ID NO 22
<211> LENGTH: 917
<212> TYPE: PRT
<213> ORGANISM: Artificial sequence
<220> FEATURE:
<223> OTHER INFORMATION: Synthetic Construct

<400> SEQUENCE: 22

His Met Gly Ser Phe Asn Ser Glu Asn Glu Leu Asp Arg Asp His Leu
1               5                   10                  15

Gly Phe Lys Ile Ile Asp Asn Lys Thr Tyr Tyr Tyr Asp Glu Asp Ser
            20                  25                  30

Lys Leu Val Lys Gly Leu Ile Asn Ile Asn Asn Ser Leu Phe Tyr Phe
        35                  40                  45

Asp Pro Ile Glu Ser Asn Leu Val Thr Gly Trp Gln Thr Ile Asn Gly
    50                  55                  60

Lys Lys Tyr Tyr Phe Asp Ile Asn Thr Gly Ala Ala Ser Thr Ser Tyr
65                  70                  75                  80

Lys Ile Ile Asn Gly Lys His Phe Tyr Phe Asn Asn Asn Gly Val Met
                85                  90                  95
```

-continued

Gln Leu Gly Val Phe Lys Gly Pro Asp Gly Phe Glu Tyr Phe Ala Pro
100 105 110

Ala Asn Thr Gln Asn Asn Asn Ile Glu Gly Gln Ala Ile Val Tyr Gln
115 120 125

Ser Lys Phe Leu Thr Leu Asn Gly Lys Lys Tyr Tyr Phe Asp Asn Asp
130 135 140

Ser Lys Ala Val Thr Gly Trp Arg Ile Ile Asn Asn Glu Lys Tyr Tyr
145 150 155 160

Phe Asn Pro Asn Asn Ala Ile Ala Ala Val Gly Leu Gln Val Ile Asp
165 170 175

Asn Asn Lys Tyr Tyr Phe Asn Pro Asp Thr Ala Ile Ile Ser Lys Gly
180 185 190

Trp Gln Thr Val Asn Gly Ser Arg Tyr Tyr Phe Asp Thr Asp Thr Ala
195 200 205

Ile Ala Phe Asn Gly Tyr Lys Thr Ile Asp Gly Lys His Phe Tyr Phe
210 215 220

Asp Ser Asp Cys Val Val Lys Ile Gly Val Phe Ser Gly Ser Asn Gly
225 230 235 240

Phe Glu Tyr Phe Ala Pro Ala Asn Thr Tyr Asn Asn Asn Ile Glu Gly
245 250 255

Gln Ala Ile Val Tyr Gln Ser Lys Phe Leu Thr Leu Asn Gly Lys Lys
260 265 270

Tyr Tyr Phe Asp Asn Asn Ser Lys Ala Val Thr Gly Trp Gln Thr Ile
275 280 285

Asp Ser Lys Lys Tyr Tyr Phe Asn Thr Asn Thr Ala Glu Ala Ala Thr
290 295 300

Gly Trp Gln Thr Ile Asp Gly Lys Lys Tyr Tyr Phe Asn Thr Asn Thr
305 310 315 320

Ala Glu Ala Ala Thr Gly Trp Gln Thr Ile Asp Gly Lys Lys Tyr Tyr
325 330 335

Phe Asn Thr Asn Thr Ser Ile Ala Ser Thr Gly Tyr Thr Ile Ile Asn
340 345 350

Gly Lys Tyr Phe Tyr Phe Asn Thr Asp Gly Ile Met Gln Ile Gly Val
355 360 365

Phe Lys Val Pro Asn Gly Phe Glu Tyr Phe Ala Pro Ala Asn Thr His
370 375 380

Asn Asn Asn Ile Glu Gly Gln Ala Ile Leu Tyr Gln Asn Lys Phe Leu
385 390 395 400

Thr Leu Asn Gly Lys Lys Tyr Tyr Phe Gly Ser Asp Ser Lys Ala Ile
405 410 415

Thr Gly Trp Gln Thr Ile Asp Gly Lys Lys Tyr Tyr Phe Asn Pro Asn
420 425 430

Asn Ala Ile Ala Ala Thr His Leu Cys Thr Ile Asn Asn Asp Lys Tyr
435 440 445

Tyr Phe Ser Tyr Asp Gly Ile Leu Gln Asn Gly Tyr Ile Thr Ile Glu
450 455 460

Arg Asn Asn Phe Tyr Phe Asp Ala Asn Asn Glu Ser Lys Met Val Thr
465 470 475 480

Gly Val Phe Lys Gly Pro Asn Gly Phe Glu Tyr Phe Ala Pro Ala Asn
485 490 495

Thr His Asn Asn Asn Ile Glu Gly Gln Ala Ile Val Tyr Gln Asn Lys
500 505 510

```
Phe Leu Thr Leu Asn Gly Lys Lys Tyr Tyr Phe Asp Asn Asp Ser Lys
        515                 520                 525

Ala Val Thr Gly Trp Gln Thr Ile Asp Ser Lys Lys Tyr Tyr Phe Asn
    530                 535                 540

Leu Asn Thr Ala Val Ala Val Thr Gly Trp Gln Thr Ile Asp Gly Glu
545                 550                 555                 560

Lys Tyr Tyr Phe Asn Leu Asn Thr Ala Glu Ala Ala Thr Gly Trp Gln
                565                 570                 575

Thr Ile Asp Gly Lys Arg Tyr Tyr Phe Asn Thr Asn Thr Tyr Ile Ala
            580                 585                 590

Ser Thr Gly Tyr Thr Ile Ile Asn Gly Lys His Phe Tyr Phe Asn Thr
        595                 600                 605

Asp Gly Ile Met Gln Ile Gly Val Phe Lys Gly Pro Asp Gly Phe Glu
    610                 615                 620

Tyr Phe Ala Pro Ala Asn Thr His Asn Asn Asn Ile Glu Gly Gln Ala
625                 630                 635                 640

Ile Leu Tyr Gln Asn Lys Phe Leu Thr Leu Asn Gly Lys Lys Tyr Tyr
                645                 650                 655

Phe Gly Ser Asp Ser Lys Ala Val Thr Gly Leu Arg Thr Ile Asp Gly
            660                 665                 670

Lys Lys Tyr Tyr Phe Asn Thr Asn Thr Ala Val Ala Val Thr Gly Trp
        675                 680                 685

Gln Thr Ile Asn Gly Lys Lys Tyr Tyr Phe Asn Thr Asn Thr Tyr Ile
    690                 695                 700

Ala Ser Thr Gly Tyr Thr Ile Ile Ser Gly Lys His Phe Tyr Phe Asn
705                 710                 715                 720

Thr Asp Gly Ile Met Gln Ile Gly Val Phe Lys Gly Pro Asp Gly Phe
                725                 730                 735

Glu Tyr Phe Ala Pro Ala Asn Thr Asp Ala Asn Asn Ile Glu Gly Gln
            740                 745                 750

Ala Ile Arg Tyr Gln Asn Arg Phe Leu Tyr Leu His Asp Asn Ile Tyr
        755                 760                 765

Tyr Phe Gly Asn Asp Ser Lys Ala Ala Thr Gly Trp Ala Thr Ile Asp
    770                 775                 780

Gly Asn Arg Tyr Tyr Phe Glu Pro Asn Thr Ala Met Gly Ala Asn Gly
785                 790                 795                 800

Tyr Lys Thr Ile Asp Asn Lys Asn Phe Tyr Phe Arg Asn Gly Leu Pro
                805                 810                 815

Gln Ile Gly Val Phe Lys Gly Pro Asn Gly Phe Glu Tyr Phe Ala Pro
            820                 825                 830

Ala Asn Thr Asp Ala Asn Asn Ile Asp Gly Gln Ala Ile Arg Tyr Gln
        835                 840                 845

Asn Arg Phe Leu His Leu Leu Gly Lys Ile Tyr Tyr Phe Gly Asn Asn
    850                 855                 860

Ser Lys Ala Val Thr Gly Trp Gln Thr Ile Asn Ser Lys Val Tyr Tyr
865                 870                 875                 880

Phe Met Pro Asp Thr Ala Met Ala Ala Ala Gly Gly Leu Phe Glu Ile
                885                 890                 895

Asp Gly Val Ile Tyr Phe Phe Gly Val Asp Gly Val Lys Ala Pro Gly
            900                 905                 910

Ile Tyr Gly Leu Glu
        915
```

<210> SEQ ID NO 23
<211> LENGTH: 2868
<212> TYPE: DNA
<213> ORGANISM: Artificial sequence
<220> FEATURE:
<223> OTHER INFORMATION: Synthetic polynucleotide
<220> FEATURE:
<221> NAME/KEY: CDS
<222> LOCATION: (1)..(2868)

<400> SEQUENCE: 23

```
cat atg aaa aaa tta ttg att gcc gca atg atg gcg gct gcc ttg gca       48
His Met Lys Lys Leu Leu Ile Ala Ala Met Met Ala Ala Ala Leu Ala
1               5                   10                  15

gct tgt tcg caa gaa gcc aaa cag gag gtt aag gaa gcg gtt caa gcc       96
Ala Cys Ser Gln Glu Ala Lys Gln Glu Val Lys Glu Ala Val Gln Ala
            20                  25                  30

gtt gag tcc gat gtt aaa gac act gcg gga tcc ttt aat agc gag aat      144
Val Glu Ser Asp Val Lys Asp Thr Ala Gly Ser Phe Asn Ser Glu Asn
        35                  40                  45

gaa ctg gat cgt gat cat ctg ggc ttc aaa atc atc gat aat aaa acc      192
Glu Leu Asp Arg Asp His Leu Gly Phe Lys Ile Ile Asp Asn Lys Thr
    50                  55                  60

tat tat tat gat gaa gat agc aaa ctg gtg aaa ggc ctg att aac att      240
Tyr Tyr Tyr Asp Glu Asp Ser Lys Leu Val Lys Gly Leu Ile Asn Ile
65                  70                  75                  80

aac aac agc ctg ttt tac ttc gat ccg att gaa agc aat ctg gtt acc      288
Asn Asn Ser Leu Phe Tyr Phe Asp Pro Ile Glu Ser Asn Leu Val Thr
                85                  90                  95

ggt tgg cag acc att aac ggc aaa aaa tat tat ttt gat att aat acc      336
Gly Trp Gln Thr Ile Asn Gly Lys Lys Tyr Tyr Phe Asp Ile Asn Thr
            100                 105                 110

ggt gca gcc agc acc agc tat aaa att atc aac ggc aag cat ttc tat      384
Gly Ala Ala Ser Thr Ser Tyr Lys Ile Ile Asn Gly Lys His Phe Tyr
        115                 120                 125

ttc aat aat aat ggc gtg atg cag ctg ggc gtt ttt aaa ggt ccg gat      432
Phe Asn Asn Asn Gly Val Met Gln Leu Gly Val Phe Lys Gly Pro Asp
    130                 135                 140

ggt ttt gaa tat ttt gca ccg gca aat acc cag aac aat aat att gaa      480
Gly Phe Glu Tyr Phe Ala Pro Ala Asn Thr Gln Asn Asn Asn Ile Glu
145                 150                 155                 160

ggt cag gcc att gtg tat cag agc aaa ttt ctg acc ctg aac ggt aaa      528
Gly Gln Ala Ile Val Tyr Gln Ser Lys Phe Leu Thr Leu Asn Gly Lys
                165                 170                 175

aaa tac tac ttc gac aac gat agc aaa gca gtg acc ggt tgg cgc att      576
Lys Tyr Tyr Phe Asp Asn Asp Ser Lys Ala Val Thr Gly Trp Arg Ile
            180                 185                 190

att aac aac gag aaa tat tat ttc aat ccg aat aac gcc att gca gca      624
Ile Asn Asn Glu Lys Tyr Tyr Phe Asn Pro Asn Asn Ala Ile Ala Ala
        195                 200                 205

gtt ggt ctg cag gtt att gac aac aat aaa tat tac ttt aac ccg gac      672
Val Gly Leu Gln Val Ile Asp Asn Asn Lys Tyr Tyr Phe Asn Pro Asp
    210                 215                 220

acc gcc att att agc aaa ggc tgg cag acc gtt aat ggt agc cgt tat      720
Thr Ala Ile Ile Ser Lys Gly Trp Gln Thr Val Asn Gly Ser Arg Tyr
225                 230                 235                 240

tat ttc gat acc gat acc gcg att gcc ttt aat ggc tat aaa acc atc      768
Tyr Phe Asp Thr Asp Thr Ala Ile Ala Phe Asn Gly Tyr Lys Thr Ile
                245                 250                 255

gac ggc aaa cac ttc tat ttt gat agc gat tgc gtg gtg aaa att ggt      816
Asp Gly Lys His Phe Tyr Phe Asp Ser Asp Cys Val Val Lys Ile Gly
            260                 265                 270
```

-continued

```
gtt ttt agc ggt agc aac ggc ttt gaa tac ttt gcc cct gcc aat acc      864
Val Phe Ser Gly Ser Asn Gly Phe Glu Tyr Phe Ala Pro Ala Asn Thr
        275                 280                 285

tac aac aac aac atc gaa ggc cag gca atc gtt tat cag tca aaa ttc      912
Tyr Asn Asn Asn Ile Glu Gly Gln Ala Ile Val Tyr Gln Ser Lys Phe
    290                 295                 300

ctg acg ctg aat ggg aaa aaa tat tac ttt gac aat aac agc aaa gcc      960
Leu Thr Leu Asn Gly Lys Lys Tyr Tyr Phe Asp Asn Asn Ser Lys Ala
305                 310                 315                 320

gtt acg gga tgg cag aca att gat agc aaa aaa tac tac ttc aat acc     1008
Val Thr Gly Trp Gln Thr Ile Asp Ser Lys Lys Tyr Tyr Phe Asn Thr
                325                 330                 335

aat acc gca gaa gca gca aca ggt tgg cag acg atc gat ggt aaa aaa     1056
Asn Thr Ala Glu Ala Ala Thr Gly Trp Gln Thr Ile Asp Gly Lys Lys
            340                 345                 350

tat tat ttc aac acg aac aca gcc gaa gca gcc acc ggc tgg caa acc     1104
Tyr Tyr Phe Asn Thr Asn Thr Ala Glu Ala Ala Thr Gly Trp Gln Thr
        355                 360                 365

att gat gga aaa aaa tat tac ttc aat aca aat acg agc att gcc agc     1152
Ile Asp Gly Lys Lys Tyr Tyr Phe Asn Thr Asn Thr Ser Ile Ala Ser
    370                 375                 380

acc ggt tat acc att atc aac ggc aaa tat ttc tac ttc aac acc gat     1200
Thr Gly Tyr Thr Ile Ile Asn Gly Lys Tyr Phe Tyr Phe Asn Thr Asp
385                 390                 395                 400

ggc att atg cag att ggt gtg ttc aaa gtg ccg aat ggc ttt gag tat     1248
Gly Ile Met Gln Ile Gly Val Phe Lys Val Pro Asn Gly Phe Glu Tyr
                405                 410                 415

ttc gct ccg gct aac acc cat aat aac aat att gag ggc cag gcg atc     1296
Phe Ala Pro Ala Asn Thr His Asn Asn Asn Ile Glu Gly Gln Ala Ile
            420                 425                 430

ctg tat cag aat aaa ttc ctg aca ctg aac ggc aaa aaa tac tat ttc     1344
Leu Tyr Gln Asn Lys Phe Leu Thr Leu Asn Gly Lys Lys Tyr Tyr Phe
        435                 440                 445

ggc agc gat tca aaa gca att aca ggt tgg caa aca att gac ggg aaa     1392
Gly Ser Asp Ser Lys Ala Ile Thr Gly Trp Gln Thr Ile Asp Gly Lys
    450                 455                 460

aag tac tat ttt aat ccg aac aat gcg atc gca gca acc cat ctg tgt     1440
Lys Tyr Tyr Phe Asn Pro Asn Asn Ala Ile Ala Ala Thr His Leu Cys
465                 470                 475                 480

acc att aat aac gat aaa tac tac ttt agc tat gac ggc atc ctg cag     1488
Thr Ile Asn Asn Asp Lys Tyr Tyr Phe Ser Tyr Asp Gly Ile Leu Gln
                485                 490                 495

aat ggc tat atc acc att gaa cgc aac aac ttt tac ttt gat gcc aac     1536
Asn Gly Tyr Ile Thr Ile Glu Arg Asn Asn Phe Tyr Phe Asp Ala Asn
            500                 505                 510

aac gaa agc aaa atg gtg acc ggt gtt ttt aaa ggc cct aat ggc ttc     1584
Asn Glu Ser Lys Met Val Thr Gly Val Phe Lys Gly Pro Asn Gly Phe
        515                 520                 525

gaa tac ttc gca cca gcg aat acg cat aac aat aac atc gag ggt caa     1632
Glu Tyr Phe Ala Pro Ala Asn Thr His Asn Asn Asn Ile Glu Gly Gln
    530                 535                 540

gcg att gtc tac cag aat aaa ttt ctg act ctg aat ggt aaa aaa tat     1680
Ala Ile Val Tyr Gln Asn Lys Phe Leu Thr Leu Asn Gly Lys Lys Tyr
545                 550                 555                 560

tac ttc gat aat gat tca aaa gcc gtg acc gga tgg caa act atc gat     1728
Tyr Phe Asp Asn Asp Ser Lys Ala Val Thr Gly Trp Gln Thr Ile Asp
                565                 570                 575

tca aaa aaa tac tac ttt aac ctg aac acc gca gtt gca gtt aca ggg     1776
Ser Lys Lys Tyr Tyr Phe Asn Leu Asn Thr Ala Val Ala Val Thr Gly
```

```
            580                 585                 590

tgg caa acc atc gac ggt gag aaa tac tac ttc aat ctg aat aca gcc      1824
Trp Gln Thr Ile Asp Gly Glu Lys Tyr Tyr Phe Asn Leu Asn Thr Ala
        595                 600                 605

gaa gcc gct act gga tgg cag acg att gac gga aaa cgc tat tat ttt      1872
Glu Ala Ala Thr Gly Trp Gln Thr Ile Asp Gly Lys Arg Tyr Tyr Phe
    610                 615                 620

aat acc aac acc tat att gcg agc aca ggc tat acc atc att aat ggt      1920
Asn Thr Asn Thr Tyr Ile Ala Ser Thr Gly Tyr Thr Ile Ile Asn Gly
625                 630                 635                 640

aaa cac ttc tac ttt aac acg gac ggt atc atg caa atc ggc gtg ttt      1968
Lys His Phe Tyr Phe Asn Thr Asp Gly Ile Met Gln Ile Gly Val Phe
                645                 650                 655

aaa ggc cca gac ggt ttc gag tac ttt gcg cca gca aac acc cac aat      2016
Lys Gly Pro Asp Gly Phe Glu Tyr Phe Ala Pro Ala Asn Thr His Asn
            660                 665                 670

aat aac atc gaa gga caa gcc atc ctg tat caa aac aaa ttt ctg acg      2064
Asn Asn Ile Glu Gly Gln Ala Ile Leu Tyr Gln Asn Lys Phe Leu Thr
        675                 680                 685

ctg aat ggc aaa aaa tac tac ttc ggt agt gat agc aaa gct gtt aca      2112
Leu Asn Gly Lys Lys Tyr Tyr Phe Gly Ser Asp Ser Lys Ala Val Thr
    690                 695                 700

ggt ctg cgt acc atc gac gga aaa aaa tat tac ttt aat act aac acg      2160
Gly Leu Arg Thr Ile Asp Gly Lys Lys Tyr Tyr Phe Asn Thr Asn Thr
705                 710                 715                 720

gca gtg gca gtg acg ggc tgg caa acg atc aac ggg aaa aaa tac tac      2208
Ala Val Ala Val Thr Gly Trp Gln Thr Ile Asn Gly Lys Lys Tyr Tyr
                725                 730                 735

ttc aac acc aac acg tat att gcc tca acc ggc tat aca att atc agc      2256
Phe Asn Thr Asn Thr Tyr Ile Ala Ser Thr Gly Tyr Thr Ile Ile Ser
            740                 745                 750

ggt aaa cac ttt tat ttc aat aca gat ggg atc atg cag atc gga gtt      2304
Gly Lys His Phe Tyr Phe Asn Thr Asp Gly Ile Met Gln Ile Gly Val
        755                 760                 765

ttc aaa gga cct gat gga ttc gag tat ttt gct cct gcg aat acc gat      2352
Phe Lys Gly Pro Asp Gly Phe Glu Tyr Phe Ala Pro Ala Asn Thr Asp
    770                 775                 780

gcc aat aac att gag gga cag gca att cgc tat cag aat cgt ttt ctg      2400
Ala Asn Asn Ile Glu Gly Gln Ala Ile Arg Tyr Gln Asn Arg Phe Leu
785                 790                 795                 800

tat ctg cac gat aat att tat tat ttt ggc aat gat tcc aaa gcg gca      2448
Tyr Leu His Asp Asn Ile Tyr Tyr Phe Gly Asn Asp Ser Lys Ala Ala
                805                 810                 815

acc ggt tgg gcc acc att gat ggt aat cgt tat tat ttt gag ccg aat      2496
Thr Gly Trp Ala Thr Ile Asp Gly Asn Arg Tyr Tyr Phe Glu Pro Asn
            820                 825                 830

acc gca atg ggt gcc aat ggt tat aaa acg att gat aac aaa aac ttt      2544
Thr Ala Met Gly Ala Asn Gly Tyr Lys Thr Ile Asp Asn Lys Asn Phe
        835                 840                 845

tat ttt cgc aac ggc ctg ccg cag att ggc gta ttc aaa ggt cct aac      2592
Tyr Phe Arg Asn Gly Leu Pro Gln Ile Gly Val Phe Lys Gly Pro Asn
    850                 855                 860

ggt ttt gag tac ttc gct cca gcc aat aca gat gca aat aat atc gac      2640
Gly Phe Glu Tyr Phe Ala Pro Ala Asn Thr Asp Ala Asn Asn Ile Asp
865                 870                 875                 880

ggc cag gcc atc cgc tac cag aac cgc ttc ctg cat ctg ctg ggt aaa      2688
Gly Gln Ala Ile Arg Tyr Gln Asn Arg Phe Leu His Leu Leu Gly Lys
                885                 890                 895

atc tat tat ttc ggc aac aac agc aaa gcg gta act ggt tgg caa acc      2736
```

-continued

```
Ile Tyr Tyr Phe Gly Asn Asn Ser Lys Ala Val Thr Gly Trp Gln Thr
            900                 905                 910

atc aat agc aaa gtg tat tat ttc atg ccg gat aca gca atg gca gca      2784
Ile Asn Ser Lys Val Tyr Tyr Phe Met Pro Asp Thr Ala Met Ala Ala
        915                 920                 925

gcc ggt ggt ctg ttt gaa att gat ggt gtg atc tat ttc ttt ggt gtg      2832
Ala Gly Gly Leu Phe Glu Ile Asp Gly Val Ile Tyr Phe Phe Gly Val
    930                 935                 940

gat ggt gtt aaa gca ccg ggt att tat ggc ctc gag                      2868
Asp Gly Val Lys Ala Pro Gly Ile Tyr Gly Leu Glu
945                 950                 955


<210> SEQ ID NO 24
<211> LENGTH: 956
<212> TYPE: PRT
<213> ORGANISM: Artificial sequence
<220> FEATURE:
<223> OTHER INFORMATION: Synthetic Construct

<400> SEQUENCE: 24

His Met Lys Lys Leu Leu Ile Ala Ala Met Met Ala Ala Ala Leu Ala
1               5                   10                  15

Ala Cys Ser Gln Glu Ala Lys Gln Glu Val Lys Glu Ala Val Gln Ala
            20                  25                  30

Val Glu Ser Asp Val Lys Asp Thr Ala Gly Ser Phe Asn Ser Glu Asn
        35                  40                  45

Glu Leu Asp Arg Asp His Leu Gly Phe Lys Ile Ile Asp Asn Lys Thr
    50                  55                  60

Tyr Tyr Tyr Asp Glu Asp Ser Lys Leu Val Lys Gly Leu Ile Asn Ile
65                  70                  75                  80

Asn Asn Ser Leu Phe Tyr Phe Asp Pro Ile Glu Ser Asn Leu Val Thr
                85                  90                  95

Gly Trp Gln Thr Ile Asn Gly Lys Lys Tyr Tyr Phe Asp Ile Asn Thr
            100                 105                 110

Gly Ala Ala Ser Thr Ser Tyr Lys Ile Ile Asn Gly Lys His Phe Tyr
        115                 120                 125

Phe Asn Asn Asn Gly Val Met Gln Leu Gly Val Phe Lys Gly Pro Asp
    130                 135                 140

Gly Phe Glu Tyr Phe Ala Pro Ala Asn Thr Gln Asn Asn Asn Ile Glu
145                 150                 155                 160

Gly Gln Ala Ile Val Tyr Gln Ser Lys Phe Leu Thr Leu Asn Gly Lys
                165                 170                 175

Lys Tyr Tyr Phe Asp Asn Asp Ser Lys Ala Val Thr Gly Trp Arg Ile
            180                 185                 190

Ile Asn Asn Glu Lys Tyr Tyr Phe Asn Pro Asn Asn Ala Ile Ala Ala
        195                 200                 205

Val Gly Leu Gln Val Ile Asp Asn Asn Lys Tyr Tyr Phe Asn Pro Asp
    210                 215                 220

Thr Ala Ile Ile Ser Lys Gly Trp Gln Thr Val Asn Gly Ser Arg Tyr
225                 230                 235                 240

Tyr Phe Asp Thr Asp Thr Ala Ile Ala Phe Asn Gly Tyr Lys Thr Ile
                245                 250                 255

Asp Gly Lys His Phe Tyr Phe Asp Ser Asp Cys Val Val Lys Ile Gly
            260                 265                 270

Val Phe Ser Gly Ser Asn Gly Phe Glu Tyr Phe Ala Pro Ala Asn Thr
        275                 280                 285
```

```
Tyr Asn Asn Asn Ile Glu Gly Gln Ala Ile Val Tyr Gln Ser Lys Phe
    290                 295                 300

Leu Thr Leu Asn Gly Lys Lys Tyr Tyr Phe Asp Asn Asn Ser Lys Ala
305                 310                 315                 320

Val Thr Gly Trp Gln Thr Ile Asp Ser Lys Lys Tyr Tyr Phe Asn Thr
                325                 330                 335

Asn Thr Ala Glu Ala Ala Thr Gly Trp Gln Thr Ile Asp Gly Lys Lys
            340                 345                 350

Tyr Tyr Phe Asn Thr Asn Thr Ala Glu Ala Ala Thr Gly Trp Gln Thr
        355                 360                 365

Ile Asp Gly Lys Lys Tyr Tyr Phe Asn Thr Asn Thr Ser Ile Ala Ser
    370                 375                 380

Thr Gly Tyr Thr Ile Ile Asn Gly Lys Tyr Phe Tyr Phe Asn Thr Asp
385                 390                 395                 400

Gly Ile Met Gln Ile Gly Val Phe Lys Val Pro Asn Gly Phe Glu Tyr
                405                 410                 415

Phe Ala Pro Ala Asn Thr His Asn Asn Asn Ile Glu Gly Gln Ala Ile
            420                 425                 430

Leu Tyr Gln Asn Lys Phe Leu Thr Leu Asn Gly Lys Lys Tyr Tyr Phe
        435                 440                 445

Gly Ser Asp Ser Lys Ala Ile Thr Gly Trp Gln Thr Ile Asp Gly Lys
    450                 455                 460

Lys Tyr Tyr Phe Asn Pro Asn Asn Ala Ile Ala Ala Thr His Leu Cys
465                 470                 475                 480

Thr Ile Asn Asn Asp Lys Tyr Tyr Phe Ser Tyr Asp Gly Ile Leu Gln
                485                 490                 495

Asn Gly Tyr Ile Thr Ile Glu Arg Asn Asn Phe Tyr Phe Asp Ala Asn
            500                 505                 510

Asn Glu Ser Lys Met Val Thr Gly Val Phe Lys Gly Pro Asn Gly Phe
        515                 520                 525

Glu Tyr Phe Ala Pro Ala Asn Thr His Asn Asn Asn Ile Glu Gly Gln
    530                 535                 540

Ala Ile Val Tyr Gln Asn Lys Phe Leu Thr Leu Asn Gly Lys Lys Tyr
545                 550                 555                 560

Tyr Phe Asp Asn Asp Ser Lys Ala Val Thr Gly Trp Gln Thr Ile Asp
                565                 570                 575

Ser Lys Lys Tyr Tyr Phe Asn Leu Asn Thr Ala Val Ala Val Thr Gly
            580                 585                 590

Trp Gln Thr Ile Asp Gly Glu Lys Tyr Tyr Phe Asn Leu Asn Thr Ala
        595                 600                 605

Glu Ala Ala Thr Gly Trp Gln Thr Ile Asp Gly Lys Arg Tyr Tyr Phe
    610                 615                 620

Asn Thr Asn Thr Tyr Ile Ala Ser Thr Gly Tyr Thr Ile Ile Asn Gly
625                 630                 635                 640

Lys His Phe Tyr Phe Asn Thr Asp Gly Ile Met Gln Ile Gly Val Phe
                645                 650                 655

Lys Gly Pro Asp Gly Phe Glu Tyr Phe Ala Pro Ala Asn Thr His Asn
            660                 665                 670

Asn Asn Ile Glu Gly Gln Ala Ile Leu Tyr Gln Asn Lys Phe Leu Thr
        675                 680                 685

Leu Asn Gly Lys Lys Tyr Tyr Phe Gly Ser Asp Ser Lys Ala Val Thr
    690                 695                 700

Gly Leu Arg Thr Ile Asp Gly Lys Lys Tyr Tyr Phe Asn Thr Asn Thr
```

```
705                 710                 715                 720

Ala Val Ala Val Thr Gly Trp Gln Thr Ile Asn Gly Lys Lys Tyr Tyr
                725                 730                 735

Phe Asn Thr Asn Thr Tyr Ile Ala Ser Thr Gly Tyr Thr Ile Ile Ser
            740                 745                 750

Gly Lys His Phe Tyr Phe Asn Thr Asp Gly Ile Met Gln Ile Gly Val
        755                 760                 765

Phe Lys Gly Pro Asp Gly Phe Glu Tyr Phe Ala Pro Ala Asn Thr Asp
    770                 775                 780

Ala Asn Asn Ile Glu Gly Gln Ala Ile Arg Tyr Gln Asn Arg Phe Leu
785                 790                 795                 800

Tyr Leu His Asp Asn Ile Tyr Tyr Phe Gly Asn Asp Ser Lys Ala Ala
                805                 810                 815

Thr Gly Trp Ala Thr Ile Asp Gly Asn Arg Tyr Tyr Phe Glu Pro Asn
            820                 825                 830

Thr Ala Met Gly Ala Asn Gly Tyr Lys Thr Ile Asp Asn Lys Asn Phe
        835                 840                 845

Tyr Phe Arg Asn Gly Leu Pro Gln Ile Gly Val Phe Lys Gly Pro Asn
    850                 855                 860

Gly Phe Glu Tyr Phe Ala Pro Ala Asn Thr Asp Ala Asn Asn Ile Asp
865                 870                 875                 880

Gly Gln Ala Ile Arg Tyr Gln Asn Arg Phe Leu His Leu Leu Gly Lys
                885                 890                 895

Ile Tyr Tyr Phe Gly Asn Asn Ser Lys Ala Val Thr Gly Trp Gln Thr
            900                 905                 910

Ile Asn Ser Lys Val Tyr Tyr Phe Met Pro Asp Thr Ala Met Ala Ala
        915                 920                 925

Ala Gly Gly Leu Phe Glu Ile Asp Gly Val Ile Tyr Phe Phe Gly Val
    930                 935                 940

Asp Gly Val Lys Ala Pro Gly Ile Tyr Gly Leu Glu
945                 950                 955


<210> SEQ ID NO 25
<211> LENGTH: 1251
<212> TYPE: DNA
<213> ORGANISM: Artificial sequence
<220> FEATURE:
<223> OTHER INFORMATION: Synthetic polynucleotide
<220> FEATURE:
<221> NAME/KEY: CDS
<222> LOCATION: (1)..(1251)

<400> SEQUENCE: 25

cat atg gga tcc ttt aat agc gag aat gaa ctg gat cgt gat cat ctg       48
His Met Gly Ser Phe Asn Ser Glu Asn Glu Leu Asp Arg Asp His Leu
1               5                   10                  15

ggc ttc aaa atc atc gat aat aaa acc tat tat tat gat gaa gat agc       96
Gly Phe Lys Ile Ile Asp Asn Lys Thr Tyr Tyr Tyr Asp Glu Asp Ser
            20                  25                  30

aaa ctg gtg aaa ggc ctg att aac att aac aac agc ctg ttt tac ttc      144
Lys Leu Val Lys Gly Leu Ile Asn Ile Asn Asn Ser Leu Phe Tyr Phe
        35                  40                  45

gat ccg att gaa agc aat ctg gtt acc ggt tgg cag acc att aac ggc      192
Asp Pro Ile Glu Ser Asn Leu Val Thr Gly Trp Gln Thr Ile Asn Gly
    50                  55                  60

aaa aaa tat tat ttt gat att aat acc ggt gca gcc agc acc agc tat      240
Lys Lys Tyr Tyr Phe Asp Ile Asn Thr Gly Ala Ala Ser Thr Ser Tyr
65                  70                  75                  80
```

```
aaa att atc aac ggc aag cat ttc tat ttc aat aat aat ggc gtg atg      288
Lys Ile Ile Asn Gly Lys His Phe Tyr Phe Asn Asn Asn Gly Val Met
                85                  90                  95

cag ctg ggc gtt ttt aaa ggt ccg gat ggt ttt gaa tat ttt gca ccg      336
Gln Leu Gly Val Phe Lys Gly Pro Asp Gly Phe Glu Tyr Phe Ala Pro
            100                 105                 110

gca aat acc cag aac aat aat att gaa ggt cag gcc att gtg tat cag      384
Ala Asn Thr Gln Asn Asn Asn Ile Glu Gly Gln Ala Ile Val Tyr Gln
        115                 120                 125

agc aaa ttt ctg acc ctg aac ggt aaa aaa tac tac ttc gac aac gat      432
Ser Lys Phe Leu Thr Leu Asn Gly Lys Lys Tyr Tyr Phe Asp Asn Asp
    130                 135                 140

agc aaa gca gtg acc ggt tgg cgc att att aac aac gag aaa tat tat      480
Ser Lys Ala Val Thr Gly Trp Arg Ile Ile Asn Asn Glu Lys Tyr Tyr
145                 150                 155                 160

ttc aat ccg aat aac gcc att gca gca gtt ggt ctg cag gtt att gac      528
Phe Asn Pro Asn Asn Ala Ile Ala Ala Val Gly Leu Gln Val Ile Asp
                165                 170                 175

aac aat aaa tat tac ttt aac ccg gac acc gcc att att agc aaa ggc      576
Asn Asn Lys Tyr Tyr Phe Asn Pro Asp Thr Ala Ile Ile Ser Lys Gly
            180                 185                 190

tgg cag acc gtt aat ggt agc cgt tat tat ttc gat acc gat acc gcg      624
Trp Gln Thr Val Asn Gly Ser Arg Tyr Tyr Phe Asp Thr Asp Thr Ala
        195                 200                 205

att gcc ttt aat ggc tat aaa acc atc gac ggc aaa cac ttc tat ttt      672
Ile Ala Phe Asn Gly Tyr Lys Thr Ile Asp Gly Lys His Phe Tyr Phe
    210                 215                 220

gat agc gat tgc gtg gtg aaa att ggt gtt ttt agc ggt agc aac ggc      720
Asp Ser Asp Cys Val Val Lys Ile Gly Val Phe Ser Gly Ser Asn Gly
225                 230                 235                 240

ttt gaa tac ttt gcc cct gcc aat acc tac aac aac aac atc gaa ggc      768
Phe Glu Tyr Phe Ala Pro Ala Asn Thr Tyr Asn Asn Asn Ile Glu Gly
                245                 250                 255

cag gca atc gtt tat cag tca aaa ttc ctg acg ctg aat ggg aaa aaa      816
Gln Ala Ile Val Tyr Gln Ser Lys Phe Leu Thr Leu Asn Gly Lys Lys
            260                 265                 270

tat tac ttt gac aat aac agc aaa gcc gtt acg gga tgg cag aca att      864
Tyr Tyr Phe Asp Asn Asn Ser Lys Ala Val Thr Gly Trp Gln Thr Ile
        275                 280                 285

gat agc aaa aaa tac tac ttc aat acc aat acc gca gaa gca gca aca      912
Asp Ser Lys Lys Tyr Tyr Phe Asn Thr Asn Thr Ala Glu Ala Ala Thr
    290                 295                 300

ggt tgg cag acg atc gat ggt aaa aaa tat tat ttc aac acg aac aca      960
Gly Trp Gln Thr Ile Asp Gly Lys Lys Tyr Tyr Phe Asn Thr Asn Thr
305                 310                 315                 320

gcc gaa gca gcc acc ggc tgg caa acc att gat gga aaa aaa tat tac     1008
Ala Glu Ala Ala Thr Gly Trp Gln Thr Ile Asp Gly Lys Lys Tyr Tyr
                325                 330                 335

ttc aat aca aat acg agc att gcc agc acc ggt tat acc att atc aac     1056
Phe Asn Thr Asn Thr Ser Ile Ala Ser Thr Gly Tyr Thr Ile Ile Asn
            340                 345                 350

ggc aaa tat ttc tac ttc aac acc gat ggc att atg cag att ggt gtg     1104
Gly Lys Tyr Phe Tyr Phe Asn Thr Asp Gly Ile Met Gln Ile Gly Val
        355                 360                 365

ttc aaa gtg ccg aat ggc ttt gag tat ttc gct ccg gct aac acc cat     1152
Phe Lys Val Pro Asn Gly Phe Glu Tyr Phe Ala Pro Ala Asn Thr His
    370                 375                 380

aat aac aat att gag ggc cag gcg atc ctg tat cag aat aaa ttc ctg     1200
Asn Asn Asn Ile Glu Gly Gln Ala Ile Leu Tyr Gln Asn Lys Phe Leu
```

-continued

```
385                 390                 395                 400

aca ctg aac ggc aaa aaa tac tat ttc ggc agc gat tca aaa gca ctc      1248
Thr Leu Asn Gly Lys Lys Tyr Tyr Phe Gly Ser Asp Ser Lys Ala Leu
                405                 410                 415

gag                                                                  1251
Glu


<210> SEQ ID NO 26
<211> LENGTH: 417
<212> TYPE: PRT
<213> ORGANISM: Artificial sequence
<220> FEATURE:
<223> OTHER INFORMATION: Synthetic Construct

<400> SEQUENCE: 26

His Met Gly Ser Phe Asn Ser Glu Asn Glu Leu Asp Arg Asp His Leu
1               5                   10                  15

Gly Phe Lys Ile Ile Asp Asn Lys Thr Tyr Tyr Tyr Asp Glu Asp Ser
            20                  25                  30

Lys Leu Val Lys Gly Leu Ile Asn Ile Asn Asn Ser Leu Phe Tyr Phe
        35                  40                  45

Asp Pro Ile Glu Ser Asn Leu Val Thr Gly Trp Gln Thr Ile Asn Gly
    50                  55                  60

Lys Lys Tyr Tyr Phe Asp Ile Asn Thr Gly Ala Ala Ser Thr Ser Tyr
65                  70                  75                  80

Lys Ile Ile Asn Gly Lys His Phe Tyr Phe Asn Asn Asn Gly Val Met
                85                  90                  95

Gln Leu Gly Val Phe Lys Gly Pro Asp Gly Phe Glu Tyr Phe Ala Pro
            100                 105                 110

Ala Asn Thr Gln Asn Asn Asn Ile Glu Gly Gln Ala Ile Val Tyr Gln
        115                 120                 125

Ser Lys Phe Leu Thr Leu Asn Gly Lys Lys Tyr Tyr Phe Asp Asn Asp
    130                 135                 140

Ser Lys Ala Val Thr Gly Trp Arg Ile Ile Asn Asn Glu Lys Tyr Tyr
145                 150                 155                 160

Phe Asn Pro Asn Asn Ala Ile Ala Ala Val Gly Leu Gln Val Ile Asp
                165                 170                 175

Asn Asn Lys Tyr Tyr Phe Asn Pro Asp Thr Ala Ile Ile Ser Lys Gly
            180                 185                 190

Trp Gln Thr Val Asn Gly Ser Arg Tyr Tyr Phe Asp Thr Asp Thr Ala
        195                 200                 205

Ile Ala Phe Asn Gly Tyr Lys Thr Ile Asp Gly Lys His Phe Tyr Phe
    210                 215                 220

Asp Ser Asp Cys Val Val Lys Ile Gly Val Phe Ser Gly Ser Asn Gly
225                 230                 235                 240

Phe Glu Tyr Phe Ala Pro Ala Asn Thr Tyr Asn Asn Asn Ile Glu Gly
                245                 250                 255

Gln Ala Ile Val Tyr Gln Ser Lys Phe Leu Thr Leu Asn Gly Lys Lys
            260                 265                 270

Tyr Tyr Phe Asp Asn Asn Ser Lys Ala Val Thr Gly Trp Gln Thr Ile
        275                 280                 285

Asp Ser Lys Lys Tyr Tyr Phe Asn Thr Asn Thr Ala Glu Ala Ala Thr
    290                 295                 300

Gly Trp Gln Thr Ile Asp Gly Lys Lys Tyr Tyr Phe Asn Thr Asn Thr
305                 310                 315                 320
```

```
Ala Glu Ala Ala Thr Gly Trp Gln Thr Ile Asp Gly Lys Lys Tyr Tyr
                325                 330                 335

Phe Asn Thr Asn Thr Ser Ile Ala Ser Thr Gly Tyr Thr Ile Ile Asn
            340                 345                 350

Gly Lys Tyr Phe Tyr Phe Asn Thr Asp Gly Ile Met Gln Ile Gly Val
        355                 360                 365

Phe Lys Val Pro Asn Gly Phe Glu Tyr Phe Ala Pro Ala Asn Thr His
    370                 375                 380

Asn Asn Asn Ile Glu Gly Gln Ala Ile Leu Tyr Gln Asn Lys Phe Leu
385                 390                 395                 400

Thr Leu Asn Gly Lys Lys Tyr Tyr Phe Gly Ser Asp Ser Lys Ala Leu
                405                 410                 415

Glu


<210> SEQ ID NO 27
<211> LENGTH: 1368
<212> TYPE: DNA
<213> ORGANISM: Artificial sequence
<220> FEATURE:
<223> OTHER INFORMATION: Synthetic polynucleotide
<220> FEATURE:
<221> NAME/KEY: CDS
<222> LOCATION: (1)..(1368)

<400> SEQUENCE: 27

cat atg aaa aaa tta ttg att gcc gca atg atg gcg gct gcc ttg gca       48
His Met Lys Lys Leu Leu Ile Ala Ala Met Met Ala Ala Ala Leu Ala
1               5                   10                  15

gct tgt tcg caa gaa gcc aaa cag gag gtt aag gaa gcg gtt caa gcc       96
Ala Cys Ser Gln Glu Ala Lys Gln Glu Val Lys Glu Ala Val Gln Ala
            20                  25                  30

gtt gag tcc gat gtt aaa gac act gcg gga tcc ttt aat agc gag aat      144
Val Glu Ser Asp Val Lys Asp Thr Ala Gly Ser Phe Asn Ser Glu Asn
        35                  40                  45

gaa ctg gat cgt gat cat ctg ggc ttc aaa atc atc gat aat aaa acc      192
Glu Leu Asp Arg Asp His Leu Gly Phe Lys Ile Ile Asp Asn Lys Thr
    50                  55                  60

tat tat tat gat gaa gat agc aaa ctg gtg aaa ggc ctg att aac att      240
Tyr Tyr Tyr Asp Glu Asp Ser Lys Leu Val Lys Gly Leu Ile Asn Ile
65                  70                  75                  80

aac aac agc ctg ttt tac ttc gat ccg att gaa agc aat ctg gtt acc      288
Asn Asn Ser Leu Phe Tyr Phe Asp Pro Ile Glu Ser Asn Leu Val Thr
                85                  90                  95

ggt tgg cag acc att aac ggc aaa aaa tat tat ttt gat att aat acc      336
Gly Trp Gln Thr Ile Asn Gly Lys Lys Tyr Tyr Phe Asp Ile Asn Thr
            100                 105                 110

ggt gca gcc agc acc agc tat aaa att atc aac ggc aag cat ttc tat      384
Gly Ala Ala Ser Thr Ser Tyr Lys Ile Ile Asn Gly Lys His Phe Tyr
        115                 120                 125

ttc aat aat aat ggc gtg atg cag ctg ggc gtt ttt aaa ggt ccg gat      432
Phe Asn Asn Asn Gly Val Met Gln Leu Gly Val Phe Lys Gly Pro Asp
    130                 135                 140

ggt ttt gaa tat ttt gca ccg gca aat acc cag aac aat aat att gaa      480
Gly Phe Glu Tyr Phe Ala Pro Ala Asn Thr Gln Asn Asn Asn Ile Glu
145                 150                 155                 160

ggt cag gcc att gtg tat cag agc aaa ttt ctg acc ctg aac ggt aaa      528
Gly Gln Ala Ile Val Tyr Gln Ser Lys Phe Leu Thr Leu Asn Gly Lys
                165                 170                 175

aaa tac tac ttc gac aac gat agc aaa gca gtg acc ggt tgg cgc att      576
Lys Tyr Tyr Phe Asp Asn Asp Ser Lys Ala Val Thr Gly Trp Arg Ile
```

```
            180                 185                 190

att aac aac gag aaa tat tat ttc aat ccg aat aac gcc att gca gca      624
Ile Asn Asn Glu Lys Tyr Tyr Phe Asn Pro Asn Asn Ala Ile Ala Ala
        195                 200                 205

gtt ggt ctg cag gtt att gac aac aat aaa tat tac ttt aac ccg gac      672
Val Gly Leu Gln Val Ile Asp Asn Asn Lys Tyr Tyr Phe Asn Pro Asp
    210                 215                 220

acc gcc att att agc aaa ggc tgg cag acc gtt aat ggt agc cgt tat      720
Thr Ala Ile Ile Ser Lys Gly Trp Gln Thr Val Asn Gly Ser Arg Tyr
225                 230                 235                 240

tat ttc gat acc gat acc gcg att gcc ttt aat ggc tat aaa acc atc      768
Tyr Phe Asp Thr Asp Thr Ala Ile Ala Phe Asn Gly Tyr Lys Thr Ile
                245                 250                 255

gac ggc aaa cac ttc tat ttt gat agc gat tgc gtg gtg aaa att ggt      816
Asp Gly Lys His Phe Tyr Phe Asp Ser Asp Cys Val Val Lys Ile Gly
            260                 265                 270

gtt ttt agc ggt agc aac ggc ttt gaa tac ttt gcc cct gcc aat acc      864
Val Phe Ser Gly Ser Asn Gly Phe Glu Tyr Phe Ala Pro Ala Asn Thr
        275                 280                 285

tac aac aac aac atc gaa ggc cag gca atc gtt tat cag tca aaa ttc      912
Tyr Asn Asn Asn Ile Glu Gly Gln Ala Ile Val Tyr Gln Ser Lys Phe
    290                 295                 300

ctg acg ctg aat ggg aaa aaa tat tac ttt gac aat aac agc aaa gcc      960
Leu Thr Leu Asn Gly Lys Lys Tyr Tyr Phe Asp Asn Asn Ser Lys Ala
305                 310                 315                 320

gtt acg gga tgg cag aca att gat agc aaa aaa tac tac ttc aat acc     1008
Val Thr Gly Trp Gln Thr Ile Asp Ser Lys Lys Tyr Tyr Phe Asn Thr
                325                 330                 335

aat acc gca gaa gca gca aca ggt tgg cag acg atc gat ggt aaa aaa     1056
Asn Thr Ala Glu Ala Ala Thr Gly Trp Gln Thr Ile Asp Gly Lys Lys
            340                 345                 350

tat tat ttc aac acg aac aca gcc gaa gca gcc acc ggc tgg caa acc     1104
Tyr Tyr Phe Asn Thr Asn Thr Ala Glu Ala Ala Thr Gly Trp Gln Thr
        355                 360                 365

att gat gga aaa aaa tat tac ttc aat aca aat acg agc att gcc agc     1152
Ile Asp Gly Lys Lys Tyr Tyr Phe Asn Thr Asn Thr Ser Ile Ala Ser
    370                 375                 380

acc ggt tat acc att atc aac ggc aaa tat ttc tac ttc aac acc gat     1200
Thr Gly Tyr Thr Ile Ile Asn Gly Lys Tyr Phe Tyr Phe Asn Thr Asp
385                 390                 395                 400

ggc att atg cag att ggt gtg ttc aaa gtg ccg aat ggc ttt gag tat     1248
Gly Ile Met Gln Ile Gly Val Phe Lys Val Pro Asn Gly Phe Glu Tyr
                405                 410                 415

ttc gct ccg gct aac acc cat aat aac aat att gag ggc cag gcg atc     1296
Phe Ala Pro Ala Asn Thr His Asn Asn Asn Ile Glu Gly Gln Ala Ile
            420                 425                 430

ctg tat cag aat aaa ttc ctg aca ctg aac ggc aaa aaa tac tat ttc     1344
Leu Tyr Gln Asn Lys Phe Leu Thr Leu Asn Gly Lys Lys Tyr Tyr Phe
        435                 440                 445

ggc agc gat tca aaa gca ctc gag                                     1368
Gly Ser Asp Ser Lys Ala Leu Glu
    450                 455
```

```
<210> SEQ ID NO 28
<211> LENGTH: 456
<212> TYPE: PRT
<213> ORGANISM: Artificial sequence
<220> FEATURE:
<223> OTHER INFORMATION: Synthetic Construct

<400> SEQUENCE: 28
```

-continued

```
His Met Lys Lys Leu Leu Ile Ala Ala Met Met Ala Ala Ala Leu Ala
1               5                   10                  15

Ala Cys Ser Gln Glu Ala Lys Gln Glu Val Lys Glu Ala Val Gln Ala
            20                  25                  30

Val Glu Ser Asp Val Lys Asp Thr Ala Gly Ser Phe Asn Ser Glu Asn
        35                  40                  45

Glu Leu Asp Arg Asp His Leu Gly Phe Lys Ile Ile Asp Asn Lys Thr
    50                  55                  60

Tyr Tyr Tyr Asp Glu Asp Ser Lys Leu Val Lys Gly Leu Ile Asn Ile
65                  70                  75                  80

Asn Asn Ser Leu Phe Tyr Phe Asp Pro Ile Glu Ser Asn Leu Val Thr
                85                  90                  95

Gly Trp Gln Thr Ile Asn Gly Lys Lys Tyr Tyr Phe Asp Ile Asn Thr
            100                 105                 110

Gly Ala Ala Ser Thr Ser Tyr Lys Ile Ile Asn Gly Lys His Phe Tyr
        115                 120                 125

Phe Asn Asn Asn Gly Val Met Gln Leu Gly Val Phe Lys Gly Pro Asp
    130                 135                 140

Gly Phe Glu Tyr Phe Ala Pro Ala Asn Thr Gln Asn Asn Asn Ile Glu
145                 150                 155                 160

Gly Gln Ala Ile Val Tyr Gln Ser Lys Phe Leu Thr Leu Asn Gly Lys
                165                 170                 175

Lys Tyr Tyr Phe Asp Asn Asp Ser Lys Ala Val Thr Gly Trp Arg Ile
            180                 185                 190

Ile Asn Asn Glu Lys Tyr Tyr Phe Asn Pro Asn Asn Ala Ile Ala Ala
        195                 200                 205

Val Gly Leu Gln Val Ile Asp Asn Asn Lys Tyr Tyr Phe Asn Pro Asp
    210                 215                 220

Thr Ala Ile Ile Ser Lys Gly Trp Gln Thr Val Asn Gly Ser Arg Tyr
225                 230                 235                 240

Tyr Phe Asp Thr Asp Thr Ala Ile Ala Phe Asn Gly Tyr Lys Thr Ile
                245                 250                 255

Asp Gly Lys His Phe Tyr Phe Asp Ser Asp Cys Val Val Lys Ile Gly
            260                 265                 270

Val Phe Ser Gly Ser Asn Gly Phe Glu Tyr Phe Ala Pro Ala Asn Thr
        275                 280                 285

Tyr Asn Asn Asn Ile Glu Gly Gln Ala Ile Val Tyr Gln Ser Lys Phe
    290                 295                 300

Leu Thr Leu Asn Gly Lys Lys Tyr Tyr Phe Asp Asn Asn Ser Lys Ala
305                 310                 315                 320

Val Thr Gly Trp Gln Thr Ile Asp Ser Lys Lys Tyr Tyr Phe Asn Thr
                325                 330                 335

Asn Thr Ala Glu Ala Ala Thr Gly Trp Gln Thr Ile Asp Gly Lys Lys
            340                 345                 350

Tyr Tyr Phe Asn Thr Asn Thr Ala Glu Ala Ala Thr Gly Trp Gln Thr
        355                 360                 365

Ile Asp Gly Lys Lys Tyr Tyr Phe Asn Thr Asn Thr Ser Ile Ala Ser
    370                 375                 380

Thr Gly Tyr Thr Ile Ile Asn Gly Lys Tyr Phe Tyr Phe Asn Thr Asp
385                 390                 395                 400

Gly Ile Met Gln Ile Gly Val Phe Lys Val Pro Asn Gly Phe Glu Tyr
                405                 410                 415
```

```
Phe Ala Pro Ala Asn Thr His Asn Asn Asn Ile Glu Gly Gln Ala Ile
            420                 425                 430

Leu Tyr Gln Asn Lys Phe Leu Thr Leu Asn Gly Lys Lys Tyr Tyr Phe
        435                 440                 445

Gly Ser Asp Ser Lys Ala Leu Glu
    450                 455


<210> SEQ ID NO 29
<211> LENGTH: 1173
<212> TYPE: DNA
<213> ORGANISM: Artificial sequence
<220> FEATURE:
<223> OTHER INFORMATION: Synthetic polynucleotide
<220> FEATURE:
<221> NAME/KEY: CDS
<222> LOCATION: (1)..(1173)

<400> SEQUENCE: 29

cat atg gga tcc gcc gaa gca gcc acc ggc tgg caa acc att gat gga       48
His Met Gly Ser Ala Glu Ala Ala Thr Gly Trp Gln Thr Ile Asp Gly
1               5                   10                  15

aaa aaa tat tac ttc aat aca aat acg agc att gcc agc acc ggt tat       96
Lys Lys Tyr Tyr Phe Asn Thr Asn Thr Ser Ile Ala Ser Thr Gly Tyr
            20                  25                  30

acc att atc aac ggc aaa tat ttc tac ttc aac acc gat ggc att atg      144
Thr Ile Ile Asn Gly Lys Tyr Phe Tyr Phe Asn Thr Asp Gly Ile Met
        35                  40                  45

cag att ggt gtg ttc aaa gtg ccg aat ggc ttt gag tat ttc gct ccg      192
Gln Ile Gly Val Phe Lys Val Pro Asn Gly Phe Glu Tyr Phe Ala Pro
    50                  55                  60

gct aac acc cat aat aac aat att gag ggc cag gcg atc ctg tat cag      240
Ala Asn Thr His Asn Asn Asn Ile Glu Gly Gln Ala Ile Leu Tyr Gln
65                  70                  75                  80

aat aaa ttc ctg aca ctg aac ggc aaa aaa tac tat ttc ggc agc gat      288
Asn Lys Phe Leu Thr Leu Asn Gly Lys Lys Tyr Tyr Phe Gly Ser Asp
                85                  90                  95

tca aaa gca att aca ggt tgg caa aca att gac ggg aaa aag tac tat      336
Ser Lys Ala Ile Thr Gly Trp Gln Thr Ile Asp Gly Lys Lys Tyr Tyr
            100                 105                 110

ttt aat ccg aac aat gcg atc gca gca acc cat ctg tgt acc att aat      384
Phe Asn Pro Asn Asn Ala Ile Ala Ala Thr His Leu Cys Thr Ile Asn
        115                 120                 125

aac gat aaa tac tac ttt agc tat gac ggc atc ctg cag aat ggc tat      432
Asn Asp Lys Tyr Tyr Phe Ser Tyr Asp Gly Ile Leu Gln Asn Gly Tyr
    130                 135                 140

atc acc att gaa cgc aac aac ttt tac ttt gat gcc aac aac gaa agc      480
Ile Thr Ile Glu Arg Asn Asn Phe Tyr Phe Asp Ala Asn Asn Glu Ser
145                 150                 155                 160

aaa atg gtg acc ggt gtt ttt aaa ggc cct aat ggc ttc gaa tac ttc      528
Lys Met Val Thr Gly Val Phe Lys Gly Pro Asn Gly Phe Glu Tyr Phe
                165                 170                 175

gca cca gcg aat acg cat aac aat aac atc gag ggt caa gcg att gtc      576
Ala Pro Ala Asn Thr His Asn Asn Asn Ile Glu Gly Gln Ala Ile Val
            180                 185                 190

tac cag aat aaa ttt ctg act ctg aat ggt aaa aaa tat tac ttc gat      624
Tyr Gln Asn Lys Phe Leu Thr Leu Asn Gly Lys Lys Tyr Tyr Phe Asp
        195                 200                 205

aat gat tca aaa gcc gtg acc gga tgg caa act atc gat tca aaa aaa      672
Asn Asp Ser Lys Ala Val Thr Gly Trp Gln Thr Ile Asp Ser Lys Lys
    210                 215                 220

tac tac ttt aac ctg aac acc gca gtt gca gtt aca ggg tgg caa acc      720
```

```
Tyr Tyr Phe Asn Leu Asn Thr Ala Val Ala Val Thr Gly Trp Gln Thr
225                 230                 235                 240

atc gac ggt gag aaa tac tac ttc aat ctg aat aca gcc gaa gcc gct      768
Ile Asp Gly Glu Lys Tyr Tyr Phe Asn Leu Asn Thr Ala Glu Ala Ala
                245                 250                 255

act gga tgg cag acg att gac gga aaa cgc tat tat ttt aat acc aac      816
Thr Gly Trp Gln Thr Ile Asp Gly Lys Arg Tyr Tyr Phe Asn Thr Asn
            260                 265                 270

acc tat att gcg agc aca ggc tat acc atc att aat ggt aaa cac ttc      864
Thr Tyr Ile Ala Ser Thr Gly Tyr Thr Ile Ile Asn Gly Lys His Phe
        275                 280                 285

tac ttt aac acg gac ggt atc atg caa atc ggc gtg ttt aaa ggc cca      912
Tyr Phe Asn Thr Asp Gly Ile Met Gln Ile Gly Val Phe Lys Gly Pro
    290                 295                 300

gac ggt ttc gag tac ttt gcg cca gca aac acc cac aat aat aac atc      960
Asp Gly Phe Glu Tyr Phe Ala Pro Ala Asn Thr His Asn Asn Asn Ile
305                 310                 315                 320

gaa gga caa gcc atc ctg tat caa aac aaa ttt ctg acg ctg aat ggc     1008
Glu Gly Gln Ala Ile Leu Tyr Gln Asn Lys Phe Leu Thr Leu Asn Gly
                325                 330                 335

aaa aaa tac tac ttc ggt agt gat agc aaa gct gtt aca ggt ctg cgt     1056
Lys Lys Tyr Tyr Phe Gly Ser Asp Ser Lys Ala Val Thr Gly Leu Arg
            340                 345                 350

acc atc gac gga aaa aaa tat tac ttt aat act aac acg gca gtg gca     1104
Thr Ile Asp Gly Lys Lys Tyr Tyr Phe Asn Thr Asn Thr Ala Val Ala
        355                 360                 365

gtg acg ggc tgg caa acg atc aac ggg aaa aaa tac tac ttc aac acc     1152
Val Thr Gly Trp Gln Thr Ile Asn Gly Lys Lys Tyr Tyr Phe Asn Thr
    370                 375                 380

aac acg tat att gcc ctc gag                                         1173
Asn Thr Tyr Ile Ala Leu Glu
385                 390


<210> SEQ ID NO 30
<211> LENGTH: 391
<212> TYPE: PRT
<213> ORGANISM: Artificial sequence
<220> FEATURE:
<223> OTHER INFORMATION: Synthetic Construct

<400> SEQUENCE: 30

His Met Gly Ser Ala Glu Ala Ala Thr Gly Trp Gln Thr Ile Asp Gly
1               5                   10                  15

Lys Lys Tyr Tyr Phe Asn Thr Asn Thr Ser Ile Ala Ser Thr Gly Tyr
            20                  25                  30

Thr Ile Ile Asn Gly Lys Tyr Phe Tyr Phe Asn Thr Asp Gly Ile Met
        35                  40                  45

Gln Ile Gly Val Phe Lys Val Pro Asn Gly Phe Glu Tyr Phe Ala Pro
    50                  55                  60

Ala Asn Thr His Asn Asn Asn Ile Glu Gly Gln Ala Ile Leu Tyr Gln
65                  70                  75                  80

Asn Lys Phe Leu Thr Leu Asn Gly Lys Lys Tyr Tyr Phe Gly Ser Asp
                85                  90                  95

Ser Lys Ala Ile Thr Gly Trp Gln Thr Ile Asp Gly Lys Lys Tyr Tyr
            100                 105                 110

Phe Asn Pro Asn Asn Ala Ile Ala Ala Thr His Leu Cys Thr Ile Asn
        115                 120                 125

Asn Asp Lys Tyr Tyr Phe Ser Tyr Asp Gly Ile Leu Gln Asn Gly Tyr
    130                 135                 140
```

Ile Thr Ile Glu Arg Asn Asn Phe Tyr Phe Asp Ala Asn Asn Glu Ser
145 150 155 160

Lys Met Val Thr Gly Val Phe Lys Gly Pro Asn Gly Phe Glu Tyr Phe
165 170 175

Ala Pro Ala Asn Thr His Asn Asn Asn Ile Glu Gly Gln Ala Ile Val
180 185 190

Tyr Gln Asn Lys Phe Leu Thr Leu Asn Gly Lys Lys Tyr Tyr Phe Asp
195 200 205

Asn Asp Ser Lys Ala Val Thr Gly Trp Gln Thr Ile Asp Ser Lys Lys
210 215 220

Tyr Tyr Phe Asn Leu Asn Thr Ala Val Ala Val Thr Gly Trp Gln Thr
225 230 235 240

Ile Asp Gly Glu Lys Tyr Tyr Phe Asn Leu Asn Thr Ala Glu Ala Ala
245 250 255

Thr Gly Trp Gln Thr Ile Asp Gly Lys Arg Tyr Tyr Phe Asn Thr Asn
260 265 270

Thr Tyr Ile Ala Ser Thr Gly Tyr Thr Ile Ile Asn Gly Lys His Phe
275 280 285

Tyr Phe Asn Thr Asp Gly Ile Met Gln Ile Gly Val Phe Lys Gly Pro
290 295 300

Asp Gly Phe Glu Tyr Phe Ala Pro Ala Asn Thr His Asn Asn Asn Ile
305 310 315 320

Glu Gly Gln Ala Ile Leu Tyr Gln Asn Lys Phe Leu Thr Leu Asn Gly
325 330 335

Lys Lys Tyr Tyr Phe Gly Ser Asp Ser Lys Ala Val Thr Gly Leu Arg
340 345 350

Thr Ile Asp Gly Lys Lys Tyr Tyr Phe Asn Thr Asn Thr Ala Val Ala
355 360 365

Val Thr Gly Trp Gln Thr Ile Asn Gly Lys Lys Tyr Tyr Phe Asn Thr
370 375 380

Asn Thr Tyr Ile Ala Leu Glu
385 390

<210> SEQ ID NO 31
<211> LENGTH: 1290
<212> TYPE: DNA
<213> ORGANISM: Artificial sequence
<220> FEATURE:
<223> OTHER INFORMATION: Synthetic polynucleotide
<220> FEATURE:
<221> NAME/KEY: CDS
<222> LOCATION: (1)..(1290)

<400> SEQUENCE: 31 cat atg aaa aaa tta ttg att gcc gca atg atg gcg gct gcc ttg gca 48
His Met Lys Lys Leu Leu Ile Ala Ala Met Met Ala Ala Ala Leu Ala
1 5 10 15 gct tgt tcg caa gaa gcc aaa cag gag gtt aag gaa gcg gtt caa gcc 96
Ala Cys Ser Gln Glu Ala Lys Gln Glu Val Lys Glu Ala Val Gln Ala
20 25 30 gtt gag tcc gat gtt aaa gac act gcg gga tcc gcc gaa gca gcc acc 144
Val Glu Ser Asp Val Lys Asp Thr Ala Gly Ser Ala Glu Ala Ala Thr
35 40 45 ggc tgg caa acc att gat gga aaa aaa tat tac ttc aat aca aat acg 192
Gly Trp Gln Thr Ile Asp Gly Lys Lys Tyr Tyr Phe Asn Thr Asn Thr
50 55 60 agc att gcc agc acc ggt tat acc att atc aac ggc aaa tat ttc tac 240

-continued

```
Ser Ile Ala Ser Thr Gly Tyr Thr Ile Ile Asn Gly Lys Tyr Phe Tyr
65                  70                  75                  80

ttc aac acc gat ggc att atg cag att ggt gtg ttc aaa gtg ccg aat      288
Phe Asn Thr Asp Gly Ile Met Gln Ile Gly Val Phe Lys Val Pro Asn
                85                  90                  95

ggc ttt gag tat ttc gct ccg gct aac acc cat aat aac aat att gag      336
Gly Phe Glu Tyr Phe Ala Pro Ala Asn Thr His Asn Asn Asn Ile Glu
            100                 105                 110

ggc cag gcg atc ctg tat cag aat aaa ttc ctg aca ctg aac ggc aaa      384
Gly Gln Ala Ile Leu Tyr Gln Asn Lys Phe Leu Thr Leu Asn Gly Lys
        115                 120                 125

aaa tac tat ttc ggc agc gat tca aaa gca att aca ggt tgg caa aca      432
Lys Tyr Tyr Phe Gly Ser Asp Ser Lys Ala Ile Thr Gly Trp Gln Thr
    130                 135                 140

att gac ggg aaa aag tac tat ttt aat ccg aac aat gcg atc gca gca      480
Ile Asp Gly Lys Lys Tyr Tyr Phe Asn Pro Asn Asn Ala Ile Ala Ala
145                 150                 155                 160

acc cat ctg tgt acc att aat aac gat aaa tac tac ttt agc tat gac      528
Thr His Leu Cys Thr Ile Asn Asn Asp Lys Tyr Tyr Phe Ser Tyr Asp
                165                 170                 175

ggc atc ctg cag aat ggc tat atc acc att gaa cgc aac aac ttt tac      576
Gly Ile Leu Gln Asn Gly Tyr Ile Thr Ile Glu Arg Asn Asn Phe Tyr
            180                 185                 190

ttt gat gcc aac aac gaa agc aaa atg gtg acc ggt gtt ttt aaa ggc      624
Phe Asp Ala Asn Asn Glu Ser Lys Met Val Thr Gly Val Phe Lys Gly
        195                 200                 205

cct aat ggc ttc gaa tac ttc gca cca gcg aat acg cat aac aat aac      672
Pro Asn Gly Phe Glu Tyr Phe Ala Pro Ala Asn Thr His Asn Asn Asn
    210                 215                 220

atc gag ggt caa gcg att gtc tac cag aat aaa ttt ctg act ctg aat      720
Ile Glu Gly Gln Ala Ile Val Tyr Gln Asn Lys Phe Leu Thr Leu Asn
225                 230                 235                 240

ggt aaa aaa tat tac ttc gat aat gat tca aaa gcc gtg acc gga tgg      768
Gly Lys Lys Tyr Tyr Phe Asp Asn Asp Ser Lys Ala Val Thr Gly Trp
                245                 250                 255

caa act atc gat tca aaa aaa tac tac ttt aac ctg aac acc gca gtt      816
Gln Thr Ile Asp Ser Lys Lys Tyr Tyr Phe Asn Leu Asn Thr Ala Val
            260                 265                 270

gca gtt aca ggg tgg caa acc atc gac ggt gag aaa tac tac ttc aat      864
Ala Val Thr Gly Trp Gln Thr Ile Asp Gly Glu Lys Tyr Tyr Phe Asn
        275                 280                 285

ctg aat aca gcc gaa gcc gct act gga tgg cag acg att gac gga aaa      912
Leu Asn Thr Ala Glu Ala Ala Thr Gly Trp Gln Thr Ile Asp Gly Lys
    290                 295                 300

cgc tat tat ttt aat acc aac acc tat att gcg agc aca ggc tat acc      960
Arg Tyr Tyr Phe Asn Thr Asn Thr Tyr Ile Ala Ser Thr Gly Tyr Thr
305                 310                 315                 320

atc att aat ggt aaa cac ttc tac ttt aac acg gac ggt atc atg caa     1008
Ile Ile Asn Gly Lys His Phe Tyr Phe Asn Thr Asp Gly Ile Met Gln
                325                 330                 335

atc ggc gtg ttt aaa ggc cca gac ggt ttc gag tac ttt gcg cca gca     1056
Ile Gly Val Phe Lys Gly Pro Asp Gly Phe Glu Tyr Phe Ala Pro Ala
            340                 345                 350

aac acc cac aat aat aac atc gaa gga caa gcc atc ctg tat caa aac     1104
Asn Thr His Asn Asn Asn Ile Glu Gly Gln Ala Ile Leu Tyr Gln Asn
        355                 360                 365

aaa ttt ctg acg ctg aat ggc aaa aaa tac tac ttc ggt agt gat agc     1152
Lys Phe Leu Thr Leu Asn Gly Lys Lys Tyr Tyr Phe Gly Ser Asp Ser
    370                 375                 380
```

-continued

```
aaa gct gtt aca ggt ctg cgt acc atc gac gga aaa aaa tat tac ttt     1200
Lys Ala Val Thr Gly Leu Arg Thr Ile Asp Gly Lys Lys Tyr Tyr Phe
385                 390                 395                 400

aat act aac acg gca gtg gca gtg acg ggc tgg caa acg atc aac ggg     1248
Asn Thr Asn Thr Ala Val Ala Val Thr Gly Trp Gln Thr Ile Asn Gly
                405                 410                 415

aaa aaa tac tac ttc aac acc aac acg tat att gcc ctc gag             1290
Lys Lys Tyr Tyr Phe Asn Thr Asn Thr Tyr Ile Ala Leu Glu
            420                 425                 430


<210> SEQ ID NO 32
<211> LENGTH: 430
<212> TYPE: PRT
<213> ORGANISM: Artificial sequence
<220> FEATURE:
<223> OTHER INFORMATION: Synthetic Construct

<400> SEQUENCE: 32

His Met Lys Lys Leu Leu Ile Ala Ala Met Met Ala Ala Ala Leu Ala
1               5                   10                  15

Ala Cys Ser Gln Glu Ala Lys Gln Glu Val Lys Glu Ala Val Gln Ala
            20                  25                  30

Val Glu Ser Asp Val Lys Asp Thr Ala Gly Ser Ala Glu Ala Ala Thr
        35                  40                  45

Gly Trp Gln Thr Ile Asp Gly Lys Lys Tyr Tyr Phe Asn Thr Asn Thr
    50                  55                  60

Ser Ile Ala Ser Thr Gly Tyr Thr Ile Ile Asn Gly Lys Tyr Phe Tyr
65                  70                  75                  80

Phe Asn Thr Asp Gly Ile Met Gln Ile Gly Val Phe Lys Val Pro Asn
                85                  90                  95

Gly Phe Glu Tyr Phe Ala Pro Ala Asn Thr His Asn Asn Asn Ile Glu
            100                 105                 110

Gly Gln Ala Ile Leu Tyr Gln Asn Lys Phe Leu Thr Leu Asn Gly Lys
        115                 120                 125

Lys Tyr Tyr Phe Gly Ser Asp Ser Lys Ala Ile Thr Gly Trp Gln Thr
    130                 135                 140

Ile Asp Gly Lys Lys Tyr Tyr Phe Asn Pro Asn Asn Ala Ile Ala Ala
145                 150                 155                 160

Thr His Leu Cys Thr Ile Asn Asn Asp Lys Tyr Tyr Phe Ser Tyr Asp
                165                 170                 175

Gly Ile Leu Gln Asn Gly Tyr Ile Thr Ile Glu Arg Asn Asn Phe Tyr
            180                 185                 190

Phe Asp Ala Asn Asn Glu Ser Lys Met Val Thr Gly Val Phe Lys Gly
        195                 200                 205

Pro Asn Gly Phe Glu Tyr Phe Ala Pro Ala Asn Thr His Asn Asn Asn
    210                 215                 220

Ile Glu Gly Gln Ala Ile Val Tyr Gln Asn Lys Phe Leu Thr Leu Asn
225                 230                 235                 240

Gly Lys Lys Tyr Tyr Phe Asp Asn Asp Ser Lys Ala Val Thr Gly Trp
                245                 250                 255

Gln Thr Ile Asp Ser Lys Lys Tyr Tyr Phe Asn Leu Asn Thr Ala Val
            260                 265                 270

Ala Val Thr Gly Trp Gln Thr Ile Asp Gly Glu Lys Tyr Tyr Phe Asn
        275                 280                 285

Leu Asn Thr Ala Glu Ala Ala Thr Gly Trp Gln Thr Ile Asp Gly Lys
    290                 295                 300
```

```
Arg Tyr Tyr Phe Asn Thr Asn Thr Tyr Ile Ala Ser Thr Gly Tyr Thr
305                 310                 315                 320

Ile Ile Asn Gly Lys His Phe Tyr Phe Asn Thr Asp Gly Ile Met Gln
                325                 330                 335

Ile Gly Val Phe Lys Gly Pro Asp Gly Phe Glu Tyr Phe Ala Pro Ala
            340                 345                 350

Asn Thr His Asn Asn Asn Ile Glu Gly Gln Ala Ile Leu Tyr Gln Asn
        355                 360                 365

Lys Phe Leu Thr Leu Asn Gly Lys Lys Tyr Tyr Phe Gly Ser Asp Ser
    370                 375                 380

Lys Ala Val Thr Gly Leu Arg Thr Ile Asp Gly Lys Lys Tyr Tyr Phe
385                 390                 395                 400

Asn Thr Asn Thr Ala Val Ala Val Thr Gly Trp Gln Thr Ile Asn Gly
                405                 410                 415

Lys Lys Tyr Tyr Phe Asn Thr Asn Thr Tyr Ile Ala Leu Glu
            420                 425                 430


<210> SEQ ID NO 33
<211> LENGTH: 1182
<212> TYPE: DNA
<213> ORGANISM: Artificial sequence
<220> FEATURE:
<223> OTHER INFORMATION: Synthetic polynucleotide
<220> FEATURE:
<221> NAME/KEY: CDS
<222> LOCATION: (1)..(1182)

<400> SEQUENCE: 33

cat atg gga tcc aaa gcc gtg acc gga tgg caa act atc gat tca aaa       48
His Met Gly Ser Lys Ala Val Thr Gly Trp Gln Thr Ile Asp Ser Lys
1               5                   10                  15

aaa tac tac ttt aac ctg aac acc gca gtt gca gtt aca ggg tgg caa       96
Lys Tyr Tyr Phe Asn Leu Asn Thr Ala Val Ala Val Thr Gly Trp Gln
            20                  25                  30

acc atc gac ggt gag aaa tac tac ttc aat ctg aat aca gcc gaa gcc      144
Thr Ile Asp Gly Glu Lys Tyr Tyr Phe Asn Leu Asn Thr Ala Glu Ala
        35                  40                  45

gct act gga tgg cag acg att gac gga aaa cgc tat tat ttt aat acc      192
Ala Thr Gly Trp Gln Thr Ile Asp Gly Lys Arg Tyr Tyr Phe Asn Thr
    50                  55                  60

aac acc tat att gcg agc aca ggc tat acc atc att aat ggt aaa cac      240
Asn Thr Tyr Ile Ala Ser Thr Gly Tyr Thr Ile Ile Asn Gly Lys His
65                  70                  75                  80

ttc tac ttt aac acg gac ggt atc atg caa atc ggc gtg ttt aaa ggc      288
Phe Tyr Phe Asn Thr Asp Gly Ile Met Gln Ile Gly Val Phe Lys Gly
                85                  90                  95

cca gac ggt ttc gag tac ttt gcg cca gca aac acc cac aat aat aac      336
Pro Asp Gly Phe Glu Tyr Phe Ala Pro Ala Asn Thr His Asn Asn Asn
            100                 105                 110

atc gaa gga caa gcc atc ctg tat caa aac aaa ttt ctg acg ctg aat      384
Ile Glu Gly Gln Ala Ile Leu Tyr Gln Asn Lys Phe Leu Thr Leu Asn
        115                 120                 125

ggc aaa aaa tac tac ttc ggt agt gat agc aaa gct gtt aca ggt ctg      432
Gly Lys Lys Tyr Tyr Phe Gly Ser Asp Ser Lys Ala Val Thr Gly Leu
    130                 135                 140

cgt acc atc gac gga aaa aaa tat tac ttt aat act aac acg gca gtg      480
Arg Thr Ile Asp Gly Lys Lys Tyr Tyr Phe Asn Thr Asn Thr Ala Val
145                 150                 155                 160

gca gtg acg ggc tgg caa acg atc aac ggg aaa aaa tac tac ttc aac      528
Ala Val Thr Gly Trp Gln Thr Ile Asn Gly Lys Lys Tyr Tyr Phe Asn
```

```
                165                 170                 175

acc aac acg tat att gcc tca acc ggc tat aca att atc agc ggt aaa      576
Thr Asn Thr Tyr Ile Ala Ser Thr Gly Tyr Thr Ile Ile Ser Gly Lys
            180                 185                 190

cac ttt tat ttc aat aca gat ggg atc atg cag atc gga gtt ttc aaa      624
His Phe Tyr Phe Asn Thr Asp Gly Ile Met Gln Ile Gly Val Phe Lys
        195                 200                 205

gga cct gat gga ttc gag tat ttt gct cct gcg aat acc gat gcc aat      672
Gly Pro Asp Gly Phe Glu Tyr Phe Ala Pro Ala Asn Thr Asp Ala Asn
    210                 215                 220

aac att gag gga cag gca att cgc tat cag aat cgt ttt ctg tat ctg      720
Asn Ile Glu Gly Gln Ala Ile Arg Tyr Gln Asn Arg Phe Leu Tyr Leu
225                 230                 235                 240

cac gat aat att tat tat ttt ggc aat gat tcc aaa gcg gca acc ggt      768
His Asp Asn Ile Tyr Tyr Phe Gly Asn Asp Ser Lys Ala Ala Thr Gly
                245                 250                 255

tgg gcc acc att gat ggt aat cgt tat tat ttt gag ccg aat acc gca      816
Trp Ala Thr Ile Asp Gly Asn Arg Tyr Tyr Phe Glu Pro Asn Thr Ala
            260                 265                 270

atg ggt gcc aat ggt tat aaa acg att gat aac aaa aac ttt tat ttt      864
Met Gly Ala Asn Gly Tyr Lys Thr Ile Asp Asn Lys Asn Phe Tyr Phe
        275                 280                 285

cgc aac ggc ctg ccg cag att ggc gta ttc aaa ggt cct aac ggt ttt      912
Arg Asn Gly Leu Pro Gln Ile Gly Val Phe Lys Gly Pro Asn Gly Phe
    290                 295                 300

gag tac ttc gct cca gcc aat aca gat gca aat aat atc gac ggc cag      960
Glu Tyr Phe Ala Pro Ala Asn Thr Asp Ala Asn Asn Ile Asp Gly Gln
305                 310                 315                 320

gcc atc cgc tac cag aac cgc ttc ctg cat ctg ctg ggt aaa atc tat     1008
Ala Ile Arg Tyr Gln Asn Arg Phe Leu His Leu Leu Gly Lys Ile Tyr
                325                 330                 335

tat ttc ggc aac aac agc aaa gcg gta act ggt tgg caa acc atc aat     1056
Tyr Phe Gly Asn Asn Ser Lys Ala Val Thr Gly Trp Gln Thr Ile Asn
            340                 345                 350

agc aaa gtg tat tat ttc atg ccg gat aca gca atg gca gca gcc ggt     1104
Ser Lys Val Tyr Tyr Phe Met Pro Asp Thr Ala Met Ala Ala Ala Gly
        355                 360                 365

ggt ctg ttt gaa att gat ggt gtg atc tat ttc ttt ggt gtg gat ggt     1152
Gly Leu Phe Glu Ile Asp Gly Val Ile Tyr Phe Phe Gly Val Asp Gly
    370                 375                 380

gtt aaa gca ccg ggt att tat ggc ctc gag                             1182
Val Lys Ala Pro Gly Ile Tyr Gly Leu Glu
385                 390


<210> SEQ ID NO 34
<211> LENGTH: 394
<212> TYPE: PRT
<213> ORGANISM: Artificial sequence
<220> FEATURE:
<223> OTHER INFORMATION: Synthetic Construct

<400> SEQUENCE: 34

His Met Gly Ser Lys Ala Val Thr Gly Trp Gln Thr Ile Asp Ser Lys
1               5                   10                  15

Lys Tyr Tyr Phe Asn Leu Asn Thr Ala Val Ala Val Thr Gly Trp Gln
            20                  25                  30

Thr Ile Asp Gly Glu Lys Tyr Tyr Phe Asn Leu Asn Thr Ala Glu Ala
        35                  40                  45

Ala Thr Gly Trp Gln Thr Ile Asp Gly Lys Arg Tyr Tyr Phe Asn Thr
    50                  55                  60
```

```
Asn Thr Tyr Ile Ala Ser Thr Gly Tyr Thr Ile Ile Asn Gly Lys His
65                  70                  75                  80

Phe Tyr Phe Asn Thr Asp Gly Ile Met Gln Ile Gly Val Phe Lys Gly
                85                  90                  95

Pro Asp Gly Phe Glu Tyr Phe Ala Pro Ala Asn Thr His Asn Asn Asn
            100                 105                 110

Ile Glu Gly Gln Ala Ile Leu Tyr Gln Asn Lys Phe Leu Thr Leu Asn
        115                 120                 125

Gly Lys Lys Tyr Tyr Phe Gly Ser Asp Ser Lys Ala Val Thr Gly Leu
    130                 135                 140

Arg Thr Ile Asp Gly Lys Lys Tyr Tyr Phe Asn Thr Asn Thr Ala Val
145                 150                 155                 160

Ala Val Thr Gly Trp Gln Thr Ile Asn Gly Lys Lys Tyr Tyr Phe Asn
                165                 170                 175

Thr Asn Thr Tyr Ile Ala Ser Thr Gly Tyr Thr Ile Ile Ser Gly Lys
            180                 185                 190

His Phe Tyr Phe Asn Thr Asp Gly Ile Met Gln Ile Gly Val Phe Lys
        195                 200                 205

Gly Pro Asp Gly Phe Glu Tyr Phe Ala Pro Ala Asn Thr Asp Ala Asn
    210                 215                 220

Asn Ile Glu Gly Gln Ala Ile Arg Tyr Gln Asn Arg Phe Leu Tyr Leu
225                 230                 235                 240

His Asp Asn Ile Tyr Tyr Phe Gly Asn Asp Ser Lys Ala Ala Thr Gly
                245                 250                 255

Trp Ala Thr Ile Asp Gly Asn Arg Tyr Tyr Phe Glu Pro Asn Thr Ala
            260                 265                 270

Met Gly Ala Asn Gly Tyr Lys Thr Ile Asp Asn Lys Asn Phe Tyr Phe
        275                 280                 285

Arg Asn Gly Leu Pro Gln Ile Gly Val Phe Lys Gly Pro Asn Gly Phe
    290                 295                 300

Glu Tyr Phe Ala Pro Ala Asn Thr Asp Ala Asn Asn Ile Asp Gly Gln
305                 310                 315                 320

Ala Ile Arg Tyr Gln Asn Arg Phe Leu His Leu Leu Gly Lys Ile Tyr
                325                 330                 335

Tyr Phe Gly Asn Asn Ser Lys Ala Val Thr Gly Trp Gln Thr Ile Asn
            340                 345                 350

Ser Lys Val Tyr Tyr Phe Met Pro Asp Thr Ala Met Ala Ala Ala Gly
        355                 360                 365

Gly Leu Phe Glu Ile Asp Gly Val Ile Tyr Phe Phe Gly Val Asp Gly
    370                 375                 380

Val Lys Ala Pro Gly Ile Tyr Gly Leu Glu
385                 390
```

<210> SEQ ID NO 35
<211> LENGTH: 1299
<212> TYPE: DNA
<213> ORGANISM: Artificial sequence
<220> FEATURE:
<223> OTHER INFORMATION: Synthetic polynucleotide
<220> FEATURE:
<221> NAME/KEY: CDS
<222> LOCATION: (1)..(1299)

<400> SEQUENCE: 35

```
cat atg aaa aaa tta ttg att gcc gca atg atg gcg gct gcc ttg gca      48
His Met Lys Lys Leu Leu Ile Ala Ala Met Met Ala Ala Ala Leu Ala
```

-continued

```
1               5                   10                  15

gct tgt tcg caa gaa gcc aaa cag gag gtt aag gaa gcg gtt caa gcc        96
Ala Cys Ser Gln Glu Ala Lys Gln Glu Val Lys Glu Ala Val Gln Ala
            20                  25                  30

gtt gag tcc gat gtt aaa gac act gcg gga tcc aaa gcc gtg acc gga       144
Val Glu Ser Asp Val Lys Asp Thr Ala Gly Ser Lys Ala Val Thr Gly
        35                  40                  45

tgg caa act atc gat tca aaa aaa tac tac ttt aac ctg aac acc gca       192
Trp Gln Thr Ile Asp Ser Lys Lys Tyr Tyr Phe Asn Leu Asn Thr Ala
    50                  55                  60

gtt gca gtt aca ggg tgg caa acc atc gac ggt gag aaa tac tac ttc       240
Val Ala Val Thr Gly Trp Gln Thr Ile Asp Gly Glu Lys Tyr Tyr Phe
65                  70                  75                  80

aat ctg aat aca gcc gaa gcc gct act gga tgg cag acg att gac gga       288
Asn Leu Asn Thr Ala Glu Ala Ala Thr Gly Trp Gln Thr Ile Asp Gly
                85                  90                  95

aaa cgc tat tat ttt aat acc aac acc tat att gcg agc aca ggc tat       336
Lys Arg Tyr Tyr Phe Asn Thr Asn Thr Tyr Ile Ala Ser Thr Gly Tyr
            100                 105                 110

acc atc att aat ggt aaa cac ttc tac ttt aac acg gac ggt atc atg       384
Thr Ile Ile Asn Gly Lys His Phe Tyr Phe Asn Thr Asp Gly Ile Met
        115                 120                 125

caa atc ggc gtg ttt aaa ggc cca gac ggt ttc gag tac ttt gcg cca       432
Gln Ile Gly Val Phe Lys Gly Pro Asp Gly Phe Glu Tyr Phe Ala Pro
    130                 135                 140

gca aac acc cac aat aat aac atc gaa gga caa gcc atc ctg tat caa       480
Ala Asn Thr His Asn Asn Asn Ile Glu Gly Gln Ala Ile Leu Tyr Gln
145                 150                 155                 160

aac aaa ttt ctg acg ctg aat ggc aaa aaa tac tac ttc ggt agt gat       528
Asn Lys Phe Leu Thr Leu Asn Gly Lys Lys Tyr Tyr Phe Gly Ser Asp
                165                 170                 175

agc aaa gct gtt aca ggt ctg cgt acc atc gac gga aaa aaa tat tac       576
Ser Lys Ala Val Thr Gly Leu Arg Thr Ile Asp Gly Lys Lys Tyr Tyr
            180                 185                 190

ttt aat act aac acg gca gtg gca gtg acg ggc tgg caa acg atc aac       624
Phe Asn Thr Asn Thr Ala Val Ala Val Thr Gly Trp Gln Thr Ile Asn
        195                 200                 205

ggg aaa aaa tac tac ttc aac acc aac acg tat att gcc tca acc ggc       672
Gly Lys Lys Tyr Tyr Phe Asn Thr Asn Thr Tyr Ile Ala Ser Thr Gly
    210                 215                 220

tat aca att atc agc ggt aaa cac ttt tat ttc aat aca gat ggg atc       720
Tyr Thr Ile Ile Ser Gly Lys His Phe Tyr Phe Asn Thr Asp Gly Ile
225                 230                 235                 240

atg cag atc gga gtt ttc aaa gga cct gat gga ttc gag tat ttt gct       768
Met Gln Ile Gly Val Phe Lys Gly Pro Asp Gly Phe Glu Tyr Phe Ala
                245                 250                 255

cct gcg aat acc gat gcc aat aac att gag gga cag gca att cgc tat       816
Pro Ala Asn Thr Asp Ala Asn Asn Ile Glu Gly Gln Ala Ile Arg Tyr
            260                 265                 270

cag aat cgt ttt ctg tat ctg cac gat aat att tat tat ttt ggc aat       864
Gln Asn Arg Phe Leu Tyr Leu His Asp Asn Ile Tyr Tyr Phe Gly Asn
        275                 280                 285

gat tcc aaa gcg gca acc ggt tgg gcc acc att gat ggt aat cgt tat       912
Asp Ser Lys Ala Ala Thr Gly Trp Ala Thr Ile Asp Gly Asn Arg Tyr
    290                 295                 300

tat ttt gag ccg aat acc gca atg ggt gcc aat ggt tat aaa acg att       960
Tyr Phe Glu Pro Asn Thr Ala Met Gly Ala Asn Gly Tyr Lys Thr Ile
305                 310                 315                 320

gat aac aaa aac ttt tat ttt cgc aac ggc ctg ccg cag att ggc gta      1008
```

-continued

```
Asp Asn Lys Asn Phe Tyr Phe Arg Asn Gly Leu Pro Gln Ile Gly Val
            325                 330                 335

ttc aaa ggt cct aac ggt ttt gag tac ttc gct cca gcc aat aca gat     1056
Phe Lys Gly Pro Asn Gly Phe Glu Tyr Phe Ala Pro Ala Asn Thr Asp
            340                 345                 350

gca aat aat atc gac ggc cag gcc atc cgc tac cag aac cgc ttc ctg     1104
Ala Asn Asn Ile Asp Gly Gln Ala Ile Arg Tyr Gln Asn Arg Phe Leu
        355                 360                 365

cat ctg ctg ggt aaa atc tat tat ttc ggc aac aac agc aaa gcg gta     1152
His Leu Leu Gly Lys Ile Tyr Tyr Phe Gly Asn Asn Ser Lys Ala Val
    370                 375                 380

act ggt tgg caa acc atc aat agc aaa gtg tat tat ttc atg ccg gat     1200
Thr Gly Trp Gln Thr Ile Asn Ser Lys Val Tyr Tyr Phe Met Pro Asp
385                 390                 395                 400

aca gca atg gca gca gcc ggt ggt ctg ttt gaa att gat ggt gtg atc     1248
Thr Ala Met Ala Ala Ala Gly Gly Leu Phe Glu Ile Asp Gly Val Ile
            405                 410                 415

tat ttc ttt ggt gtg gat ggt gtt aaa gca ccg ggt att tat ggc ctc     1296
Tyr Phe Phe Gly Val Asp Gly Val Lys Ala Pro Gly Ile Tyr Gly Leu
            420                 425                 430

gag                                                                 1299
Glu


<210> SEQ ID NO 36
<211> LENGTH: 433
<212> TYPE: PRT
<213> ORGANISM: Artificial sequence
<220> FEATURE:
<223> OTHER INFORMATION: Synthetic Construct

<400> SEQUENCE: 36

His Met Lys Lys Leu Leu Ile Ala Ala Met Met Ala Ala Ala Leu Ala
1               5                   10                  15

Ala Cys Ser Gln Glu Ala Lys Gln Glu Val Lys Glu Ala Val Gln Ala
            20                  25                  30

Val Glu Ser Asp Val Lys Asp Thr Ala Gly Ser Lys Ala Val Thr Gly
        35                  40                  45

Trp Gln Thr Ile Asp Ser Lys Lys Tyr Tyr Phe Asn Leu Asn Thr Ala
    50                  55                  60

Val Ala Val Thr Gly Trp Gln Thr Ile Asp Gly Glu Lys Tyr Tyr Phe
65                  70                  75                  80

Asn Leu Asn Thr Ala Glu Ala Ala Thr Gly Trp Gln Thr Ile Asp Gly
                85                  90                  95

Lys Arg Tyr Tyr Phe Asn Thr Asn Thr Tyr Ile Ala Ser Thr Gly Tyr
            100                 105                 110

Thr Ile Ile Asn Gly Lys His Phe Tyr Phe Asn Thr Asp Gly Ile Met
        115                 120                 125

Gln Ile Gly Val Phe Lys Gly Pro Asp Gly Phe Glu Tyr Phe Ala Pro
    130                 135                 140

Ala Asn Thr His Asn Asn Asn Ile Glu Gly Gln Ala Ile Leu Tyr Gln
145                 150                 155                 160

Asn Lys Phe Leu Thr Leu Asn Gly Lys Lys Tyr Tyr Phe Gly Ser Asp
                165                 170                 175

Ser Lys Ala Val Thr Gly Leu Arg Thr Ile Asp Gly Lys Lys Tyr Tyr
            180                 185                 190

Phe Asn Thr Asn Thr Ala Val Ala Val Thr Gly Trp Gln Thr Ile Asn
        195                 200                 205
```

-continued

```
Gly Lys Lys Tyr Tyr Phe Asn Thr Asn Thr Tyr Ile Ala Ser Thr Gly
    210                 215                 220

Tyr Thr Ile Ile Ser Gly Lys His Phe Tyr Phe Asn Thr Asp Gly Ile
225                 230                 235                 240

Met Gln Ile Gly Val Phe Lys Gly Pro Asp Gly Phe Glu Tyr Phe Ala
            245                 250                 255

Pro Ala Asn Thr Asp Ala Asn Asn Ile Glu Gly Gln Ala Ile Arg Tyr
            260                 265                 270

Gln Asn Arg Phe Leu Tyr Leu His Asp Asn Ile Tyr Tyr Phe Gly Asn
        275                 280                 285

Asp Ser Lys Ala Ala Thr Gly Trp Ala Thr Ile Asp Gly Asn Arg Tyr
        290                 295                 300

Tyr Phe Glu Pro Asn Thr Ala Met Gly Ala Asn Gly Tyr Lys Thr Ile
305                 310                 315                 320

Asp Asn Lys Asn Phe Tyr Phe Arg Asn Gly Leu Pro Gln Ile Gly Val
                325                 330                 335

Phe Lys Gly Pro Asn Gly Phe Glu Tyr Phe Ala Pro Ala Asn Thr Asp
            340                 345                 350

Ala Asn Asn Ile Asp Gly Gln Ala Ile Arg Tyr Gln Asn Arg Phe Leu
        355                 360                 365

His Leu Leu Gly Lys Ile Tyr Tyr Phe Gly Asn Asn Ser Lys Ala Val
        370                 375                 380

Thr Gly Trp Gln Thr Ile Asn Ser Lys Val Tyr Tyr Phe Met Pro Asp
385                 390                 395                 400

Thr Ala Met Ala Ala Ala Gly Gly Leu Phe Glu Ile Asp Gly Val Ile
            405                 410                 415

Tyr Phe Phe Gly Val Asp Gly Val Lys Ala Pro Gly Ile Tyr Gly Leu
            420                 425                 430

Glu
```

COMPOSITIONS AND METHODS FOR TREATING CLOSTRIDIUM DIFFICILE-ASSOCIATED DISEASES

CROSS-REFERENCE TO RELATED APPLICATION

This application claims priority to U.S. Provisional Application No. 61/782,390, filed on Mar. 14, 2013, the content of which is hereby incorporated herein in its entirety.

BACKGROUND

*Clostridium difficile* (Cd) is an emerging pathogen of opportunistic infection in hospitals worldwide. It is the major cause of antibiotic-associated pseudo-membranous colitis and diarrhea in human.

Cd asserts its effect through two large protein toxins: toxin A (tcdA) and toxin B (tcdB), which disrupt intestinal epithelial cells. tcdA and tcdB are large (250-308 kDa) protein toxins with multiple domains. The binding of the receptor binding domain (RBD) of Cd to carbohydrates on colonic epithelial cells is an initial step in pathogenesis. tcdA and/or tcdB enters the cells through receptor-mediated endocytosis and disrupts normal signaling pathways necessary for maintaining the cells' cytoskeleton, ultimately leading to inflammation and diarrhea. Various oligosaccharides, including the trisaccharide α-Gal-(1,3)-β-Gal-(1,4)-β-GlcNAc, bind specifically to tcdA, but the native human ligand has not been definitively identified.

Patients in hospitals treated with antibiotics have high risk of Cd infection, especially in children and those over 65 years old. Cd-associated diseases incur additional health care costs and extend hospital time. Morbidity and mortality of Cd-associated diseases have increased significantly, because of changes in the virulence of the causative strains.

Therefore, there is a need for prophylactic and therapeutic agents against Cd infection and Cd-associated diseases.

SUMMARY

Described herein are novel polypeptides, fusion polypeptides, nucleic acids encoding the polypeptides, immunotherapeutic compositions containing the polypeptides, and methods of using the polypeptides.

Polypeptides and/or Lipo-ploypeptides each containing one or more functional domains of Cd tcdA can be used for the preparation of vaccines against diseases caused by Cd-infection, the diagnosis of Cd infection, and for the generation of immunogenic reagents. Mono- or polyclonal antibodies raised against these polypeptides can be used for the diagnosis of infection by Cd and for immunizing against or treating diseases associated with Cd infection.

Accordingly, described herein is an isolated polypeptide containing one or more functional domains of Cd tcdA, e.g., tcdA-RBD. For example, the isolated polypeptide can have the amino acid sequence of any of SEQ ID NOs: 2, 4, 6, and 8-18 or a sequence that is at least 80% (e.g., 85%, 90%, 95%, 98%, or 99%) identical thereto. The polypeptide can further include a lipidating sequence. Such a polypeptide can be expressed in lipidated form.

Also described herein are an isolated nucleic acid molecule containing a sequence encoding the above-described polypeptide and a vector containing the nucleic acid molecule.

Further, an antibody or an antigenic fragment thereof that binds specifically to the above-described polypeptide is described. A kit for diagnosing Cd infection or a disease associate with the infection can contain one or more such antibodies.

A chimeric molecule containing a tcdA-RBD or a fragment thereof described herein can be linked to another molecule, e.g., a polypeptide, a polysaccharide, a nucleic acid molecule, or a small molecular compound. The linked polypeptide can include an antigenic surface protein or peptide from a pathogenic bacteria or virus, e.g., the evn protein of HIV, Eprotein of dengue virus, HA protein of influenza virus, F protein from RSV, and HN protein from PIV3. The linked polysaccharide can include different serotypes of oligosaccharide molecules from bacteria such as pneumococcal, meningococcal, *H. influenza, A. baumannii*, or *C. difficile.*

In another aspect, describe herein is an immunogenic composition containing the polypeptide, chimeric molecule, or nucleic acid molecule described herein. Such immunogenic composition can be used to protect against or treat Cd infection or diseases associated with the infection, or to induce an immune response.

An immunogenic composition containing an antigen and the above-described polypeptide as an adjuvant is also described.

The details of one or more embodiments are set forth in the accompanying drawing and the description below. Other features, objects, and advantages will be apparent from the description and drawing, and from the claims.

BRIEF DESCRIPTION OF DRAWINGS

FIG. 1 is a rationally designed consensus sequence of RBD (SEQ ID NO:26). The putative receptor binding sites are underlined.

DETAILED DESCRIPTION

Figure 2:
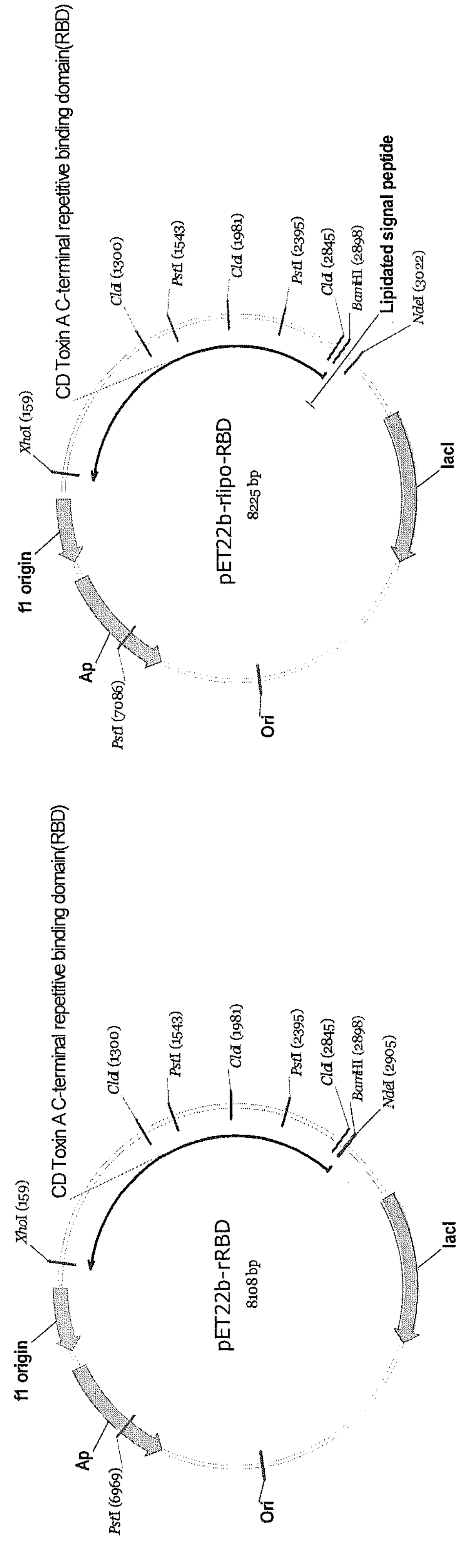
FIG. 2 is a schematic representation showing the construction of plasmids expressing either rRBD or rlipo-RBD in the *E. coli* system.

Described herein are novel polypeptides each containing the receptor-binding domain (RBD) of toxin A (tcdA) of *Clostridium difficile* (Cd). Unexpectedly, these polypeptides, particularly when expressed in lipidated form, are highly immunogenic and capable of inducing immunity against Cd challenge in animal models.

Described below are polypeptides (and nucleic acids encoding them) each containing one or more functional domains of Cd tcdA.

One exemplary polypeptide contains a C-terminal portion of tcdA, which includes the receptor-binding domain (RBD) of tcdA, i.e., tcdA-RBD or RBD. Shown below are the nucleic acid sequence (SEQ ID NO:1) encoding tcdA-RBD and the amino acid sequence of tcdA-RBD (SEQ ID NO:2). The putative receptor binding sites within the RBD are highlighted in SEQ ID NO:2.

| tcdA-RBD nucleic acids sequence |
|---|
| (SEQ ID NO:1)<br>TTTAATAGCGAGAATGAACTGGATCGTGATCATCTGGGCTTCAAAATCATCGATAATAAAACCTATTATTATGATGA<br>AGATAGCAAACTGGTGAAAGGCCTGATTAACATTAACAACAGCCTGTTTTACTTCGATCCGATTGAAAGCAATCTGG<br>TTACCGGTTGGCAGACCATTAACGGCAAAAAATATTATTTTGATATTAATACCGGTGCAGCCAGCACCAGCTATAAA<br>ATTATCAACGGCAAGCATTTCTATTTCAATAATAATGGCGTGATGCAGCTGGGCGTTTTTAAAGGTCCGGATGGTTT<br>TGAATATTTTGCACCGGCAAATACCCAGAACAATAATATTGAAGGTCAGGCCATTGTGTATCAGAGCAAATTTCTGA<br>CCCTGAACGGTAAAAAATACTACTTCGACAACGATAGCAAAGCAGTGACCGGTTGGCGCATTATTAACAACGAGAAA<br>TATTATTTCAATCCGAATAACGCCATTGCAGCAGTTGGTCTGCAGGTTATTGACAACAATAAATATTACTTTAACCC<br>GGACACCGCCATTATTAGCAAAGGCTGGCAGACCGTTAATGGTAGCCGTTATTATTTCGATACCGATACCGCGATTG<br>CCTTTAATGGCTATAAAACCATCGACGGCAAACACTTCTATTTTGATAGCGATTGCGTGGTGAAAATTGGTGTTTTT<br>AGCGGTAGCAACGGCTTTGAATACTTTGCCCCTGCCAATACCTACAACAACAACATCGAAGGCCAGGCAATCGTTTA<br>TCAGTCAAAATTCCTGACGCTGAATGGGAAAAAATATTACTTTGACAATAACAGCAAAGCCGTTACGGGATGGCAGA<br>CAATTGATAGCAAAAAATACTACTTCAATACCAATACCGCAGAAGCAGCAACAGGTTGGCAGACGATCGATGGTAAA<br>AAATATTATTTCAACACGAACACAGCCGAAGCAGCCACCGGCTGGCAAACCATTGATGGAAAAAAATATTACTTCAA<br>TACAAATACGAGCATTGCCAGCACCGGTTATACCATTATCAACGGCAAATATTTCTACTTCAACACCGATGGCATTA<br>TGCAGATTGGTGTGTTCAAAGTGCCGAATGGCTTTGAGTATTTCGCTCCGGCTAACACCCATAATAACAATATTGAG<br>GGCCAGGCGATCCTGTATCAGAATAAATTCCTGACACTGAACGGCAAAAAATACTATTTCGGCAGCGATTCAAAAGC<br>AATTACAGGTTGGCAAACAATTGACGGGAAAAAGTACTATTTTAATCCGAACAATGCGATCGCAGCAACCCATCTGT<br>GTACCATTAATAACGATAAATACTACTTTAGCTATGACGGCATCCTGCAGAATGGCTATATCACCATTGAACGCAAC |

-continued

AACTTTTACTTTGATGCCAACAACGAAAGCAAAATGGTGACCGGTGTTTTTAAAGGCCCTAATGGCTTCGAATACTT

CGCACCAGCGAATACGCATAACAATAACATCGAGGGTCAAGCGATTGTCTACCAGAATAAATTTCTGACTCTGAATG

GTAAAAAATATTACTTCGATAATGATTCAAAAGCCGTGACCGGATGGCAAACTATCGATTCAAAAAAATACTACTTT

AACCTGAACACCGCAGTTGCAGTTACAGGGTGGCAAACCATCGACGGTGAGAAATACTACTTCAATCTGAATACAGC

CGAAGCCGCTACTGGATGGCAGACGATTGACGGAAAACGCTATTATTTTAATACCAACACCTATATTGCGAGCACAG

GCTATACCATCATTAATGGTAAACACTTCTACTTTAACACGGACGGTATCATGCAAATCGGCGTGTTTAAAGGCCCA

GACGGTTTCGAGTACTTTGCGCCAGCAAACACCCACAATAATAACATCGAAGGACAAGCCATCCTGTATCAAAACAA

ATTTCTGACGCTGAATGGCAAAAAATACTACTTCGGTAGTGATAGCAAAGCTGTTACAGGTCTGCGTACCATCGACG

GAAAAAAATATTACTTTAATACTAACACGGCAGTGGCAGTGACGGGCTGGCAAACGATCAACGGGAAAAAATACTAC

TTCAACACCAACACGTATATTGCCTCAACCGGCTATACAATTATCAGCGGTAAACACTTTTATTTCAATACAGATGG

GATCATGCAGATCGGAGTTTTCAAAGGACCTGATGGATTCGAGTATTTTGCTCCTGCGAATACCGATGCCAATAACA

TTGAGGGACAGGCAATTCGCTATCAGAATCGTTTTCTGTATCTGCACGATAATATTTATTATTTTGGCAATGATTCC

AAAGCGGCAACCGGTTGGGCCACCATTGATGGTAATCGTTATTATTTTGAGCCGAATACCGCAATGGGTGCCAATGG

TTATAAAACGATTGATAACAAAAACTTTTATTTTCGCAACGGCCTGCCGCAGATTGGCGTATTCAAAGGTCCTAACG

GTTTTGAGTACTTCGCTCCAGCCAATACAGATGCAAATAATATCGACGGCCAGGCCATCCGCTACCAGAACCGCTTC

CTGCATCTGCTGGGTAAAATCTATTATTTCGGCAACAACAGCAAAGCGGTAACTGGTTGGCAAACCATCAATAGCAA

AGTGTATTATTTCATGCCGGATACAGCAATGGCAGCAGCCGGTGGTCTGTTTGAAATTGATGGTGTGATCTATTTCT

TTGGTGTGGATGGTGTTAAAGCACCGGGTATTTATGGC tcdA-RBD amino acid sequence (SEQ ID NO: 2)

FNSENELDRDHLGFKIIDNKTYYYDEDSKLVKGLININNSLFYFDPIESNLVTGWQTINGKKYYFDINTGAASTSYK

IINGKHFYFNNNGVMQLGVFKGPDGFEYFAPANTQNNNIEGQAIVYQSKFLTLNGKKYYFDNDSKAVTGWRIINNEK

YYFNPNNAIAAVGLQVIDNNKYYFNPDTAIISKGWQTVNGSRYYFDTDTAIAFNGYKTIDGKHFYFDSDCVVKIGVF

SGSNGFEYFAPANTYNNNIEGQAIVYQSKFLTLNGKKYYFDNNSKAVTGWQTIDSKKYYFNTNTAEAATGWQTIDGK

KYYFNTNTAEAATGWQTIDGKKYYFNTNTSIASTGYTIINGKYFYFNTDGIMQIGVFKVPNGFEYFAPANTHNNNIE

GQAILYQNKFLTLNGKKYYFGSDSKAITGWQTIDGKKYYFNPNNAIAATHLCTINNDKYYFSYDGILQNGYITIERN

NFYFDANNESKMVTGVFKGPNGFEYFAPANTHNNNIEGQAIVYQNKFLTLNGKKYYFDNDSKAVTGWQTIDSKKYYF

NLNTAVAVTGWQTIDGEKYYFNLNTAEAATGWQTIDGKRYYFNTNTYIASTGYTIINGKHFYFNTDGIMQIGVFKGP

DGFEYFAPANTHNNNIEGQAILYQNKFLTLNGKKYYFGSDSKAVTGLRTIDGKKYYFNTNTAVAVTGWQTINGKKYY

FNTNTYIASTGYTIISGKHFYFNTDGIMQIGVFKGPDGFEYFAPANTDANNIEGQAIRYQNRFLYLHDNIYYFGNDS

KAATGWATIDGNRYYFEPNTAMGANGYKTIDNKNFYFRNGLPQIGVFKGPNGFEYFAPANTDANNIDGQAIRYQNRF

LHLLGKIYYFGNNSKAVTGWQTINSKVYYFMPDTAMAAAGGLFEIDGVIYFFGVDGVKAPGIYG

Also described herein are three fragments of tcdA-RBD, i.e., F1, F2 and F3. The amino acid sequences of these fragments and the nucleic acid sequences encoding them are shown below. The putative receptor binding sites are highlighted.

F1 nucleic acid sequence (SEQ ID NO: 3)

TTTAATAGCGAGAATGAACTGGATCGTGATCATCTGGGCTTCAAAATCATCGATAATAAAACCTATTATTATGATGA

AGATAGCAAACTGGTGAAAGGCCTGATTAACATTAACAACAGCCTGTTTTACTTCGATCCGATTGAAAGCAATCTGG

TTACCGGTTGGCAGACCATTAACGGCAAAAAATATTATTTTGATATTAATACCGGTGCAGCCAGCACCAGCTATAAA

ATTATCAACGGCAAGCATTTCTATTTCAATAATAATGGCGTGATGCAGCTGGGCGTTTTTAAAGGTCCGGATGGTTT

TGAATATTTTGCACCGGCAAATACCCAGAACAATAATATTGAAGGTCAGGCCATTGTGTATCAGAGCAAATTTCTGA

CCCTGAACGGTAAAAAATACTACTTCGACAACGATAGCAAAGCAGTGACCGGTTGGCGCATTATTAACAACGAGAAA

TATTATTTCAATCCGAATAACGCCATTGCAGCAGTTGGTCTGCAGGTTATTGACAACAATAAATATTACTTTAACCC

GGACACCGCCATTATTAGCAAAGGCTGGCAGACCGTTAATGGTAGCCGTTATTATTTCGATACCGATACCGCGATTG

CCTTTAATGGCTATAAAACCATCGACGGCAAACACTTCTATTTTGATAGCGATTGCGTGGTGAAAATTGGTGTTTTT

AGCGGTAGCAACGGCTTTGAATACTTTGCCCCTGCCAATACCTACAACAACAACATCGAAGGCCAGGCAATCGTTTA

TCAGTCAAAATTCCTGACGCTGAATGGGAAAAAATATTACTTTGACAATAACAGCAAAGCCGTTACGGGATGGCAGA

CAATTGATAGCAAAAAATACTACTTCAATACCAATACCGCAGAAGCAGCAACAGGTTGGCAGACGATCGATGGTAAA

AAATATTATTTCAACACGAACACAGCCGAAGCAGCCACCGGCTGGCAAACCATTGATGGAAAAAAATATTACTTCAA

TACAAATACGAGCATTGCCAGCACCGGTTATACCATTATCAACGGCAAATATTTCTACTTCAACACCGATGGCATTA

TGCAGATTGGTGTGTTCAAAGTGCCGAATGGCTTTGAGTATTTCGCTCCGGCTAACACCCATAATAACAATATTGAG

GGCCAGGCGATCCTGTATCAGAATAAATTCCTGACACTGAACGGCAAAAAATACTATTTCGGCAGCGATTCAAAAGC

A

F1 amino acid sequence (SEQ ID NO: 4)

FNSENELDRDHLGFKIIDNKTYYYDEDSKLVKGLININNSLFYFDPIESNLVTGWQTINGKKYYFDINTGAASTSYK

IINGKHFYFNNNGVMQLGVFKGPDGFEYFAPANTQNNNIEGQAIVYQSKFLTLNGKKYYFDNDSKAVTGWRIINNEK

YYFNPNNAIAAVGLQVIDNNKYYFNPDTAIISKGWQTVNGSRYYFDTDTAIAFNGYKTIDGKHFYFDSDCVVKIGVF

SGSNGFEYFAPANTYNNNIEGQAIVYQSKFLTLNGKKYYFDNNSKAVTGWQTIDSKKYYFNTNTAEAATGWQTIDGK

KYYFNTNTAEAATGWQTIDGKKYYFNTNTSIASTGYTIINGKYFYFNTDGIMQIGVFKVPNGFEYFAPANTHNNNIE

GQAILYQNKFLTLNGKKYYFGSDSKA

F2 nucleic acid sequence (SEQ ID NO: 5)

GCCGAAGCAGCCACCGGCTGGCAAACCATTGATGGAAAAAAATATTACTTCAATACAAATACGAGCATTGCCAGCAC

CGGTTATACCATTATCAACGGCAAATATTTCTACTTCAACACCGATGGCATTATGCAGATTGGTGTGTTCAAAGTGC

CGAATGGCTTTGAGTATTTCGCTCCGGCTAACACCCATAATAACAATATTGAGGGCCAGGCGATCCTGTATCAGAAT

AAATTCCTGACACTGAACGGCAAAAAATACTATTTCGGCAGCGATTCAAAAGCAATTACAGGTTGGCAAACAATTGA

CGGGAAAAAGTACTATTTTAATCCGAACAATGCGATCGCAGCAACCCATCTGTGTACCATTAATAACGATAAATACT

ACTTTAGCTATGACGGCATCCTGCAGAATGGCTATATCACCATTGAACGCAACAACTTTTACTTTGATGCCAACAAC

GAAAGCAAAATGGTGACCGGTGTTTTTAAAGGCCCTAATGGCTTCGAATACTTCGCACCAGCGAATACGCATAACAA

TAACATCGAGGGTCAAGCGATTGTCTACCAGAATAAATTTCTGACTCTGAATGGTAAAAAATATTACTTCGATAATG

ATTCAAAAGCCGTGACCGGATGGCAAACTATCGATTCAAAAAAATACTACTTTAACCTGAACACCGCAGTTGCAGTT

-continued

ACAGGGTGGCAAACCATCGACGGTGAGAAATACTACTTCAATCTGAATACAGCCGAAGCCGCTACTGGATGGCAGAC

GATTGACGGAAAACGCTATTATTTTAATACCAACACCTATATTGCGAGCACAGGCTATACCATCATTAATGGTAAAC

ACTTCTACTTTAACACGGACGGTATCATGCAAATCGGCGTGTTTAAAGGCCCAGACGGTTTCGAGTACTTTGCGCCA

GCAAACACCCACAATAATAACATCGAAGGACAAGCCATCCTGTATCAAAACAAATTTCTGACGCTGAATGGCAAAAA

ATACTACTTCGGTAGTGATAGCAAAGCTGTTACAGGTCTGCGTACCATCGACGGAAAAAAATATTACTTTAATACTA

ACACGGCAGTGGCAGTGACGGGCTGGCAAACGATCAACGGGAAAAAATACTACTTCAACACCAACACGTATATTGCC

F2 amino acid sequence (SEQ ID NO: 6)

AEAATGWQTIDGKKYYFNTNTSIASTGYTIINGKYFYFNTDGIMQIGVFKVPNGFEYFAPANTHNNNIEGQAILYQN

KFLTLNGKKYYFGSDSKAITGWQTIDGKKYYFNPNNAIAATHLCTINNDKYYFSYDGILQNGYITIERNNFYFDANN

ESKMVTGVFKGPNGFEYFAPANTHNNNIEGQAIVYQNKFLTLNGKKYYFDNDSKAVTGWQTIDSKKYYFNLNTAVAV

TGWQTIDGEKYYFNLNTAEAATGWQTIDGKRYYFNTNTYIASTGYTIINGKHFYFNTDGIMQIGVFKGPDGFEYFAP

ANTHNNNIEGQAILYQNKFLTLNGKKYYFGSDSKAVTGLRTIDGKKYYFNTNTAVAVTGWQTINGKKYYFNTNTYIA

F3 nucleic acid sequence (SEQ ID NO: 7)

AAAGCCGTGACCGGATGGCAAACTATCGATTCAAAAAAATACTACTTTAACCTGAACACCGCAGTTGCAGTTACAGG

GTGGCAAACCATCGACGGTGAGAAATACTACTTCAATCTGAATACAGCCGAAGCCGCTACTGGATGGCAGACGATTG

ACGGAAAACGCTATTATTTTAATACCAACACCTATATTGCGAGCACAGGCTATACCATCATTAATGGTAAACACTTC

TACTTTAACACGGACGGTATCATGCAAATCGGCGTGTTTAAAGGCCCAGACGGTTTCGAGTACTTTGCGCCAGCAAA

CACCCACAATAATAACATCGAAGGACAAGCCATCCTGTATCAAAACAAATTTCTGACGCTGAATGGCAAAAAATACT

ACTTCGGTAGTGATAGCAAAGCTGTTACAGGTCTGCGTACCATCGACGGAAAAAAATATTACTTTAATACTAACACG

GCAGTGGCAGTGACGGGCTGGCAAACGATCAACGGGAAAAAATACTACTTCAACACCAACACGTATATTGCCTCAAC

CGGCTATACAATTATCAGCGGTAAACACTTTTATTTCAATACAGATGGGATCATGCAGATCGGAGTTTTCAAAGGAC

CTGATGGATTCGAGTATTTTGCTCCTGCGAATACCGATGCCAATAACATTGAGGGACAGGCAATTCGCTATCAGAAT

CGTTTTCTGTATCTGCACGATAATATTTATTATTTTGGCAATGATTCCAAAGCGGCAACCGGTTGGGCCACCATTGA

TGGTAATCGTTATTATTTTGAGCCGAATACCGCAATGGGTGCCAATGGTTATAAAACGATTGATAACAAAAACTTTT

ATTTTCGCAACGGCCTGCCGCAGATTGGCGTATTCAAAGGTCCTAACGGTTTTGAGTACTTCGCTCCAGCCAATACA

GATGCAAATAATATCGACGGCCAGGCCATCCGCTACCAGAACCGCTTCCTGCATCTGCTGGGTAAAATCTATTATTT

CGGCAACAACAGCAAAGCGGTAACTGGTTGGCAAACCATCAATAGCAAAGTGTATTATTTCATGCCGGATACAGCAA

TGGCAGCAGCCGGTGGTCTGTTTGAAATTGATGGTGTGATCTATTTCTTTGGTGTGGATGGTGTTAAAGCACCGGGT

ATTTATGGC

F3 amino acid sequence (SEQ ID NO: 8)

KAVTGWQTIDSKKYYFNLNTAVAVTGWQTIDGEKYYFNLNTAEAATGWQTIDGKRYYFNTNTYIASTGYTIINGKHF

YFNTDGIMQIGVFKGPDGFEYFAPANTHNNNIEGQAILYQNKFLTLNGKKYYFGSDSKAVTGLRTIDGKKYYFNTNT

AVAVTGWQTINGKKYYFNTNTYIASTGYTIISGKHFYFNTDGIMQIGVFKGPDGFEYFAPANTDANNIEGQAIRYQN

-continued

```
RFLYLHDNIYYFGNDSKAATGWATIDGNRYYFEPNTAMGANGYKTIDNKNFYFRNGLPQIGVFKGPNGFEYFAPANT

DANNIDGQAIRYQNRFLHLLGKIYYFGNNSKAVTGWQTINSKVYYFMPDTAMAAAGGLFEIDGVIYFFGVDGVKAPG

IYG
```

TABLE 1

| SEQ ID NO | Peptide Name | Amino Acid Sequence | Functional domain |
|---|---|---|---|
| 9 | RBD-P1 | GKYFYFNTDGIMQIGVFKVPNGFEYFAPANTHNNNI | Receptor-biding domain |
| 10 | RBD-P2 | DSKKYYFNLNTAVAVTGWQTIDGEKYYFNLNTAEA | Receptor-biding domain |
| 11 | RBD-P3 | ANTDANNIDGQAIRYQNRFLHLLGKIYYFGNNSKA | Receptor-biding domain |
| 12 | CdTx-CP | AKSYFLSDDGESILELNKYRIPERLKNKEKVKVTFIGHG | Peptidase |
| 13 | CdTx-GT1 | EKNLHFVWIGGEVSDIALEYIKQWADINAEYNIKLWYDSEA | Glycosyltransferase |
| 14 | CdTx-GT2 | GVYLDVDMLPGIHSDLFKTISRPSSIGLDRWEMIKLEA | Glycosyltransferase |
| 15 | CdTx-GT3 | GAYASAYYDFINLQENTIEKTLKASDLIEFKFPE | Glycosyltransferase |
| 16 | CdTx-TM1 | ILHDKATSVVNYFNHLSESKKYGPLKTEDDKILV | Transmembrane |
| 17 | CdTx-TM2 | LPNAPSRVFWWETGAVPGLRSLENDGTRL | Transmembrane |
| 18 | CdTx-TM3 | GAISKTSQKSIIHYKKDSKNILEFYNDSTLEFNSKDFIAEDI | Transmembrane |

In addition, polypeptides each containing a potential functional domain of tcdA are described herein. The amino acid sequences of these polypeptides are shown in Table 1.

A fusion protein containing one of the above-mentioned polypeptides and a lipidating sequence at the N-terminus can be produced in an *E. coli* expression system. The term "lipidating sequence" or "lipid leader sequence" refers to an amino acid sequence that (a) includes a first fragment that is at least 80% (85%, 90%, 95%, or 99%) identical to SP of Ag473 and a second fragment at least 80% (85%, 90%, 95%, or 99%) identical to Domain 1 of Ag473, the first fragment being at the N-terminus of the lipidating sequence, and (b) facilitates lipidation in *E. coli* of a polypeptide carrying the lipidating sequence at its N-terminus. In the lipidating sequence, the first fragment is linked to the second fragment either directly or via a peptide linker. Preferably, this sequence has a maximum length of 40-100 (e.g., 40-80) amino acids.

Ag473 is a *Neisseria Mengitidis* lipoprotein consisting of four domains, SP and Domains 1-3. Shown below is its amino acid sequence (SEQ ID NO:19) with the four domains identified:

(SEQ ID NO: 19)

Met Lys Lys Leu Leu Ile Ala Ala Met Met Ala Ala Ala Leu Ala Ala Cys Ser Gln Glu Ala Lys Gln Glu

Val Lys Glu Ala Val Gln Ala Val Glu Ser Asp Val Lys Asp Thr Ala Ala Ser Ala Ala Glu Ser Ala Ala

Ser Ala Val Glu Glu Ala Lys Asp Gln Val Lys Asp Ala Ala Ala Asp Ala Lys Ala Ser Ala Glu Glu

*Ala Val Thr Glu Ala Lys Glu Ala Val Thr Glu Ala Lys Glu Ala Val Thr Glu Ala Lys Glu Ala Val Thr Glu*

*Ala Ala Lys Asp Thr Leu Asn Lys Ala Ala Asp Ala Thr Gln Glu Ala Ala Asp Lys Met Lys Asp Ala Ala Lys*

SP: amino acid residues 1-17 (underlined)
Domain 1: amino acid residues 18-40 (highlited)
Domain 2: amino acid residues 41-71 (bold face)
Domain 3: amino acid residues 72-121(italic)

In one example, the lipidating sequence described herein includes residues 1-40 of SEQ ID NO:19, i.e., KKLLIAAM-MAAALAACSQEAKQEVKEAVQAVESDVKDTA (SEQ ID NO:20; the D1 domain of Ag473).

The lipidating sequence mentioned above can be linked to a target polypeptide by conventional recombinant technology to form a fusion protein, which is in lipidated form when expressed in *E. coli*. An example follows. A DNA fragment encoding the lipidating sequence and a DNA fragment encoding the target polypeptide are inserted into an expression vector, preferably carrying a strong promoter (e.g., T7, T5, T3, or SP6), to construct an expression plasmid. The strong promoter can be inducible, e.g., by isopropyl β-D-thiogalactoside (IPTG). The expression plasmid is then introduced into an *E. coli* host strain and positive transformants are cultured under suitable conditions for protein expression. It is preferred that the *E. coli* host strain be resistant to the toxic effects induced by over-expression of exogenous proteins. Such *E. coli* strains can be identified/generated by the methods described in U.S. Pat. No. 6,361,966. Examples of these *E. coli* strains include, but are not limited to, C43(DE3) (ECCC B96070445), C41(DE3) (ECCC B96070444), C0214(DE3), DK8(DE3)S (NCIMB 40885), and C2014(DE3) (NCIMB 40884).

The fusion protein thus expressed can be isolated from the *E. coli* host cells and its lipidation status can be confirmed via methods known in the art, e.g., immunoblotting with an anti-lipoprotein antibody or mass spectrometry.

Also described is an isolated nucleic acid molecule that contains a sequence encoding the above-described polypeptide or fusion protein or a complementary sequence thereof. Examples of the nucleic acid molecule include SEQ ID NO: 1 and its degenerate variants where one or more codons are replaced by other codons encoding the same residues.

The nucleic acid molecule described above can be used to express the polypeptide or fusion protein described herein, or as a DNA vaccine. One can operatively link the nucleic acid molecule to suitable regulatory sequences to generate an expression vector.

Examples of the vector include a plasmid, cosmid, or viral vector. The vector includes a nucleic acid in a form suitable for expression of the nucleic acid in a host cell. Preferably the vector includes one or more regulatory sequences operatively linked to the nucleic acid sequence to be expressed. A regulatory sequence includes promoters, enhancers, and other expression control elements (e.g., T7 promoter, cauliflower mosaic virus 35S promoter sequences or polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vector can be introduced into host cells to produce the polypeptide or fusion protein of this invention. The host cell is, for example, *Escherichia coli, B. pertussis, Bacillus*, VERO cell, *Haemophilus*, fungi, yeast, or CHO cell. The baculovirus expression system can also be used.

A host cell that contains the above-described nucleic acid can be generated. Examples include *E. coli* cells, insect cells (e.g., using baculovirus expression vectors), plant cells, yeast cells, and mammalian cells. See e.g., Goeddel, (1990) Gene Expression Technology: Methods in Enzymology 185, Academic Press, San Diego, Calif.

A polypeptide, fusion protein, or nucleic acid molecule described herein can be used to prepare an immunogenic composition (e.g., a vaccine) for generating antibodies and/or immune responses against *Clostridium difficile* in a subject (e.g., a human subject) susceptible to the pathogen or infected with the pathogen. Such compositions can be prepared, e.g., in the manners described below, or by any other methods known in the art.

For example, the composition can contain an effective amount of the polypeptide, fusion protein, or nucleic acid molecule, and a pharmaceutically acceptable carrier such as a phosphate buffered saline, a bicarbonate solution. The composition can also include an adjuvant. The carrier must be "acceptable" in the sense that it is compatible with the active ingredient of the composition and is not deleterious to the subject to be treated. The carrier is selected on the basis of the mode and route of administration and standard pharmaceutical practice. Suitable pharmaceutical carriers and diluents, as well as pharmaceutical necessities for their use, are described in Remington's Pharmaceutical Sciences. An adjuvant, e.g., a cholera toxin, *Escherichia coli* heat-labile enterotoxin (LT), liposome, immune-stimulating complex (ISCOM), or immunostimulatory sequences oligodeoxynucleotides (ISS-ODN), can also be included in the composition, if necessary. The composition can also include a polymer that facilitates in vivo delivery. See Audran R. et al. Vaccine 21:1250-5, 2003; and Denis-Mize et al. Cell Immunol., 225:12-20, 2003.

The polypeptide or fusion polypetide described herein can also be used as an adjuvant in an immunogenic composition containing another antigen, or linked to another protein (e.g., an antigen) or polysaccharide to generate a chimeric molecule. For example, the other antigen can be an antigenic protein or fragment thereof from a pathogen such as human papillomavirus (HPV), hepatitis C virus (HCV), Epstein-Barr virus (EBV), herpes simplex virus 1 (HSV-1), herpes simplex virus 2 (HSV-2), cytomegalovirus (CMV), respiratory syncytial virus (RSV), parainfluenza virus type 3 (PIV3), influenza viruses, dengue virus, west Nile virus, Norovirus, and SARS coronavirus.

The immunogenic composition can be formulated as a microparticle preparation, capsule preparation or liposome preparation. In addition, such immunogenic composition can include or be co-administered with a targeting molecule for delivery to specific cells of the immune system or to mucosal surfaces.

In addition, those polypeptides and fusion polypeptides described herein that contain one or more receptor binding sites within the RBD can be used as drug carriers. For example, a drug molecule (e.g., a polypeptide and a small molecule compound) can be conjugated to one of the polypeptides.

Also described herein is a kit for diagnosing Cd infection and associated diseases. The kit contains one or more antibodies that each specifically recognize tcdA. For example, an antibody of the kit can specifically bind to a polypeptide consisting of a sequence selected from the group consisting of SEQ ID NOs: 2, 4, 6, and 8-18. Such an antibody can be generated using methods known in the art. The kit can be used to detect the presence of tcdA in samples (e.g., blood samples) obtained from subjects suspected of being infected with Cd.

Any of the pharmaceutical compositions described above may be administered parenterally, e.g., subcutaneous injection or intramuscular injection. Alternatively, other modes of administration including suppositories and oral formulations may be desirable. For suppositories, binders and carriers may include, for example, polyalkalene glycols or triglycerides. Oral formulations may include normally employed incipients such as pharmaceutical grades of saccharine, cellulose, magnesium carbonate and the like. These compositions take the form of solutions, suspensions, tablets, pills, capsules, sustained release formulations or powders.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, etc. In a preferred embodiment, the subject is a human. In another embodiment, the subject is an experimental animal or animal suitable as a disease model.

The term "treating" as used herein refers to the application or administration of a composition including one or more active agents to a subject, who has a disease, a symptom of the disease, or a predisposition toward the disease, with the purpose to cure, heal, alleviate, relieve, alter, remedy, ameliorate, improve, or affect the disease, the symptoms of the disease, or the predisposition toward the disease. "An effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents.

The term "immune response" or "immunogenic response" refers to any reaction of the immune system in response to an antigen in a subject. Examples of an immune response in a vertebrate include, but are not limited to, antibody production, induction of cell-mediated immunity, and complement activation.

An "antigen" refers to a molecule containing one or more epitopes that will stimulate a host's immune system to make an antigen-specific immune response. The term "antigen" is used interchangeably with "immunogen." The term "epitope" as used herein refers to the site on an antigen to which a specific antibody molecule or a T-cell receptor binds. The term is used herein interchangeably with "antigenic determinant" or "antigenic determinant site."

An "antibody" refers to an immunoglobulin molecule or at least one immunologically active portion of an immunoglobulin molecule that has a specific amino acid sequence and binds only to an antigen or a group of antigens that are closely related. Examples of antibodies include IgG, IgM, IgA, IgD and IgE. Examples of immunologically active portions of immunoglobulin molecules include Fab and F(ab)'.sub.2 fragments which can be generated by treating the antibody with an enzyme such as pepsin. An antibody can be a monoclonal antibody or a polyclonal antibody.

An "adjuvant" refers to a substance added to an immunogenic composition, such as a vaccine, that while may or may not having any specific antigenic effect in itself, can stimulate the immune system and increase the immune response to the immunogenic composition. Examples of adjuvants include, but are not limited to, alum-precipitate, Freund's complete adjuvant, Freund's incomplete adjuvant, monophosphoryl-lipid A/trehalose dicorynomycolate adjuvant, water in oil emulsion containing *Corynebacterium parvum* and tRNA, and other substances that accomplish the task of increasing immune response by mimicking specific sets of evolutionarily conserved molecules including liposomes, lipopolysaccharide (LPS), molecular cages for antigen, components of bacterial cell walls, and endocytosed nucleic acids such as double-stranded RNA, single-stranded DNA, and unmethylated CpG dinucleotide-containing DNA. Other examples include cholera toxin, *E. coli* heat-labile enterotoxin, liposome, immune-stimulating complex (ISCOM), immunostimulatory sequences oligodeoxynucleotide, and aluminum hydroxide.

The specific example below is to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are incorporated herein by reference in their entirety.

Materials and Methods (1) Consensus Sequence Analysis

We rationally designed a sequence containing the C-terminal binding domain of *C. difficile* toxin A, a highly conserved and repetitive region, from NCBI database based on strain VPI10463 by a sequence alignment tool, i.e., Vector NTI Advance 11.5. This sequence as shown in FIG. 1 was analyzed by an online software for detection and alignment of repetitive protein sequences (found at the world wide web at ebi.ac.uk/Tools/pfa).

(2) Cloning and Plasmid Construction

The nucleotide sequence of TcdA RBD was optimized with *E. coli* expression codons and chemically synthesized for cloning, i.e., SEQ ID NO:1. In order to clone three fragments of TcdA RBD (RBD-F1, RBD-F2, and RBD-F3), PCR was used to amplify their coding regions with the following primes: F1 forward primer=TAA CAT ATG GGA TCC TTT AAT AGC GAG AAT GAA (SEQ ID NO:37), F1 reverse primer=ATT CTC GAG TGC TTT TGA ATC GCT GCC (SEQ ID NO:38), F2 forward=TAA CAT ATG GGA TCC GCC GAA GCA GCC ACC GGC (SEQ ID NO:39), F2 reverse primer=ATT CTC GAG GGC AAT ATA CGT GTT GGT (SEQ ID NO:40), F3 forward primer=TAA CAT ATG GGA TCC AAA GCC GTG ACC GGA TGG (SEQ ID NO:41), F3 reverse primer=ATT CTC GAG GCC ATA AAT ACC CGG TGC (SEQ ID NO:42). RBD-F1, RBD-F2, RBD-F3, and RBD were inserted into pET-22b vector (Novagen) by NdeI and XhoI restriction enzyme sites. The constructs were transformed into *E. coli* BL21 (+) RIL (Novagen) and JM109 (DE3) (Agilent technologies), respectively. RBD was fused with a lipid signal sequence at its 5'-end to obtain another construct, rlipo-RBD. This plasmid was transformed into *E. coli* C43 (DE3) (Lucigen).

The constructs and the sequences of the cloned inserts are described in more detail below (Underlined-restriction enzyme site; Regular font-RBD, F1, F2, or F3 sequence; Boldfaced—lipid leader sequence (LLS)).

A plasmid (pET22b_rRBD) was constructed by inserting a BamHI-RBD-XhoI frament into cloning plasmid pET-22b. See FIG. 2.

NdeI-BamHI-RBD-XhoI (SEQ ID NO: 21)

CATATGGGATCCTTTAATAGCGAGAATGAACTGGATCGTGATCATCTGGGCTTCAAAATCATCGATAATAAAACCTA

TTATTATGATGAAGATAGCAAACTGGTGAAAGGCCTGATTAACATTAACAACAGCCTGTTTTACTTCGATCCGATTG

AAAGCAATCTGGTTACCGGTTGGCAGACCATTAACGGCAAAAAATATTATTTTGATATTAATACCGGTGCAGCCAGC

ACCAGCTATAAAATTATCAACGGCAAGCATTTCTATTTCAATAATAATGGCGTGATGCAGCTGGGCGTTTTTAAAGG

TCCGGATGGTTTTGAATATTTTGCACCGGCAAATACCCAGAACAATAATATTGAAGGTCAGGCCATTGTGTATCAGA

-continued

GCAAATTTCTGACCCTGAACGGTAAAAAATACTACTTCGACAACGATAGCAAAGCAGTGACCGGTTGGCGCATTATT

AACAACGAGAAATATTATTTCAATCCGAATAACGCCATTGCAGCAGTTGGTCTGCAGGTTATTGACAACAATAAATA

TTACTTTAACCCGGACACCGCCATTATTAGCAAAGGCTGGCAGACCGTTAATGGTAGCCGTTATTATTTCGATACCG

ATACCGCGATTGCCTTTAATGGCTATAAAACCATCGACGGCAAACACTTCTATTTTGATAGCGATTGCGTGGTGAAA

ATTGGTGTTTTTAGCGGTAGCAACGGCTTTGAATACTTTGCCCCTGCCAATACCTACAACAACAACATCGAAGGCCA

GGCAATCGTTTATCAGTCAAAATTCCTGACGCTGAATGGGAAAAAATATTACTTTGACAATAACAGCAAAGCCGTTA

CGGGATGGCAGACAATTGATAGCAAAAAATACTACTTCAATACCAATACCGCAGAAGCAGCAACAGGTTGGCAGACG

ATCGATGGTAAAAAATATTATTTCAACACGAACACAGCCGAAGCAGCCACCGGCTGGCAAACCATTGATGGAAAAAA

ATATTACTTCAATACAAATACGAGCATTGCCAGCACCGGTTATACCATTATCAACGGCAAATATTTCTACTTCAACA

CCGATGGCATTATGCAGATTGGTGTGTTCAAAGTGCCGAATGGCTTTGAGTATTTCGCTCCGGCTAACACCCATAAT

AACAATATTGAGGGCCAGGCGATCCTGTATCAGAATAAATTCCTGACACTGAACGGCAAAAAATACTATTTCGGCAG

CGATTCAAAAGCAATTACAGGTTGGCAAACAATTGACGGGAAAAAGTACTATTTTAATCCGAACAATGCGATCGCAG

CAACCCATCTGTGTACCATTAATAACGATAAATACTACTTTAGCTATGACGGCATCCTGCAGAATGGCTATATCACC

ATTGAACGCAACAACTTTTACTTTGATGCCAACAACGAAAGCAAAATGGTGACCGGTGTTTTTAAAGGCCCTAATGG

CTTCGAATACTTCGCACCAGCGAATACGCATAACAATAACATCGAGGGTCAAGCGATTGTCTACCAGAATAAATTTC

TGACTCTGAATGGTAAAAAATATTACTTCGATAATGATTCAAAAGCCGTGACCGGATGGCAAACTATCGATTCAAAA

AAATACTACTTTAACCTGAACACCGCAGTTGCAGTTACAGGGTGGCAAACCATCGACGGTGAGAAATACTACTTCAA

TCTGAATACAGCCGAAGCCGCTACTGGATGGCAGACGATTGACGGAAAACGCTATTATTTTAATACCAACACCTATA

TTGCGAGCACAGGCTATACCATCATTAATGGTAAACACTTCTACTTTAACACGGACGGTATCATGCAAATCGGCGTG

TTTAAAGGCCCAGACGGTTTCGAGTACTTTGCGCCAGCAAACACCCACAATAATAACATCGAAGGACAAGCCATCCT

GTATCAAAACAAATTTCTGACGCTGAATGGCAAAAAATACTACTTCGGTAGTGATAGCAAAGCTGTTACAGGTCTGC

GTACCATCGACGGAAAAAAATATTACTTTAATACTAACACGGCAGTGGCAGTGACGGGCTGGCAAACGATCAACGGG

AAAAAATACTACTTCAACACCAACACGTATATTGCCTCAACCGGCTATACAATTATCAGCGGTAAACACTTTTATTT

CAATACAGATGGGATCATGCAGATCGGAGTTTTCAAAGGACCTGATGGATTCGAGTATTTTGCTCCTGCGAATACCG

ATGCCAATAACATTGAGGGACAGGCAATTCGCTATCAGAATCGTTTTCTGTATCTGCACGATAATATTTATTATTTT

GGCAATGATTCCAAAGCGGCAACCGGTTGGGCCACCATTGATGGTAATCGTTATTATTTTGAGCCGAATACCGCAAT

GGGTGCCAATGGTTATAAAACGATTGATAACAAAAACTTTTATTTTCGCAACGGCCTGCCGCAGATTGGCGTATTCA

AAGGTCCTAACGGTTTTGAGTACTTCGCTCCAGCCAATACAGATGCAAATAATATCGACGGCCAGGCCATCCGCTAC

CAGAACCGCTTCCTGCATCTGCTGGGTAAAATCTATTATTTCGGCAACAACAGCAAAGCGGTAACTGGTTGGCAAAC

CATCAATAGCAAAGTGTATTATTTCATGCCGGATACAGCAATGGCAGCAGCCGGTGGTCTGTTTGAAATTGATGGTG

TGATCTATTTCTTTGGTGTGGATGGTGTTAAAGCACCGGGTATTTATGGCCTCGAG

Amino acid sequence encoded by SEQ ID NO: 21

(SEQ ID NO: 22)

HMGSFNSENELDRDHLGFKIIDNKTYYYDEDSKLVKGLININNSLFYFDPIESNLVTGWQTINGKKYYFDINTGAAS

TSYKIINGKHFYFNNNGVMQLGVFKGPDGFEYFAPANTQNNNIEGQAIVYQSKFLTLNGKKYYFDNDSKAVTGWRII

NNEKYYFNPNNAIAAVGLQVIDNNKYYFNPDTAIISKGWQTVNGSRYYFDTDTAIAFNGYKTIDGKHFYFDSDCVVK

IGVFSGSNGFEYFAPANTYNNNIEGQAIVYQSKFLTLNGKKYYFDNNSKAVTGWQTIDSKKYYFNTNTAEAATGWQT

IDGKKYYFNTNTAEAATGWQTIDGKKYYFNTNTSIASTGYTIINGKYFYFNTDGIMQIGVFKVPNGFEYFAPANTHN

NNIEGQAILYQNKFLTLNGKKYYFGSDSKAITGWQTIDGKKYYFNPNNAIAATHLCTINNDKYYFSYDGILQNGYIT

IERNNFYFDANNESKMVTGVFKGPNGFEYFAPANTHNNNIEGQAIVYQNKFLTLNGKKYYFDNDSKAVTGWQTIDSK

KYYFNLNTAVAVTGWQTIDGEKYYFNLNTAEAATGWQTIDGKRYYFNTNTYIASTGYTIINGKHFYFNTDGIMQIGV

FKGPDGFEYFAPANTHNNNIEGQAILYQNKFLTLNGKKYYFGSDSKAVTGLRTIDGKKYYFNTNTAVAVTGWQTING

-continued

KKYYFNTNTYIASTGYTIISGKHFYFNTDGIMQIGVFKGPDGFEYFAPANTDANNIEGQAIRYQNRFLYLHDNIYYF

GNDSKAATGWATIDGNRYYFEPNTAMGANGYKTIDNKNFYFRNGLPQIGVFKGPNGFEYFAPANTDANNIDGQAIRY

QNRFLHLLGKIYYFGNNSKAVTGWQTINSKVYYFMPDTAMAAAGGLFEIDGVIYFFGVDGVKAPGIYGLE

A plasmid (pET22b_rlipo-RBD) was constructed by inserting a NdeI-LLS-BamHI-RBD-XhoI fragment into cloning plasmid pET-22b. See FIG. 2.

NdeI-LLS-BamHI-RBD-XhoI (SEQ ID NO: 23)

CATATGAAAAAATTATTGATTGCCGCAATGATGGCGGCTGCCTTGGCAGCTTGTTCGCAAGAAGCCAAACAGGAGGT

TAAGGAAGCGGTTCAAGCCGTTGAGTCCGATGTTAAAGACACTGCGGGATCCTTTAATAGCGAGAATGAACTGGATC

GTGATCATCTGGGCTTCAAAATCATCGATAATAAAACCTATTATTATGATGAAGATAGCAAACTGGTGAAAGGCCTG

ATTAACATTAACAACAGCCTGTTTTACTTCGATCCGATTGAAAGCAATCTGGTTACCGGTTGGCAGACCATTAACGG

CAAAAAATATTATTTTGATATTAATACCGGTGCAGCCAGCACCAGCTATAAAATTATCAACGGCAAGCATTTCTATT

TCAATAATAATGGCGTGATGCAGCTGGGCGTTTTTAAAGGTCCGGATGGTTTTGAATATTTTGCACCGGCAAATACC

CAGAACAATAATATTGAAGGTCAGGCCATTGTGTATCAGAGCAAATTTCTGACCCTGAACGGTAAAAAATACTACTT

CGACAACGATAGCAAAGCAGTGACCGGTTGGCGCATTATTAACAACGAGAAATATTATTTCAATCCGAATAACGCCA

TTGCAGCAGTTGGTCTGCAGGTTATTGACAACAATAAATATTACTTTAACCCGGACACCGCCATTATTAGCAAAGGC

TGGCAGACCGTTAATGGTAGCCGTTATTATTTCGATACCGATACCGCGATTGCCTTTAATGGCTATAAAACCATCGA

CGGCAAACACTTCTATTTTGATAGCGATTGCGTGGTGAAAATTGGTGTTTTTAGCGGTAGCAACGGCTTTGAATACT

TTGCCCCTGCCAATACCTACAACAACAACATCGAAGGCCAGGCAATCGTTTATCAGTCAAAATTCCTGACGCTGAAT

GGGAAAAAATATTACTTTGACAATAACAGCAAAGCCGTTACGGGATGGCAGACAATTGATAGCAAAAAATACTACTT

CAATACCAATACCGCAGAAGCAGCAACAGGTTGGCAGACGATCGATGGTAAAAAATATTATTTCAACACGAACACAG

CCGAAGCAGCCACCGGCTGGCAAACCATTGATGGAAAAAAATATTACTTCAATACAAATACGAGCATTGCCAGCACC

GGTTATACCATTATCAACGGCAAATATTTCTACTTCAACACCGATGGCATTATGCAGATTGGTGTGTTCAAAGTGCC

GAATGGCTTTGAGTATTTCGCTCCGGCTAACACCCATAATAACAATATTGAGGGCCAGGCGATCCTGTATCAGAATA

AATTCCTGACACTGAACGGCAAAAAATACTATTTCGGCAGCGATTCAAAAGCAATTACAGGTTGGCAAACAATTGAC

GGGAAAAAGTACTATTTTAATCCGAACAATGCGATCGCAGCAACCCATCTGTGTACCATTAATAACGATAAATACTA

CTTTAGCTATGACGGCATCCTGCAGAATGGCTATATCACCATTGAACGCAACAACTTTTACTTTGATGCCAACAACG

AAAGCAAAATGGTGACCGGTGTTTTTAAAGGCCCTAATGGCTTCGAATACTTCGCACCAGCGAATACGCATAACAAT

AACATCGAGGGTCAAGCGATTGTCTACCAGAATAAATTTCTGACTCTGAATGGTAAAAAATATTACTTCGATAATGA

TTCAAAAGCCGTGACCGGATGGCAAACTATCGATTCAAAAAAATACTACTTTAACCTGAACACCGCAGTTGCAGTTA

CAGGGTGGCAAACCATCGACGGTGAGAAATACTACTTCAATCTGAATACAGCCGAAGCCGCTACTGGATGGCAGACG

ATTGACGGAAAACGCTATTATTTTAATACCAACACCTATATTGCGAGCACAGGCTATACCATCATTAATGGTAAACA

CTTCTACTTTAACACGGACGGTATCATGCAAATCGGCGTGTTTAAAGGCCCAGACGGTTTCGAGTACTTTGCGCCAG

CAAACACCCACAATAATAACATCGAAGGACAAGCCATCCTGTATCAAAACAAATTTCTGACGCTGAATGGCAAAAAA

TACTACTTCGGTAGTGATAGCAAAGCTGTTACAGGTCTGCGTACCATCGACGGAAAAAAATATTACTTTAATACTAA

CACGGCAGTGGCAGTGACGGGCTGGCAAACGATCAACGGGAAAAAATACTACTTCAACACCAACACGTATATTGCCT

CAACCGGCTATACAATTATCAGCGGTAAACACTTTTATTTCAATACAGATGGGATCATGCAGATCGGAGTTTTCAAA

GGACCTGATGGATTCGAGTATTTTGCTCCTGCGAATACCGATGCCAATAACATTGAGGGACAGGCAATTCGCTATCA

GAATCGTTTTCTGTATCTGCACGATAATATTTATTATTTTGGCAATGATTCCAAAGCGGCAACCGGTTGGGCCACCA

TTGATGGTAATCGTTATTATTTTGAGCCGAATACCGCAATGGGTGCCAATGGTTATAAAACGATTGATAACAAAAAC

TTTTATTTTCGCAACGGCCTGCCGCAGATTGGCGTATTCAAAGGTCCTAACGGTTTTGAGTACTTCGCTCCAGCCAA

TACAGATGCAAATAATATCGACGGCCAGGCCATCCGCTACCAGAACCGCTTCCTGCATCTGCTGGGTAAAATCTATT

-continued

ATTTCGGCAACAACAGCAAAGCGGTAACTGGTTGGCAAACCATCAATAGCAAAGTGTATTATTTCATGCCGGATACA

GCAATGGCAGCAGCCGGTGGTCTGTTTGAAATTGATGGTGTGATCTATTTCTTTGGTGTGGATGGTGTTAAAGCACC

GGGTATTTATGGCCTCGAG

Amino acid sequence encoded by SEQ ID NO: 23

(SEQ ID NO: 24)

HMKKLLIAAMMAAALAACSQEAKQEVKEAVQAVESDVKDTAGSFNSENELDRDHLGFKIIDNKTYYYDEDSKLVKGL

ININNSLFYFDPIESNLVTGWQTINGKKYYFDINTGAASTSYKIINGKHFYFNNNGVMQLGVFKGPDGFEYFAPANT

QNNNIEGQAIVYQSKFLTLNGKKYYFDNDSKAVTGWRIINNEKYYFNPNNAIAAVGLQVIDNNKYYFNPDTAIISKG

WQTVNGSRYYFDTDTAIAFNGYKTIDGKHFYFDSDCVVKIGVFSGSNGFEYFAPANTYNNNIEGQAIVYQSKFLTLN

GKKYYFDNNSKAVTGWQTIDSKKYYFNTNTAEAATGWQTIDGKKYYFNTNTAEAATGWQTIDGKKYYFNTNTSIAST

GYTIINGKYFYFNTDGIMQIGVFKVPNGFEYFAPANTHNNNIEGQAILYQNKFLTLNGKKYYFGSDSKAITGWQTID

GKKYYFNPNNAIAATHLCTINNDKYYFSYDGILQNGYITIERNNFYFDANNESKMVTGVFKGPNGFEYFAPANTHNN

NIEGQAIVYQNKFLTLNGKKYYFDNDSKAVTGWQTIDSKKYYFNLNTAVAVTGWQTIDGEKYYFNLNTAEAATGWQT

IDGKRYYFNTNTYIASTGYTIINGKHFYFNTDGIMQIGVFKGPDGFEYFAPANTHNNNIEGQAILYQNKFLTLNGKK

YYFGSDSKAVTGLRTIDGKKYYFNTNTAVAVTGWQTINGKKYYFNTNTYIASTGYTIISGKHFYFNTDGIMQIGVFK

GPDGFEYFAPANTDANNIEGQAIRYQNRFLYLHDNIYYFGNDSKAATGWATIDGNRYYFEPNTAMGANGYKTIDNKN

FYFRNGLPQIGVFKGPNGFEYFAPANTDANNIDGQAIRYQNRFLHLLGKIYYFGNNSKAVTGWQTINSKVYYFMPDT

AMAAAGGLFEIDGVIYFFGVDGVKAPGIYGLE

A plasmid (pET22b_F1) was constructed by inserting a NdeI-F1-XhoI fragment into cloning plasmid pET-22b.

NdeI-BamHI-F1-XhoI (SEQ ID NO: 25)

CATATGGGATCCTTTAATAGCGAGAATGAACTGGATCGTGATCATCTGGGCTTCAAAATCATCGATAATAAAACCTA

TTATTATGATGAAGATAGCAAACTGGTGAAAGGCCTGATTAACATTAACAACAGCCTGTTTTACTTCGATCCGATTG

AAAGCAATCTGGTTACCGGTTGGCAGACCATTAACGGCAAAAAATATTATTTTGATATTAATACCGGTGCAGCCAGC

ACCAGCTATAAAATTATCAACGGCAAGCATTTCTATTTCAATAATAATGGCGTGATGCAGCTGGGCGTTTTTAAAGG

TCCGGATGGTTTTGAATATTTTGCACCGGCAAATACCCAGAACAATAATATTGAAGGTCAGGCCATTGTGTATCAGA

GCAAATTTCTGACCCTGAACGGTAAAAAATACTACTTCGACAACGATAGCAAAGCAGTGACCGGTTGGCGCATTATT

AACAACGAGAAATATTATTTCAATCCGAATAACGCCATTGCAGCAGTTGGTCTGCAGGTTATTGACAACAATAAATA

TTACTTTAACCCGGACACCGCCATTATTAGCAAAGGCTGGCAGACCGTTAATGGTAGCCGTTATTATTTCGATACCG

ATACCGCGATTGCCTTTAATGGCTATAAAACCATCGACGGCAAACACTTCTATTTTGATAGCGATTGCGTGGTGAAA

ATTGGTGTTTTTAGCGGTAGCAACGGCTTTGAATACTTTGCCCCTGCCAATACCTACAACAACAACATCGAAGGCCA

GGCAATCGTTTATCAGTCAAAATTCCTGACGCTGAATGGGAAAAAATATTACTTTGACAATAACAGCAAAGCCGTTA

CGGGATGGCAGACAATTGATAGCAAAAAATACTACTTCAATACCAATACCGCAGAAGCAGCAACAGGTTGGCAGACG

ATCGATGGTAAAAAATATTATTTCAACACGAACACAGCCGAAGCAGCCACCGGCTGGCAAACCATTGATGGAAAAAA

ATATTACTTCAATACAAATACGAGCATTGCCAGCACCGGTTATACCATTATCAACGGCAAATATTTCTACTTCAACA

CCGATGGCATTATGCAGATTGGTGTGTTCAAAGTGCCGAATGGCTTTGAGTATTTCGCTCCGGCTAACACCCATAAT

AACAATATTGAGGGCCAGGCGATCCTGTATCAGAATAAATTCCTGACACTGAACGGCAAAAAATACTATTTCGGCAG

CGATTCAAAAGCACTCGAG

Amino acid sequence encoded by SEQ ID NO: 25

(SEQ ID NO: 26)

HMGSFNSENELDRDHLGFKIIDNKTYYYDEDSKLVKGLININNSLFYFDPIESNLVTGWQTINGKKYYFDINTGAAS

TSYKIINGKHFYFNNNGVMQLGVFKGPDGFEYFAPANTQNNNIEGQAIVYQSKFLTLNGKKYYFDNDSKAVTGWRII

NNEKYYFNPNNAIAAVGLQVIDNNKYYFNPDTAIISKGWQTVNGSRYYFDTDTAIAFNGYKTIDGKHFYFDSDCVVK

IGVFSGSNGFEYFAPANTYNNNIEGQAIVYQSKFLTLNGKKYYFDNNSKAVTGWQTIDSKKYYFNTNTAEAATGWQT

-continued

IDGKKYYFNTNTAEAATGWQTIDGKKYYFNTNTSIASTGYTIINGKYFYFNTDGIMQIGVFKVPNGFEYFAPANTHN

NNIEGQAILYQNKFLTLNGKKYYFGSDSKALE

A plasmid (pET22b_lipo-F1) was constructed by inserting a NdeI-LLS-BamHI-F1-XhoI fragment into cloning plasmid pET-22b.

NdeI-LLS-BamHI-F1-XhoI (SEQ ID NO: 27)

CATATGAAAAAATTATTGATTGCCGCAATGATGGCGGCTGCCTTGGCAGCTTGTTCGCAAGAAGCCAAACAGGAGGT

TAAGGAAGCGGTTCAAGCCGTTGAGTCCGATGTTAAAGACACTGCGGGATCCTTTAATAGCGAGAATGAACTGGATC

GTGATCATCTGGGCTTCAAAATCATCGATAATAAAACCTATTATTATGATGAAGATAGCAAACTGGTGAAAGGCCTG

ATTAACATTAACAACAGCCTGTTTTACTTCGATCCGATTGAAAGCAATCTGGTTACCGGTTGGCAGACCATTAACGG

CAAAAAATATTATTTTGATATTAATACCGGTGCAGCCAGCACCAGCTATAAAATTATCAACGGCAAGCATTTCTATT

TCAATAATAATGGCGTGATGCAGCTGGGCGTTTTTAAAGGTCCGGATGGTTTTGAATATTTTGCACCGGCAAATACC

CAGAACAATAATATTGAAGGTCAGGCCATTGTGTATCAGAGCAAATTTCTGACCCTGAACGGTAAAAAATACTACTT

CGACAACGATAGCAAAGCAGTGACCGGTTGGCGCATTATTAACAACGAGAAATATTATTTCAATCCGAATAACGCCA

TTGCAGCAGTTGGTCTGCAGGTTATTGACAACAATAAATATTACTTTAACCCGGACACCGCCATTATTAGCAAAGGC

TGGCAGACCGTTAATGGTAGCCGTTATTATTTCGATACCGATACCGCGATTGCCTTTAATGGCTATAAAACCATCGA

CGGCAAACACTTCTATTTTGATAGCGATTGCGTGGTGAAAATTGGTGTTTTTAGCGGTAGCAACGGCTTTGAATACT

TTGCCCCTGCCAATACCTACAACAACAACATCGAAGGCCAGGCAATCGTTTATCAGTCAAAATTCCTGACGCTGAAT

GGGAAAAAATATTACTTTGACAATAACAGCAAAGCCGTTACGGGATGGCAGACAATTGATAGCAAAAAATACTACTT

CAATACCAATACCGCAGAAGCAGCAACAGGTTGGCAGACGATCGATGGTAAAAAATATTATTTCAACACGAACACAG

CCGAAGCAGCCACCGGCTGGCAAACCATTGATGGAAAAAAATATTACTTCAATACAAATACGAGCATTGCCAGCACC

GGTTATACCATTATCAACGGCAAATATTTCTACTTCAACACCGATGGCATTATGCAGATTGGTGTGTTCAAAGTGCC

GAATGGCTTTGAGTATTTCGCTCCGGCTAACACCCATAATAACAATATTGAGGGCCAGGCGATCCTGTATCAGAATA

AATTCCTGACACTGAACGGCAAAAAATACTATTTCGGCAGCGATTCAAAAGCACTCGAG

Amino acid sequence encoded by SEQ ID NO: 27

(SEQ ID NO: 28)

HMKKLLIAAMMAAALAACSQEAKQEVKEAVQAVESDVKDTAGSFNSENELDRDHLGFKIIDNKTYYYDEDSKLVKGL

ININNSLFYFDPIESNLVTGWQTINGKKYYFDINTGAASTSYKIINGKHFYFNNNGVMQLGVFKGPDGFEYFAPANT

QNNNIEGQAIVYQSKFLTLNGKKYYFDNDSKAVTGWRIINNEKYYFNPNNAIAAVGLQVIDNNKYYFNPDTAIISKG

WQTVNGSRYYFDTDTAIAFNGYKTIDGKHFYFDSDCVVKIGVFSGSNGFEYFAPANTYNNNIEGQAIVYQSKFLTLN

GKKYYFDNNSKAVTGWQTIDSKKYYFNTNTAEAATGWQTIDGKKYYFNTNTAEAATGWQTIDGKKYYFNTNTSIAST

GYTIINGKYFYFNTDGIMQIGVFKVPNGFEYFAPANTHNNNIEGQAILYQNKFLTLNGKKYYFGSDSKALE

A plasmid (pET22b_F2) was constructed by inserting a NdeI-F2-XhoI fragment into cloning plasmid pET-22b.

NdeI-BamHI-F2-XhoI (SEQ ID NO: 29)

CATATGGGATCCGCCGAAGCAGCCACCGGCTGGCAAACCATTGATGGAAAAAAATATTACTTCAATACAAATACGAG

CATTGCCAGCACCGGTTATACCATTATCAACGGCAAATATTTCTACTTCAACACCGATGGCATTATGCAGATTGGTG

TGTTCAAAGTGCCGAATGGCTTTGAGTATTTCGCTCCGGCTAACACCCATAATAACAATATTGAGGGCCAGGCGATC

CTGTATCAGAATAAATTCCTGACACTGAACGGCAAAAAATACTATTTCGGCAGCGATTCAAAAGCAATTACAGGTTG

GCAAACAATTGACGGGAAAAAGTACTATTTTAATCCGAACAATGCGATCGCAGCAACCCATCTGTGTACCATTAATA

ACGATAAATACTACTTTAGCTATGACGGCATCCTGCAGAATGGCTATATCACCATTGAACGCAACAACTTTTACTTT

GATGCCAACAACGAAAGCAAAATGGTGACCGGTGTTTTTAAAGGCCCTAATGGCTTCGAATACTTCGCACCAGCGAA

TACGCATAACAATAACATCGAGGGTCAAGCGATTGTCTACCAGAATAAATTTCTGACTCTGAATGGTAAAAAATATT

ACTTCGATAATGATTCAAAAGCCGTGACCGGATGGCAAACTATCGATTCAAAAAAATACTACTTTAACCTGAACACC

-continued

GCAGTTGCAGTTACAGGGTGGCAAACCATCGACGGTGAGAAATACTACTTCAATCTGAATACAGCCGAAGCCGCTAC

TGGATGGCAGACGATTGACGGAAAACGCTATTATTTTAATACCAACACCTATATTGCGAGCACAGGCTATACCATCA

TTAATGGTAAACACTTCTACTTTAACACGGACGGTATCATGCAAATCGGCGTGTTTAAAGGCCCAGACGGTTTCGAG

TACTTTGCGCCAGCAAACACCCACAATAATAACATCGAAGGACAAGCCATCCTGTATCAAAACAAATTTCTGACGCT

GAATGGCAAAAAATACTACTTCGGTAGTGATAGCAAAGCTGTTACAGGTCTGCGTACCATCGACGGAAAAAAATATT

ACTTTAATACTAACACGGCAGTGGCAGTGACGGGCTGGCAAACGATCAACGGGAAAAAATACTACTTCAACACCAAC

ACGTATATTGCCCTCGAG

Amino acid sequence encoded by SEQ ID NO:29

(SEQ ID NO: 30)

HMGSAEAATGWQTIDGKKYYFNTNTSIASTGYTIINGKYFYFNTDGIMQIGVFKVPNGFEYFAPANTHNNNIEGQAI

LYQNKFLTLNGKKYYFGSDSKAITGWQTIDGKKYYFNPNNAIAATHLCTINNDKYYFSYDGILQNGYITIERNNFYF

DANNESKMVTGVFKGPNGFEYFAPANTHNNNIEGQAIVYQNKFLTLNGKKYYFDNDSKAVTGWQTIDSKKYYFNLNT

AVAVTGWQTIDGEKYYFNLNTAEAATGWQTIDGKRYYFNTNTYIASTGYTIINGKHFYFNTDGIMQIGVFKGPDGFE

YFAPANTHNNNIEGQAILYQNKFLTLNGKKYYFGSDSKAVTGLRTIDGKKYYFNTNTAVAVTGWQTINGKKYYFNTN

TYIALE

A plasmid (pET22b_lipo-F2) was constructed by inserting a NdeI-LLS-BamHI-F2-XhoI fragment into cloning plasmid pET-22b.

NdeI-LLS-BamHI-F2-XhoI (SEQ ID NO: 31)

CATATGAAAAAATTATTGATTGCCGCAATGATGGCGGCTGCCTTGGCAGCTTGTTCGCAAGAAGCCAAACAGGAGGT

TAAGGAAGCGGTTCAAGCCGTTGAGTCCGATGTTAAAGACACTGCGGGATCCGCCGAAGCAGCCACCGGCTGGCAAA

CCATTGATGGAAAAAAATATTACTTCAATACAAATACGAGCATTGCCAGCACCGGTTATACCATTATCAACGGCAAA

TATTTCTACTTCAACACCGATGGCATTATGCAGATTGGTGTGTTCAAAGTGCCGAATGGCTTTGAGTATTTCGCTCC

GGCTAACACCCATAATAACAATATTGAGGGCCAGGCGATCCTGTATCAGAATAAATTCCTGACACTGAACGGCAAAA

AATACTATTTCGGCAGCGATTCAAAAGCAATTACAGGTTGGCAAACAATTGACGGGAAAAAGTACTATTTTAATCCG

AACAATGCGATCGCAGCAACCCATCTGTGTACCATTAATAACGATAAATACTACTTTAGCTATGACGGCATCCTGCA

GAATGGCTATATCACCATTGAACGCAACAACTTTTACTTTGATGCCAACAACGAAAGCAAAATGGTGACCGGTGTTT

TTAAAGGCCCTAATGGCTTCGAATACTTCGCACCAGCGAATACGCATAACAATAACATCGAGGGTCAAGCGATTGTC

TACCAGAATAAATTTCTGACTCTGAATGGTAAAAAATATTACTTCGATAATGATTCAAAAGCCGTGACCGGATGGCA

AACTATCGATTCAAAAAAATACTACTTTAACCTGAACACCGCAGTTGCAGTTACAGGGTGGCAAACCATCGACGGTG

AGAAATACTACTTCAATCTGAATACAGCCGAAGCCGCTACTGGATGGCAGACGATTGACGGAAAACGCTATTATTTT

AATACCAACACCTATATTGCGAGCACAGGCTATACCATCATTAATGGTAAACACTTCTACTTTAACACGGACGGTAT

CATGCAAATCGGCGTGTTTAAAGGCCCAGACGGTTTCGAGTACTTTGCGCCAGCAAACACCCACAATAATAACATCG

AAGGACAAGCCATCCTGTATCAAAACAAATTTCTGACGCTGAATGGCAAAAAATACTACTTCGGTAGTGATAGCAAA

GCTGTTACAGGTCTGCGTACCATCGACGGAAAAAAATATTACTTTAATACTAACACGGCAGTGGCAGTGACGGGCTG

GCAAACGATCAACGGGAAAAAATACTACTTCAACACCAACACGTATATTGCCCTCGAG

Amino acid sequence encoded by SEQ ID NO:31

(SEQ ID NO: 32)

HMKKLLIAAMMAAALAACSQEAKQEVKEAVQAVESDVKDTAGSAEAATGWQTIDGKKYYFNTNTSIASTGYTIINGK

YFYFNTDGIMQIGVFKVPNGFEYFAPANTHNNNIEGQAILYQNKFLTLNGKKYYFGSDSKAITGWQTIDGKKYYFNP

NNAIAATHLCTINNDKYYFSYDGILQNGYITIERNNFYFDANNESKMVTGVFKGPNGFEYFAPANTHNNNIEGQAIV

YQNKFLTLNGKKYYFDNDSKAVTGWQTIDSKKYYFNLNTAVAVTGWQTIDGEKYYFNLNTAEAATGWQTIDGKRYYF

NTNTYIASTGYTIINGKHFYFNTDGIMQIGVFKGPDGFEYFAPANTHNNNIEGQAILYQNKFLTLNGKKYYFGSDSK

AVTGLRTIDGKKYYFNTNTAVAVTGWQTINGKKYYFNTNTYIALE

-continued

A plasmid (pET22b_F3) was constructed by inserting a NdeI-F3-XhoI fragment into a standard cloning plasmid pET-22b.

NdeI-BamHI-F3-XhoI (SEQ ID NO: 33)

CATATGGGATCCAAAGCCGTGACCGGATGGCAAACTATCGATTCAAAAAAATACTACTTTAACCTGAACACCGCAGT

TGCAGTTACAGGGTGGCAAACCATCGACGGTGAGAAATACTACTTCAATCTGAATACAGCCGAAGCCGCTACTGGAT

GGCAGACGATTGACGGAAAACGCTATTATTTTAATACCAACACCTATATTGCGAGCACAGGCTATACCATCATTAAT

GGTAAACACTTCTACTTTAACACGGACGGTATCATGCAAATCGGCGTGTTTAAAGGCCCAGACGGTTTCGAGTACTT

TGCGCCAGCAAACACCCACAATAATAACATCGAAGGACAAGCCATCCTGTATCAAAACAAATTTCTGACGCTGAATG

GCAAAAAATACTACTTCGGTAGTGATAGCAAAGCTGTTACAGGTCTGCGTACCATCGACGGAAAAAAATATTACTTT

AATACTAACACGGCAGTGGCAGTGACGGGCTGGCAAACGATCAACGGGAAAAAATACTACTTCAACACCAACACGTA

TATTGCCTCAACCGGCTATACAATTATCAGCGGTAAACACTTTTATTTCAATACAGATGGGATCATGCAGATCGGAG

TTTTCAAAGGACCTGATGGATTCGAGTATTTTGCTCCTGCGAATACCGATGCCAATAACATTGAGGGACAGGCAATT

CGCTATCAGAATCGTTTTCTGTATCTGCACGATAATATTTATTATTTTGGCAATGATTCCAAAGCGGCAACCGGTTG

GGCCACCATTGATGGTAATCGTTATTATTTTGAGCCGAATACCGCAATGGGTGCCAATGGTTATAAAACGATTGATA

ACAAAAACTTTTATTTTCGCAACGGCCTGCCGCAGATTGGCGTATTCAAAGGTCCTAACGGTTTTGAGTACTTCGCT

CCAGCCAATACAGATGCAAATAATATCGACGGCCAGGCCATCCGCTACCAGAACCGCTTCCTGCATCTGCTGGGTAA

AATCTATTATTTCGGCAACAACAGCAAAGCGGTAACTGGTTGGCAAACCATCAATAGCAAAGTGTATTATTTCATGC

CGGATACAGCAATGGCAGCAGCCGGTGGTCTGTTTGAAATTGATGGTGTGATCTATTTCTTTGGTGTGGATGGTGTT

AAAGCACCGGGTATTTATGGCCTCGAG

Amino acid sequence encoded by SEQ ID NO: 33

(SEQ ID NO: 34)

HMGSKAVTGWQTIDSKKYYFNLNTAVAVTGWQTIDGEKYYFNLNTAEAATGWQTIDGKRYYFNTNTYIASTGYTIIN

GKHFYFNTDGIMQIGVFKGPDGFEYFAPANTHNNNIEGQAILYQNKFLTLNGKKYYFGSDSKAVTGLRTIDGKKYYF

NTNTAVAVTGWQTINGKKYYFNTNTYIASTGYTIISGKHFYFNTDGIMQIGVFKGPDGFEYFAPANTDANNIEGQAI

RYQNRFLYLHDNIYYFGNDSKAATGWATIDGNRYYFEPNTAMGANGYKTIDNKNFYFRNGLPQIGVFKGPNGFEYFA

PANTDANNIDGQAIRYQNRFLHLLGKIYYFGNNSKAVTGWQTINSKVYYFMPDTAMAAAGGLFEIDGVIYFFGVDGV

KAPGIYGLE

A plasmid (pET22b_lipo-F3) was constructed by inserting a NdeI-LLS-BamHI-F3-XhoI fragment into a standard cloning plasmid pET-22b.

NdeI-LLS-BamHI-F3-XhoI (SEQ ID NO: 35)

CATATGAAAAAATTATTGATTGCCGCAATGATGGCGGCTGCCTTGGCAGCTTGTTCGCAAGAAGCCAAACAGGAGGT

TAAGGAAGCGGTTCAAGCCGTTGAGTCCGATGTTAAAGACACTGCGGGATCCAAAGCCGTGACCGGATGGCAAACTA

TCGATTCAAAAAAATACTACTTTAACCTGAACACCGCAGTTGCAGTTACAGGGTGGCAAACCATCGACGGTGAGAAA

TACTACTTCAATCTGAATACAGCCGAAGCCGCTACTGGATGGCAGACGATTGACGGAAAACGCTATTATTTTAATAC

CAACACCTATATTGCGAGCACAGGCTATACCATCATTAATGGTAAACACTTCTACTTTAACACGGACGGTATCATGC

AAATCGGCGTGTTTAAAGGCCCAGACGGTTTCGAGTACTTTGCGCCAGCAAACACCCACAATAATAACATCGAAGGA

CAAGCCATCCTGTATCAAAACAAATTTCTGACGCTGAATGGCAAAAAATACTACTTCGGTAGTGATAGCAAAGCTGT

TACAGGTCTGCGTACCATCGACGGAAAAAAATATTACTTTAATACTAACACGGCAGTGGCAGTGACGGGCTGGCAAA

CGATCAACGGGAAAAAATACTACTTCAACACCAACACGTATATTGCCTCAACCGGCTATACAATTATCAGCGGTAAA

CACTTTTATTTCAATACAGATGGGATCATGCAGATCGGAGTTTTCAAAGGACCTGATGGATTCGAGTATTTTGCTCC

TGCGAATACCGATGCCAATAACATTGAGGGACAGGCAATTCGCTATCAGAATCGTTTTCTGTATCTGCACGATAATA

TTTATTATTTTGGCAATGATTCCAAAGCGGCAACCGGTTGGGCCACCATTGATGGTAATCGTTATTATTTTGAGCCG

AATACCGCAATGGGTGCCAATGGTTATAAAACGATTGATAACAAAAACTTTTATTTTCGCAACGGCCTGCCGCAGAT

-continued

TGGCGTATTCAAAGGTCCTAACGGTTTTGAGTACTTCGCTCCAGCCAATACAGATGCAAATAATATCGACGGCCAGG

CCATCCGCTACCAGAACCGCTTCCTGCATCTGCTGGGTAAAATCTATTATTTCGGCAACAACAGCAAAGCGGTAACT

GGTTGGCAAACCATCAATAGCAAAGTGTATTATTTCATGCCGGATACAGCAATGGCAGCAGCCGGTGGTCTGTTTGA

AATTGATGGTGTGATCTATTTCTTTGGTGTGGATGGTGTTAAAGCACCGGGTATTTATGGCCTCGAG

Amino acid sequence encoded by SEQ ID NO: 35

(SEQ ID NO: 36)

HMKKLLIAAMMAAALAACSQEAKQEVKEAVQAVESDVKDTAGSKAVTGWQTIDSKKYYFNLNTAVAVTGWQTIDGEK

YYFNLNTAEAATGWQTIDGKRYYFNTNTYIASTGYTIINGKHFYFNTDGIMQIGVFKGPDGFEYFAPANTHNNNIEG

QAILYQNKFLTLNGKKYYFGSDSKAVTGLRTIDGKKYYFNTNTAVAVTGWQTINGKKYYFNTNTYIASTGYTIISGK

HFYFNTDGIMQIGVFKGPDGFEYFAPANTDANNIEGQAIRYQNRFLYLHDNIYYFGNDSKAATGWATIDGNRYYFEP

NTAMGANGYKTIDNKNFYFRNGLPQIGVFKGPNGFEYFAPANTDANNIDGQAIRYQNRFLHLLGKIYYFGNNSKAVT

GWQTINSKVYYFMPDTAMAAAGGLFEIDGVIYFFGVDGVKAPGIYGLE (3) Recombinant Protein Expression and Purification rRBD, F1, F2, and F3 polypeptides (i.e., including SEQ ID NOs:2, 4, 6, 8, respectively) each fused to a C-terminal polyhistidine tag were expressed in *E. coli* BL21 (+) RIL after 1 mM isopropyl-β-D-thiogalacto-pyranoside (IPTG) induction, and cultured in LB medium with 100 ug/ml ampicillin at 20° C. for 16 hours. Cells from 2 liters of cultures were harvested by centrifugation and stored at −20° C. before being suspended in 50 mM sodium phosphate buffer, pH 7.2 containing 250 mM NaCl and 5 mM imidazol. The cells were disrupted by French Press and collected supernatant was applied to nickel resin for purification. The RBD-truncated proteins were dialyzed against 1×PBS, pH 7.2 containing 50 mM Arg and 10% glycerol. rRBD was dialyzed against 1×PBS, pH 7.2 containing 10% glycerol. The four proteins were passed through E membranes for endotoxin removal. rlipo-RBD fused to C-terminal polyhistidine tag was purified according to the procedure used for recombinant lipoprotein purification described in Tseng and Leng (Appl Microbiol Biotechnol. 2012; 93:1539-1552). Briefly, rlipo-RBD expressed in *E. coli* C43 (DE3) was extracted from pellet with 50 mM Tris-C1, pH8.0 containing 0.5% Triton X-100 after cell lysis. The extraction was purified by two steps affinity chromatograph. First, nickel resin was used for separation. Second, the eluent obtained after dialysis to remove imidazol was applied to immobilized metal affinity chromatography (IMAC) (GE) charged with copper ion for LPS remove.

(4) Peptide Synthesis

All peptides were purchased from NIIDV peptide synthesis core facility in Taiwan.

(5) SDS-PAGE and Western Blot Analysis

Protein samples were quantified by BCA Protein Assay Kit (Thermo Pierce) before being loaded onto 10% SDS-PAGE. After a sample was transferred to PVDF (GE), PVDF membrane was blocked by 5% milk for 1 hour. The membrane was then inoculated with anti-his tag and specific anti-CD toxin A antibodies in PBS containing 1% milk and 0.05% Tween-20 for 1 hour. Finally, the membrane was incubated with HRP-conjugated secondary antibodies (GeneTex) in PBS containing 1% milk and 0.05% Tween-20 for 1 hour. The membrane was developed using Luminata Crescendo substrate (Merck Millipore).

(6) In Vitro Neutralization Assay Using Vero Cells

Vero cells were maintained in 75 T flask (Corning) containing Virus production-serum free medium (VP-SFM) (Invitrogen)/4 mM glutamine at 37° C., 5% $CO_2$, until the cells were confluent. $2\times10^4$ cells were seeded into 96-well plates at 37° C., 5% $CO_2$, overnight and replaced with fresh VP-SFM. Serially two fold dilutions of serum samples from mice immunized with or without rRBD or rlipo-RBD were mixed with Toxin A by equal volume and incubated at room temperature for 1 hour. The mixture was added into 96-well plates to arrive at 16 ng/ml toxin A and incubated at 37° C., 5% $CO_2$, for 24 hours. Toxin A neutralizing titer was determined by 100% cell rounding and cell image was captured by camera on the microscope.

(7) Animal Immunization and tcdA Challenge Model

BALB/c mice and Syrian golden hamsters were purchased from the National Animal Center in Taiwan and held in the Animal Center of the NHRI. BALB/c mice were immunized three times with 0.3, 3.0 and 30 μg rRBD and rlipo-RBD every two weeks and hamsters were immunized three times with 10 μg rRBD and rlipo-RBD every two weeks. Before immunization, mice and hamsters were bled from facial vein and orbital sinus sampling, respectively, and then collected serum to calculate antigen-specific IgG and IgA titer by ELISA. Toxin A challenge was administrated as previously described by Sergin S S et al., 2012. Vaccine 30:1492-1501. Briefly, BALB/c mice were immunized with 0.3 and 3 μg rRBD and rlipo-RBD three times via intramuscular injection every two weeks. Toxin A challenge was performed at fifth week via intraperitoneal injection of 150 ng toxin A (NativeAntigen Inc.). Animal mortality was continuously observed every six hours by lab personal.

(8) Peptides Immunization

Guinea pigs purchased from National Animal Center in Taiwan were immunized with three peptides only and mixture formulated with incomplete Freund's adjuvant (IFA) (Sigma) by three times of subcutaneous injection every month and held in the Animal Center of the NHRI.

(9) Cell Staining and Flow Cytometry

Vero cells on 75 T flask containing Virus production-serum free medium (VP-SFM)/4 mM glutamine were confluent at 37° C., 5% $CO_2$. An aliquot of $5\times10^5$ cells was performed to inoculate with 1 μg specific monoclonal antibodies (GeneTex) and anti-his tag antibodies (AbD Serotec) on ice for 30 min. After washing twice, FITC-conjugated secondary antibodies (Sigma) were treated on ice for surface staining for 30 min. Before flowcytometry analysis, propidium iodide (PI) was carried out for a cell viability marker to exclude dead cells.

(10) Hemagglutination Assay

Hemagglutinin (HA) activity assay was performed as described by Wren et al. (Infect. Immun. 1991, 59:3151-3155.) In brief, 250 pMoles of either rRBD, or rRBD-F1, or rRBD-F2 or rRBD-F3 in 254 of PBS were serially two-fold diluted in PBS and placed in the wells of a 96-wells round-bottom plate. 25 μL of a suspension of 2% rabbit erythrocyte re-washed with PBS to remove serum contamination were added into the wells at a 1 to 1 ratio. The mixtures were incubated at 4° C. overnight. HA activity was calculated by visual scoring.

(11) ELISA

After antigen coating in ELISA plates (Costar) overnight, 5% BSA (Calbiochem) in PBS was performed to block plates. The plates with serially diluted sera were incubated at room temperature for 2 hours. HRP-conjugated IgG (KPL) and IgA (Invitrogen) specific antibodies in PBS containing 1% BSA were treated and inoculated at room temperature for 1 hour. The plates were treated with TMB microwell peroxidase substrate (KPL) at room temperature in the dark for 20 min. Spectrophotometer was performed to calculate sera titer by detection of $OD_{450nm}$ absorbance.

(12) Mucosal Immunization

Female C57BL/6 mice at age of 6 to 8 weeks were purchased from National Animal Center in Taiwan and held in the Animal Center of the NHRI. All experiments were performed by following the guidelines of the animal center of NHRI. 6 mice of each group received three intranasal immunizations with 2 μg or 10 μg of tcdA-RBD formulated with 10 μg of ovalbumin (OVA) every two weeks. 10 μg of OVA formulated with 1 μg of cholera toxin and PBS, respectively, were used as positive and negative controls of the intranasal study. Mice were bled 1 week prior to every immunization via facial vein. Each antigen was prepared in a total volume of 40 μL for the intranasal administration. 7 days after the last immunization, mice were bled and sacrificed to collect their broncho-alveolar lavage fluid (BALF) and fecal in the small intestine. The BALF was administrated by washing with 1 mL PBS containing Protease Inhibitor Cooktail Set III (Calbiochem, Darmstadt, Germany). Fecal was resuspended in the same buffer as the BALF wash at 1 mg/ml. Both the BALF wash and fecal solution remained on ice until being stored at −20° C. Levels of IgG and IgA of mouse sera and IgA of BALF and fecal were determined by ELISA.

(13) Dendritic Cell (DC) Maturation Surface Markers and Cytokines Analysis

Analysis of DC maturation was performed in vitro as previously described in Takeuchi et al., (J. Immunol (2002) 169:10-14). C57B/6 mice were purchased from National Animal Center in Taiwan and held in the Animal Center at the NHRI. In brief, bone marrow-derived DCs (BMDCs) were collected from the tibiae of 6 to 8-week old female C57B/6. Bone marrow cells were isolated by vigorously washing with LCM (RPMI 1640 containing 1% antibiotics with penicillin and streptomycin, 10% heat-inactivated FBS, 50 μM β-mercaptoethanol, and 50 mM HEPES) and treated with lysis buffer to remove erythrocytes. BMDCs were re-suspended in LCM at $2\times10^6$ cells/mL and treated with 20 ng/mL recombinant granulocyte macrophage colony stimulating factor (MoGM-CSF) on days 0 and 3. An aliquot of suspended BMDCs equivalent to $2\times10^6$/mL was seeded into 24-wells plates at day 6. Different concentrations of tcdA-RBD combined with or without 10 ng/mL of polymyxin B were added. LPS and toxin A served as positive controls. After 16 to 18 hr inoculation, BMDCs were analyzed by flow cytometer (FACSCalibur, BD Biosciences, Franklin Lakes, N.J., USA) to evaluate up-regulation of cell surface markers. In order to exclude immature DCs, composed of 50% of total cell population, CD11c+ cell population was gated for surface marker staining with specific monoclonal antibodies to CD-40, CD-80, CD-86, and MHC-II. In addition, after indicated treatment, cell culture medium was collected to analyze the expression of cytokines including IL-6, IL-12p40, and TNF-α which were typically secreted from activated DCs.

(14) Adjuvant Effect of tcdA-RBD

The immunization protocol for measuring the systemic adjuvant effect of tcdA-RBD is described below. Four cohorts of 6 BALB/c mice were each immunized with 2 μg of ovalbumin (OVA) (Sigma, US) formulated with 3 μg or 10 μg of tcdA-RBD, RBD-F1, RBD-F2, RBD-F3, or aluminum hydroxide via intramuscular injection. Mice receiving 2 μg of OVA only were used as immunization controls. The mice were given three immunizations with at 14-day intervals and bled before each injection by facial vein sampling. The blood samples were collected and is inactivated at 56° C. for 30 minutes, and then stored at −80° C. for future analysis.

(15) Fluorescence-Activated Cell Sorting (FACS) Analysis

Vero cells in 75 T flask containing VP-SFM/4 mM glutamine was 80% confluent at 37° C., 5% CO2. An aliquot of $5\times10^5$ cells was mixed with 1 μg of specific monoclonal antibodies (PCG-4) (GeneTex) and anti-his tag antibodies (AbD Serotec) and incubated on ice for 30 min. After washing twice, FITC-conjugated secondary antibodies (Sigma) were add and the sample was incubated on ice for 30 min for surface staining. Before flow cytometry analysis, propidium iodide (PI) was added as a cell viability marker to exclude dead cells.

Results (1) Rational Design of DNA Sequences Coding for tcdA-RBD

A clone encoding the designated tcdA-RBD was generated by linking cDNA fragments generated from several synthetic DNA fragments with sequences derived from consensus sequence analysis as described above. The nucleic acid sequences encoding tcdA-RBD with lipo-box sequences and individual tcdA-RBD fragments were subcloned into pET-22b to produce pET-22b-rlipo-RBD, pET-22b-rRBD-F1, pET-22b-rRBD-F2 and pET-22b-rRBD-F3 and used to transform *E. coli* BL21(+)RIL and/or JM109 (DE3) as described above. Plasmid DNA was prepared for sequence confirmation from two individual colonies of *E. coli* JM109(DE3) containing individual plasmid. Sequencing was performed on an ABI DNA sequencer model 370A using dye-terminator chemistry and oligonucleotide primers which had been synthesized on an ABI DNA synthesizer model 380B, and purified by chromatography. Nucleotide sequence analysis of the tcdA-RBD and its fragments revealed 1 or 2 mismatched base pairs. The mismatch base pairs were corrected by site-specific mutagenesis.

Figure 3:
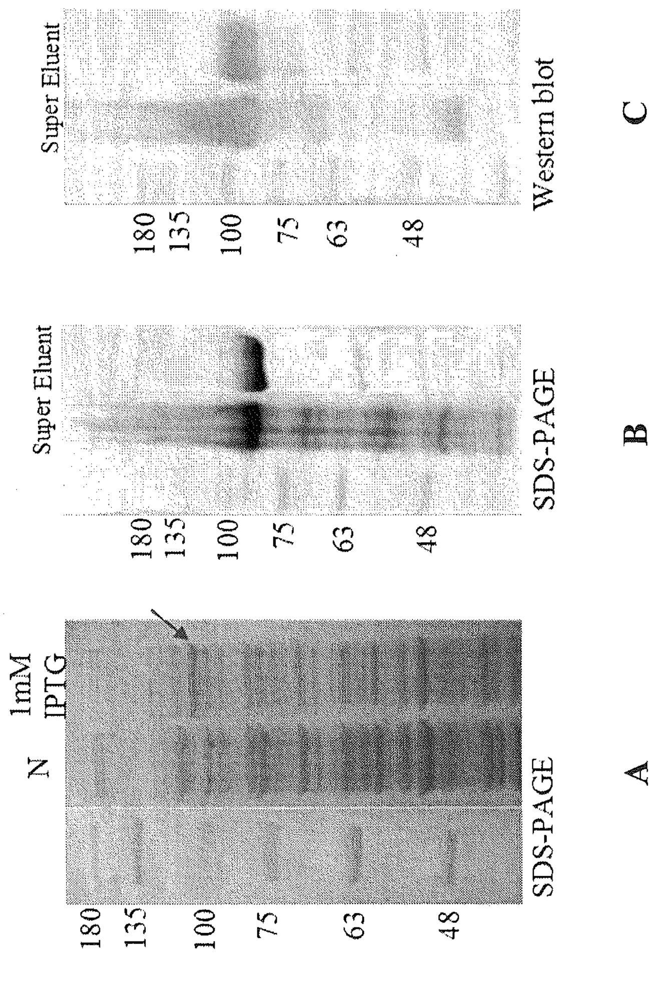
FIG. 3 is a set of SDS-PAGE (Panels A and B) and Western blot (Panel C) showing analysis of recombinant tcdA-RBD (rRBD) purified using Ni-affinity column from *E. coli* lysate. Molecular weight markers are 35 kDa, 48 kDa, 63 kDa, 75 kDa, 100 kDa, and 135 kDa.
Figure 4:
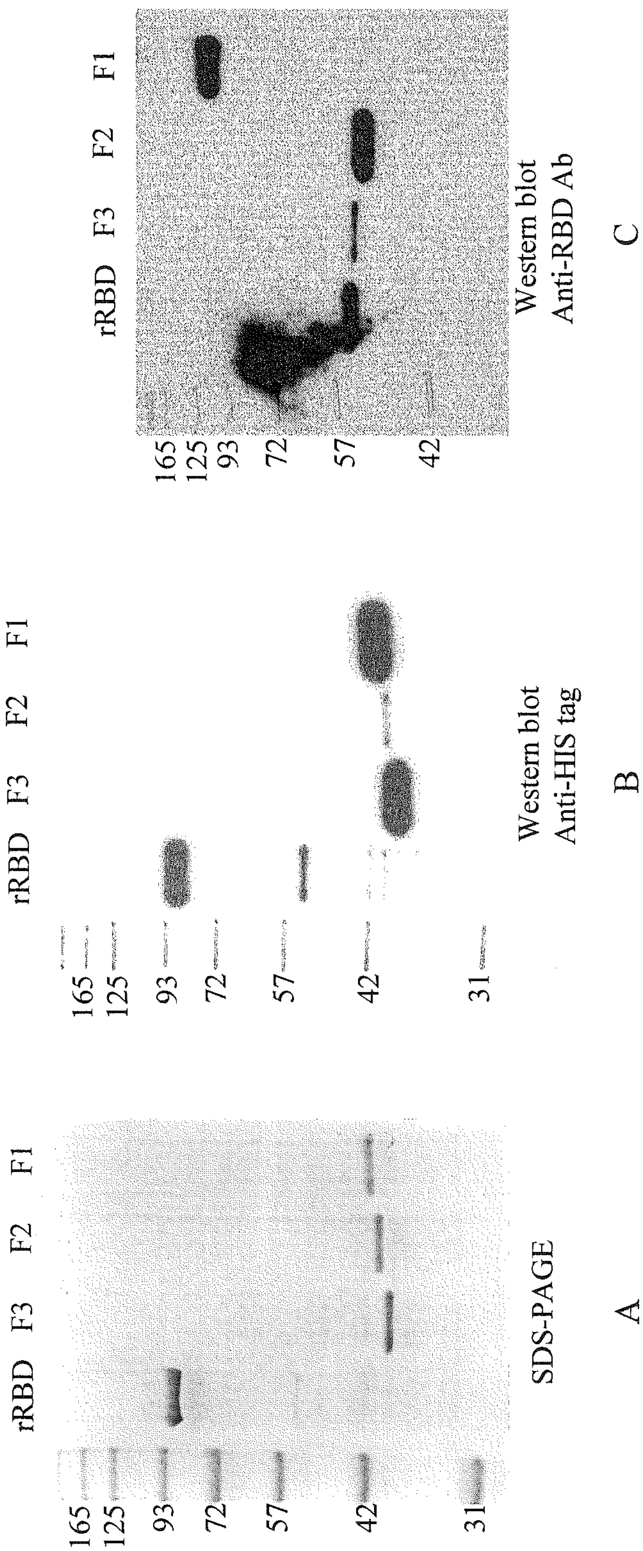
FIG. 4 is a set of SDS-PAGE (Panel A) and Western blot (Panels B and C) showing analysis of recombinant tcdA-RBD fragments (rRBD-F1, -F2 and -F3) purified using Ni-affinity column from *E. coli* lysate. Molecular weight markers are 31 kDa, 42 kDa, 57 kDa, 72 kDa, 93 kDa, 125 kDa).
Figure 5:
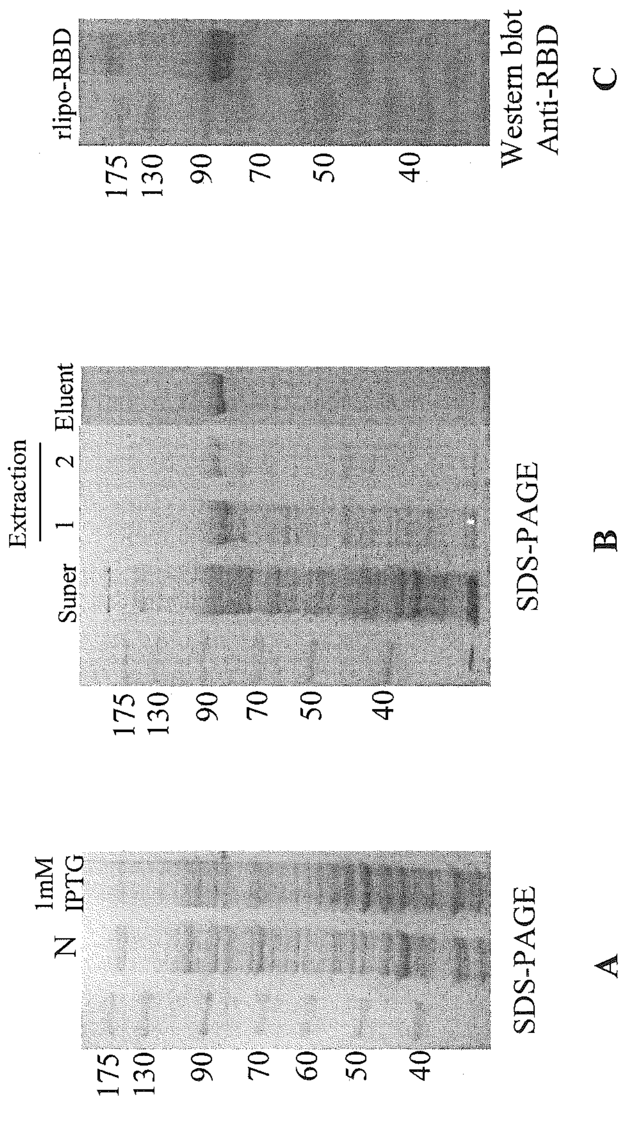
FIG. 5 is a set of SDS-PAGE (Panels A and B) and Western blot (Panel C) showing analysis of recombinant lipidated tcdA-RBD (rlipo-RBD) purified using Ni-affinity column from *E. coli* lysate. Molecular weight markers are 35 kDa, 48 kDa, 63 kDa, 75 kDa, 100 kDa, and 135 kDa.

(2) Expression of rRBD, Rlipo-RBD, and its Fragments in *E. coli* Expression Systems As described above, three truncated proteins (rRBD-F1, -F2 and -F3) and rRBD fused to a C-terminal polyhistidine tag were expressed in *E. coli* BL21 (+) RIL. rlipo-RBD was specifically expressed in *E. coli* C43 (DE3). If necessary, tcdA-RBD and its fragments can be is cloned into CHO cells or baculovirus expression systems as fusion proteins either with Myc-His tag in CHO cells or Vero cells.

rRBD-F1, -F2 and -F3, and rRBD were purified as described above. The LPS contents found in these recombinant antigens were <3 EU/mL, which normally would not have adjuvant effect. The purity of these recombinant antigens were analyzed by SDS-PAGE and Western blot. See FIG. 3 and FIG. 4. This is the first time a full length recombinant tcdA-RBD (911 amino acids) was expressed in *E. coli* and purified with a small amount of LPS contamination.

rlipo-RBD was purified as described above. The purity was also analyzed by SDS-PAGE and Western blot. See FIG. 5. The LPS contents were, <30 EU/mL, which normally would have adjuvant effect.

(3) Guinea Pig Immunogenicity Study of Synthetic Peptides

Groups of 3 guinea pigs were immunized three times with either RBD-P1, -P2, -P3 (see Table 1 above), or a mixture containing all three peptides in equal amounts. One hundred microgram of individual peptide or the mixture was formulated with completed Fruend's adjuvant and injected at day zero, then boosted with half of the amount of peptide or mixture in Incompleted Fruend's adjuvant at days 14 and 56, then bleed out at day 78. Before immunization, guinea pigs were bled from ear vein, and serum samples were collected to determine antigen-specific IgG titer by ELISA, and other biological activities as described above. Pre-bleed sera have no reactivity to peptide and rRBD.

All 3 synthetic peptides individually elicited strong anti-peptide IgG antibody responses. See Table 2 below. These anti-peptide sera also reacted with rRBD and tcdA in ELISA. Also see Table 2 below.

TABLE 2

| | Reactivity of anti-peptide final bleed sera with synthetic peptides (IgG titer x $\log^{10}$) | | | | |
|---|---|---|---|---|---|
| | P1 | P2 | P3 | rRBD | tcdA |
| RBD-P1 | 6.8 | <2 | <2 | 4.6 | 4.2 |
| RBD-P2 | <2 | 6.1 | <2 | 5.1 | 4.6 |
| RBD-P3 | <2 | <2 | 6.1 | 4.2 | 4.1 |
| Mixture | 6.1 | 6.1 | 6.1 | 5.3 | 5.1 |

(4) Mouse Immunogenicity Studies with Different rRBD and Rlipo-RBD Antigens

BALB/c mice were purchased from the National Animal Center in Taiwan and held in the Animal Center of the NHRI. Each group of 6 mice (6-8 weeks old) was immunized with PBS, 30 μg of rRBD, or 3 μg of rlipo-RBD at day zero, 14 and 28, and then challenged with a toxin at day 42. Before immunization, mice were bled from facial vein, and serum was collected to determine antigen-specific IgG and IgA titer by ELISA, and other biological activities as described above.

Figure 6:
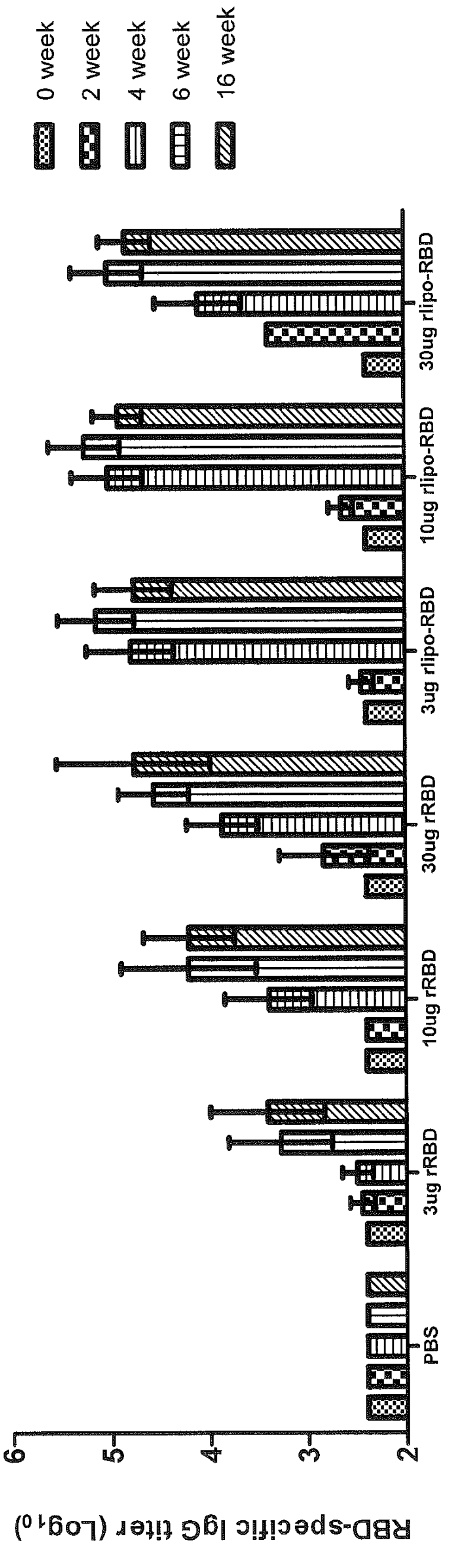
FIG. 6 is a bar graph showing the ELISA results (IgG titer against rRBD) at different time points with antisera obtained from mice immunized with different amounts of rRBD and rlipo-RBD vaccine candidates.

Both rRBD and rlipo-RBD were both highly immunogenic and elicited strong anti-RBD IgG antibodies with titers over 10,000. See FIG. 6. The antibodies reacted with rRBD and tcdA as determined by Western blot analysis (data not shown). A single dose of rlipo-RBD (3 μg) alone was at least ten times more potent than rRBD (30 μg), as shown in Table 3 below. To our surprise only anti-rlipo-RBD mouse sera could significantly inhibit (100%) tcdA toxicity in the Vero cell assay ($p<0.001$). See Table 3. The results indicate that rRBD alone elicited antibody responses, but the antibodies were not totally able to block tcdA binding to Vero cells and killing the cells.

TABLE 3

| | Inhibition titer (>90% inhibition) | |
|---|---|---|
| Immunogen | Pre-immune | Post two immunization |
| PBS | <2 | <2 |
| 30 μg rRBD | <2 | 4 |
| 3 μg rlipo-RBD | <2 | 512 |
| Peptide mixture | <2 | <2 |

When $TCID_{50}$ (50% inhibition) was used as the end point, anti-rRBD mouse sera were found to have significant inhibition against tcdA toxicity in the Vero cell toxicity assay. See Table 4.

TABLE 4

| Immunization | | Toxin A neutralization titer |
|---|---|---|
| PBS | | <4 |
| rRBD | 3 μg (lot 1) | 8 |
| | 10 μg (lot 1) | 64 |
| | 30 μg (lot 1) | 64 |
| | 30 μg (lot 2) | 256 |

(5) Rlipo-RBD Elicited Protective Effect in Mouse tcdA Challenge Model tcdA (toxin A) challenge in a mouse model was performed as described above. Briefly, BALB/c mice were immunized with 30 μg of rRBD or rlipo-RBD three times via intramuscular is injection every two weeks. Toxin A challenge was performed at fifth week via intraperitoneal injection of 150 ng toxin A (NativeAntigen Inc.) and animal mortality was continuously observed every six hours by lab personal. As shown in Table 5 below, 30 μg of either rRBD or rlipo-RBD could protect >90% of mice challenged by Toxin A, while those mice immunized with PBS were killed by Toxin A.

TABLE 5

| | Percent Survival post challenge | | | | |
|---|---|---|---|---|---|
| Immunogen | 0 hr | 15 hr | 24 hr | 48 hr | Day 10 |
| PBS | 6/6 (100%) | 0/6 (0%) | 0/6 (0%) | 0/6 (0%) | 0/6 (0%) |
| 30 μg rRBD | 10/10 (100%) | 7/10 (70%) | 7/10 (70%) | 7/10 (70%) | 7/10 (70%) |
| 30 μg rlipo-RBD | 10/10 (100%) | 10/10 (100%) | 10/10 (100%) | 10/10 (100%) | 10/10 (100%) |

Figure 7:
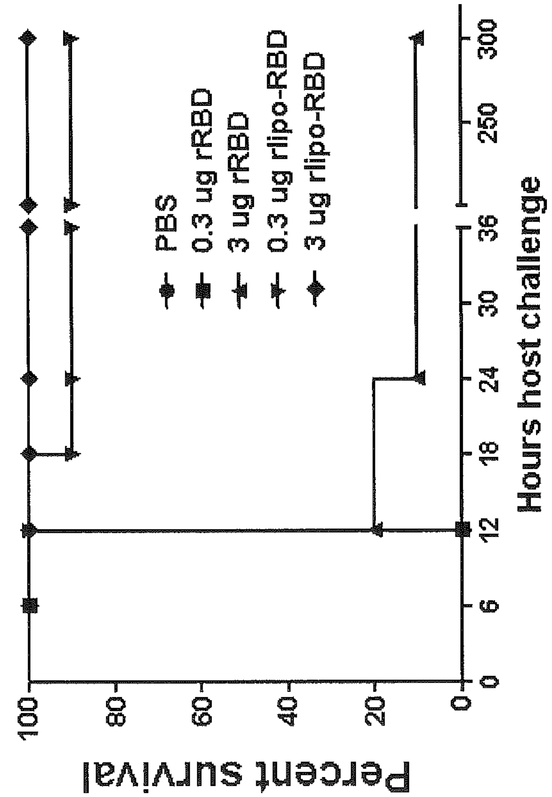
FIG. 7 is a graph showing that rlipo-RBD elicited dose-dependent immune protection against toxicity of tcdA in a mouse challenge model.

Further studies showed that 0.3 μg of rlipo-RBD was sufficient to protect mice from Toxin A toxicity. See FIG. 7 and Table 6. rRBD was less effective; a 3 μg dosage only protected 10% of the mice from Toxin A toxicity. These results were consistent with the results of Vero cell inhibition assay discussed above. Namely, rlipo-RBD elicited strong protective immune responses against Toxin A.

TABLE 6

| Immunization | Percent Survival (%) |
|---|---|
| PBS | 0% |
| 0.3 μg rRBD | 0% |
| 3 μg rRBD | 10% |
| 0.3 μg rlipo-RBD | 90% |
| 3 μg rlipo-RBD | 100% |

Toxin A challenge dosage: 150 ng (5X LD50)

(6) Rlipo-RBD Elicited a Strong Systemic IgA Antibody Response

Figure 8:
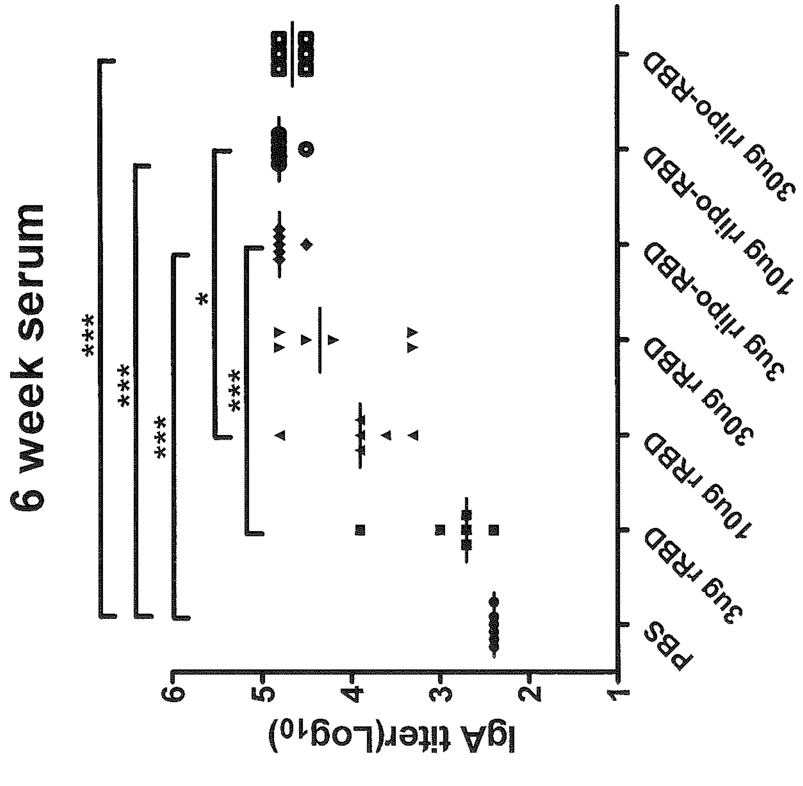
FIG. 8 is a graph showing that rRBD and rlipo-RBD elicited dose-dependent systemic IgA antibody responses and that rlipo-RBD was 10 times more potent than rRBD.

When mouse antisera raised against either rRBD or rlipo-RBD were tested for systemic IgA reactivity against rRBD, we found that 3 μg of rlipo-RBD elicited a strong systemic IgA titer (>10,000) and was as effective as 30 μg of rRBD. See FIG. 8.

Figure 9:
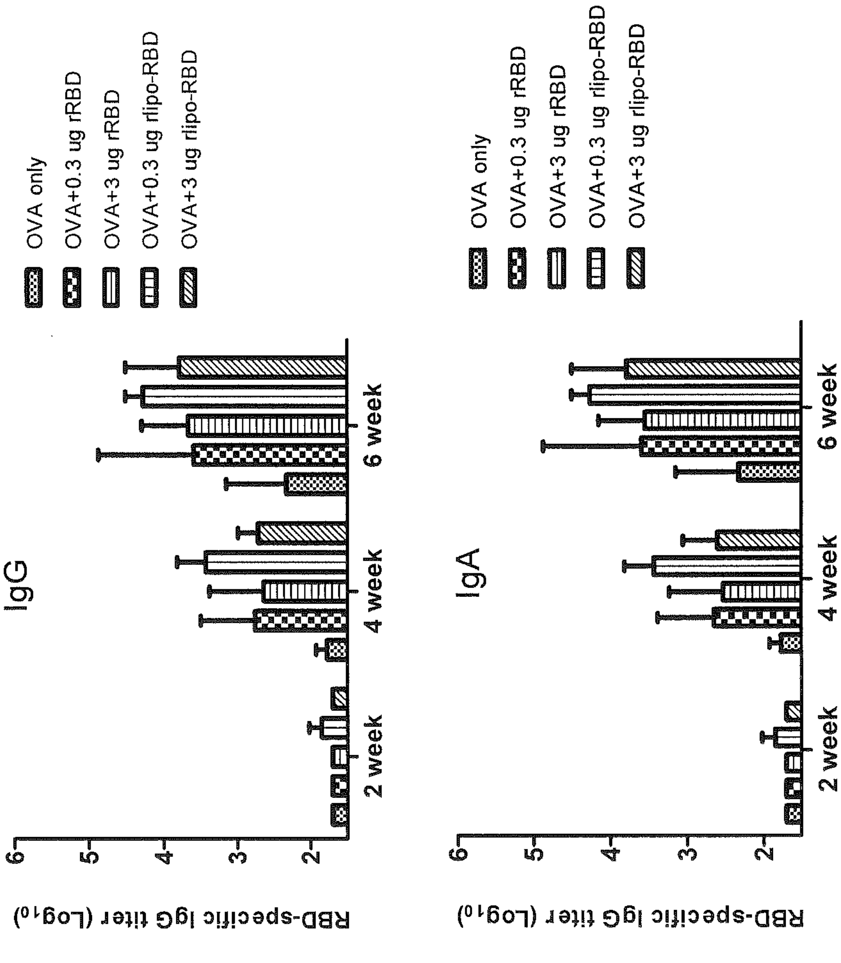
FIG. 9 is a set of bar graphs showing that both rRBD and rlipo-RBD had adjuvant function for enhancing both IgG (top panel) and systemic IgA (lower panel) antibody responses against ovalbulin (OVA) in mouse immunogenicity studies.

(7) rRBD Functioned as an Adjuvant to Enhance Immune Response Against Non-Immunogenic Protein Since rRBD was highly immunogenic at 30 μg dose without an adjuvant, it was of interest to know whether rRBD and/or rlipo-RBD could enhance immune responses against non-immunogenic proteins. Ovalbulin (OVA) is well known as a poor immunogen that could not elicit good IgG antibody responses without an adjuvant. Therefore, different groups of mice were immunized with OVA alone, or with OVA and either rRBD or rlipo-RBD. To our surprise, both rRBD and rlipo-RBD could effectively enhance both IgG and systemic IgA antibody responses against OVA. See FIG. 9. Again, the IgA antibody response at 4 weeks elicited by 2 doses (0.3 μg) of rlipo-RBD was significantly ($p<0.001$) better than those obtained from 3 μg of rRBD. There was not much difference after 3 doses (6 weeks immune responses). See FIG. 9.

Figure 10:
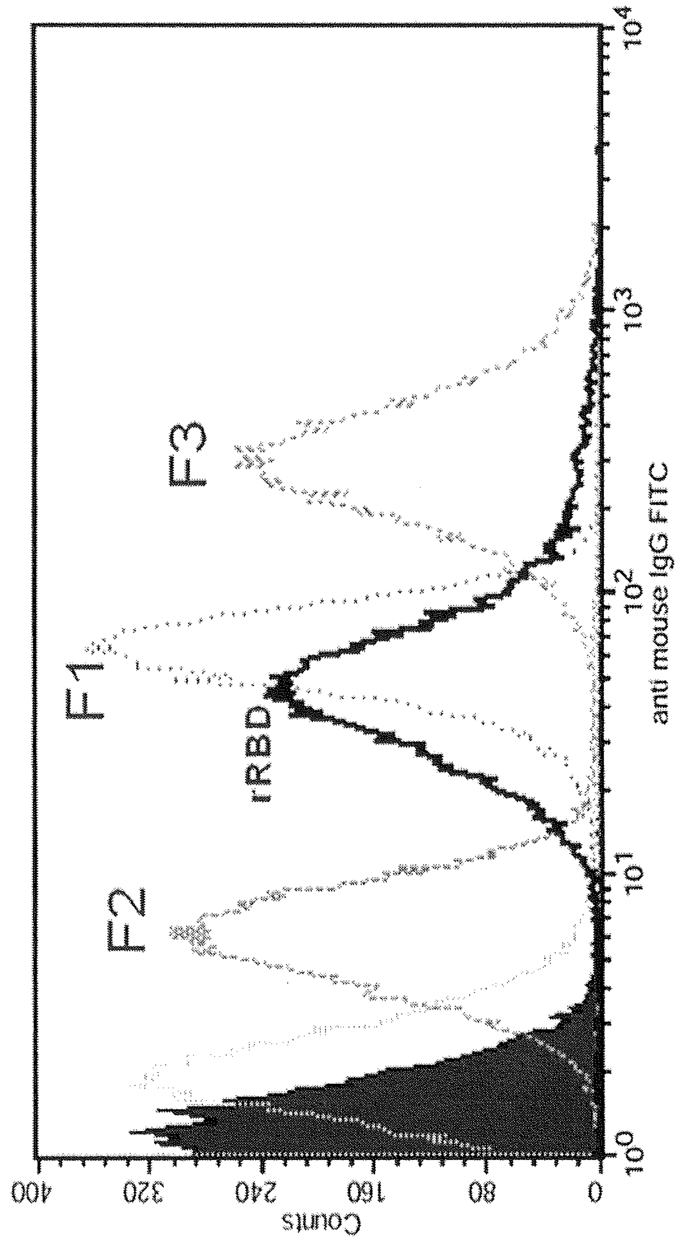
FIG. 10 is a plot showing the identification of the receptor binding activity of rRBD and its fragments (F1, F2 and F3) using a flow cytometric analysis of in vitro VERO cell binding screening assay.
Figure 11:
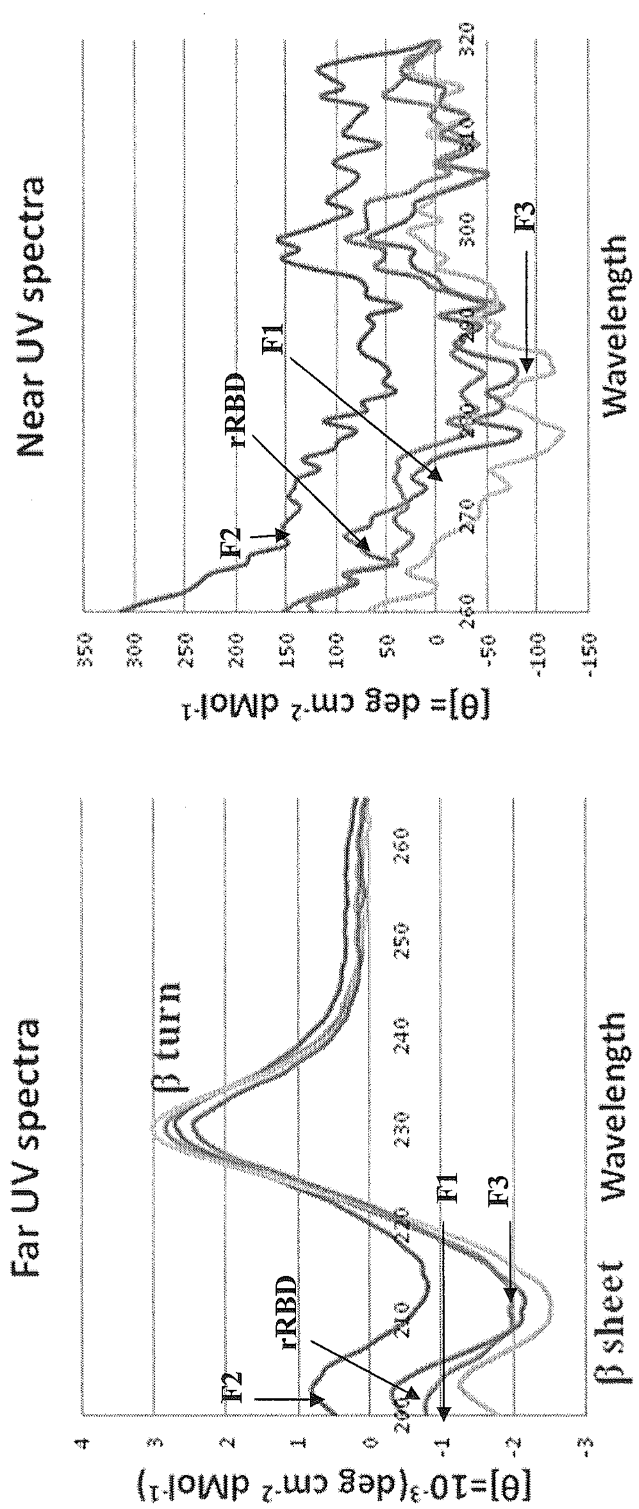
FIG. 11 is a set of plots shows structural analysis of tcdA-rRBD and its truncated fragments using Circular Dichroism (CD) spectroscopy.

(8) Receptor-Binding Fragments of tcdA-RBD rRBD and its fragments (rRBD-F1, -F2 and -F3) were tested for their ability to bind to Vero cells using flow-cytometry assay as described above. As shown in FIG. 10, rRBD-F3 was found to be more potent than rRBD, rRBD-F1, or rRBD-F2 in this binding assay. These results suggest that the repetitive sequences in rRBD-F3 form a higher affinity receptor-binding site than those repetitive sequences in F1 and F2. Circular dichroism (CD) structural analysis showed that significant β-sheet structure can be observed in the F1 and F3 fragments. See FIG. 11. The F2 fragment showed less β-sheet structure signal than the other two fragments.

Figure 12:
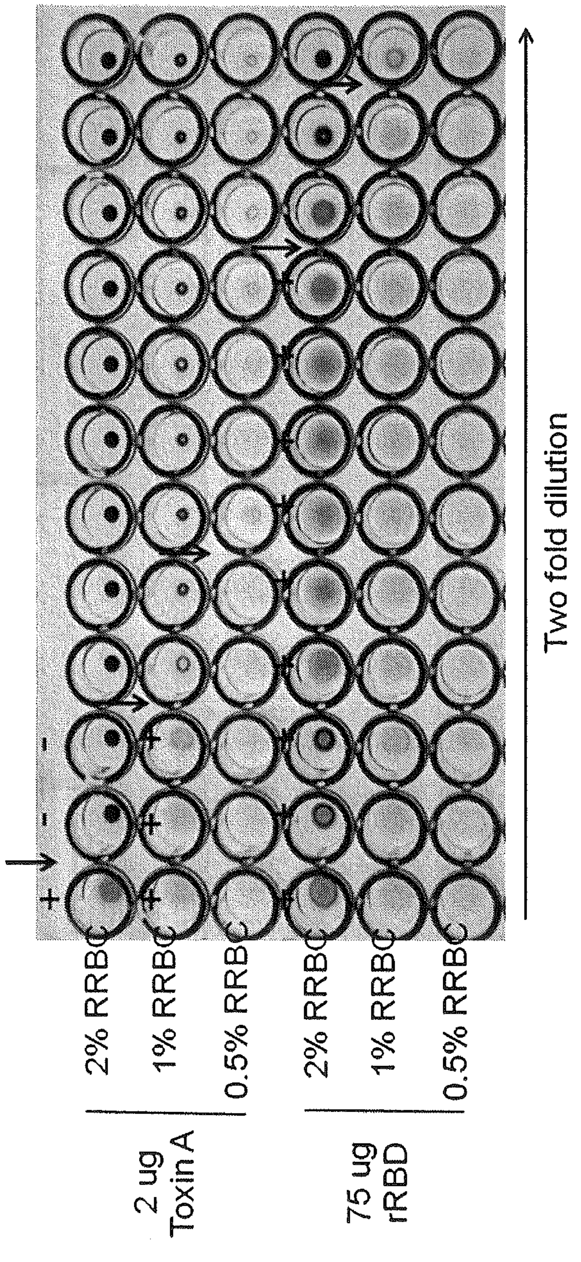
FIG. 12 is an image showing hemagglutinin activity (HA) of tcdA and rRBD in a rabbit red blood cell assay.

(9) Hemaggulutinin Activity (HA) of the Functional Domains of tcdA rRBD and its fragments (rRBD-F1, -F2 and -F3) were tested for HA activity in rabbit red blood cells (RRBC) as described above. At around 1% of RRBC, rRBD was found to be very effective at hemaggulutinating RRBC and was more potent than tcdA. See FIG. 12. The HA activity test indicated that rRBD can easily agglutinate rabbit erythrocyte at 4 pMoles. In addition, anti-rlipo-RBD mouse sera were found to effectively neutralize the HA activity of rRBD in the RRBC assay.

Figure 13:
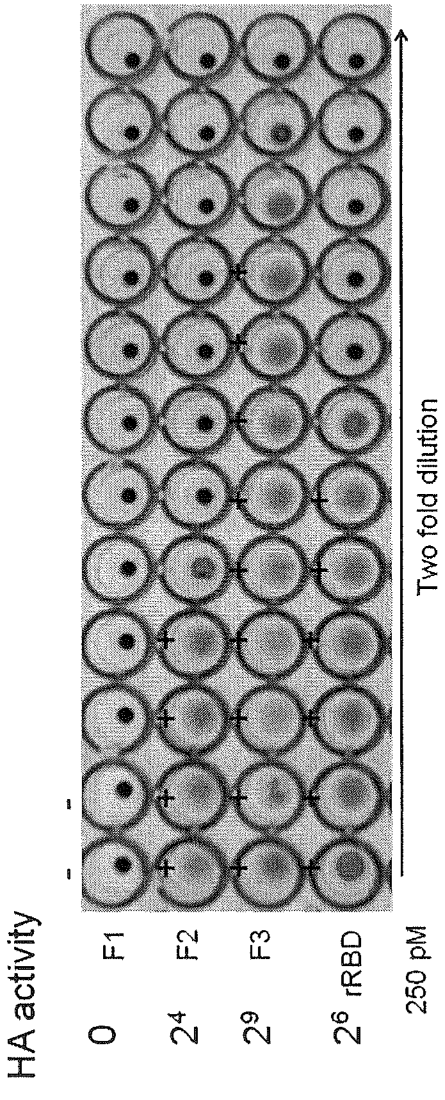
FIG. 13 is an image showing hemagglutinin activity (HA) of rRBD truncated fragment (rRBD-F1, -F2 and -F3) in a rabbit red blood cell assay.
Figure 14:
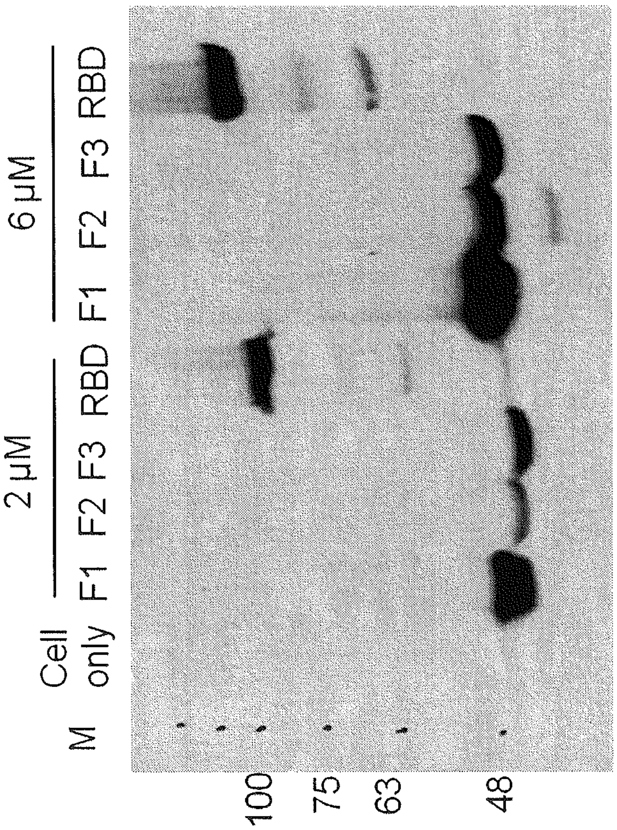
FIG. 14 is a Western blot showing the binding affinity of different RBD fragments for the host receptors.

Further studies showed that rRBD-F3 was more potent than rRBD and rRBD-F2 in the HA assay. See FIG. 13. To our surprise, rRBD-F1 did not show any HA activity in the RRBC assay, but was bound strongly to Vero cells as discussed above. These results suggest that there are other non-carbohydrate binding sites located in the F1 fragment. This observation is further supported by the direct Vero cell binding assay. Western blot analysis showed that RBD-F1 exhibited strong binding to Vero cells, while RBD-F2 exhibited less binding than the other two fragments. See FIG. 14. These results taken together indicate that, the small differences in the repetitive sequences in the RBD fragments can affect their affinity for the host receptor and their hemagglutination activity.

Figure 15:
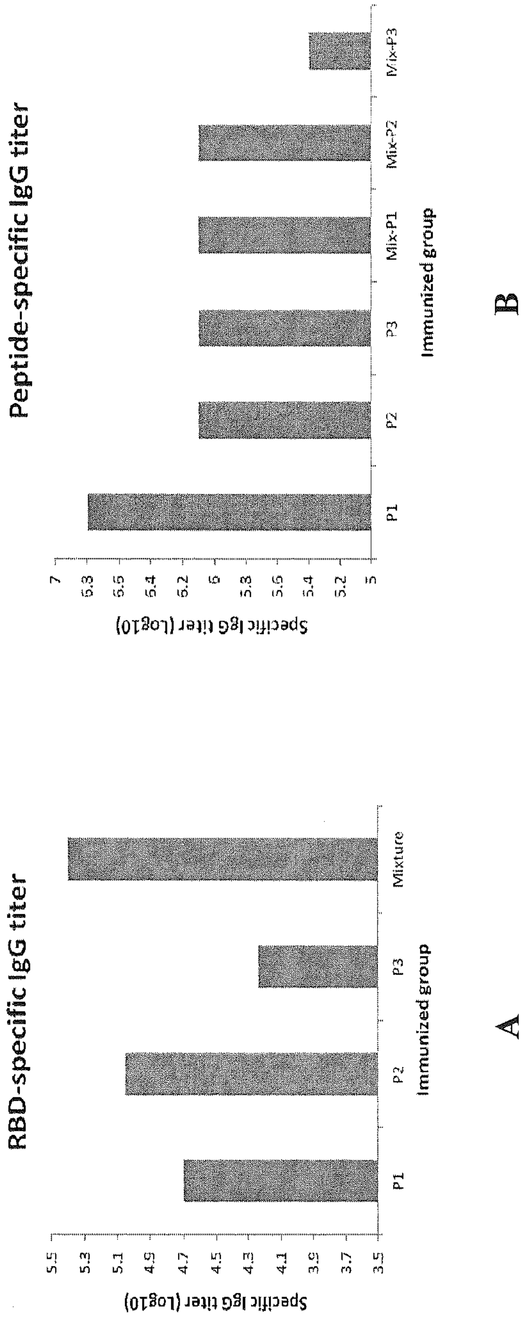
FIG. 15 is a set of bar graphs showing the ELISA results of guinea pig sera raised against different synthetic peptides and their mixture. Panel A shows anti-peptide sera IgG titer against rRBD. Panel B shows anti-peptide sera IgG titer against individual peptides. Mixture includes P1, P2 and P3.
Figure 16:
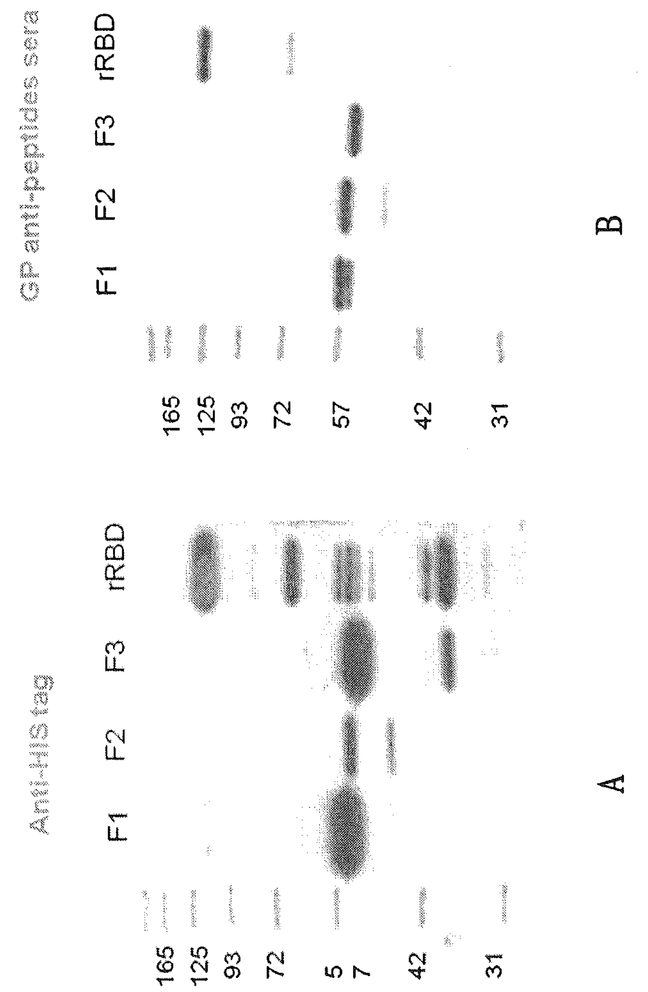
FIG. 16 is a set of Western blots showing analysis of guinea pig antisera raised against a synthetic peptide mixture. Panels (A) and (B) are rRBD and its fragments blot against mouse anti-rRBD sera and guinea pig anti-peptide mixture, respectively.
Figure 17:
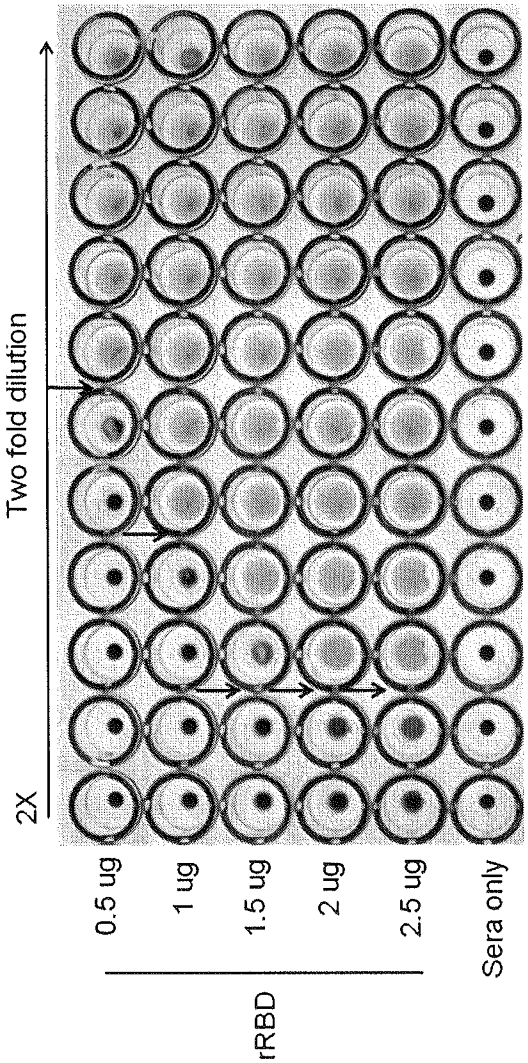
FIG. 17 is an image showing that anti-peptide guinea pig sera inhibited the hemagglutinin activity (HA) of rRBD in a rabbit red blood cell assay.
Figure 18:
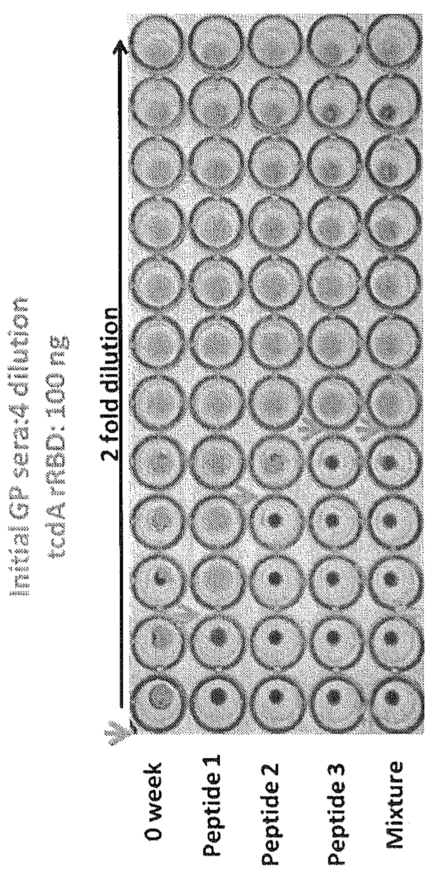
FIG. 18 is an image showing the hemagglutinin inhibition (HAI) activity of guinea pig antisera generated from immunization with individual RBD fragments.

(10) Guinea Pig Anti-Peptide Antibodies Inhibited the HA Activity of rRBD in RRBC Assay Synthetic peptides RBD-P1, -P2, and -P3 elicited anti-rRBD antibody responses in guinea pig immunogenicity studies as described above. See FIG. 15 and FIG. 16. We tested whether these anti-peptide sera could inhibit the HA activity of rRBD in a RRBC assay. As shown in FIG. 17, these sera were effective at inhibiting the HA activity of rRBD in the RRBC assay. The potency of guinea pig anti-peptide sera against the HA of RBD is shown in FIG. 18.

(11) rRBD and its Fragments can Function as Carriers for Drug Delivery

Figure 19:
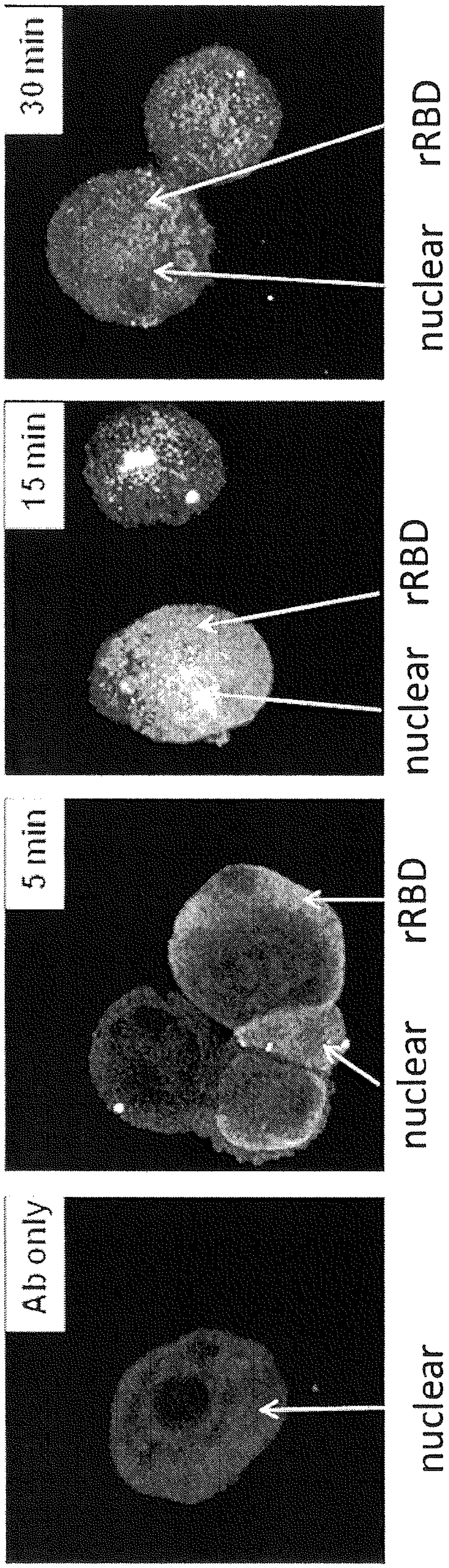
FIG. 19 is a set of confocal microscopy images showing that tcdA-RBD and its fragment can quickly bind to the host receptor within a minute, and then internalize and delocalize inside the cell within 10 minutes and start to be degraded in 30 minutes.

As shown by the FACS analysis and Vero cell direct binding assay described above, rRBD and its fragments can quickly recognize and bind to the host receptor(s). Using confocal microscopy, we observed that rRBD and its fragments quickly bound to the host receptor within a minute. They were then internalized and delocalized inside the cell within 10 minutes and started to be degraded within 30 minutes. See FIG. 19. These results suggest that rRBD and its fragments can function as carriers for drug delivery.

(12) Comparison of Immunogenicity of rRBD and its Fragments

Figure 20:
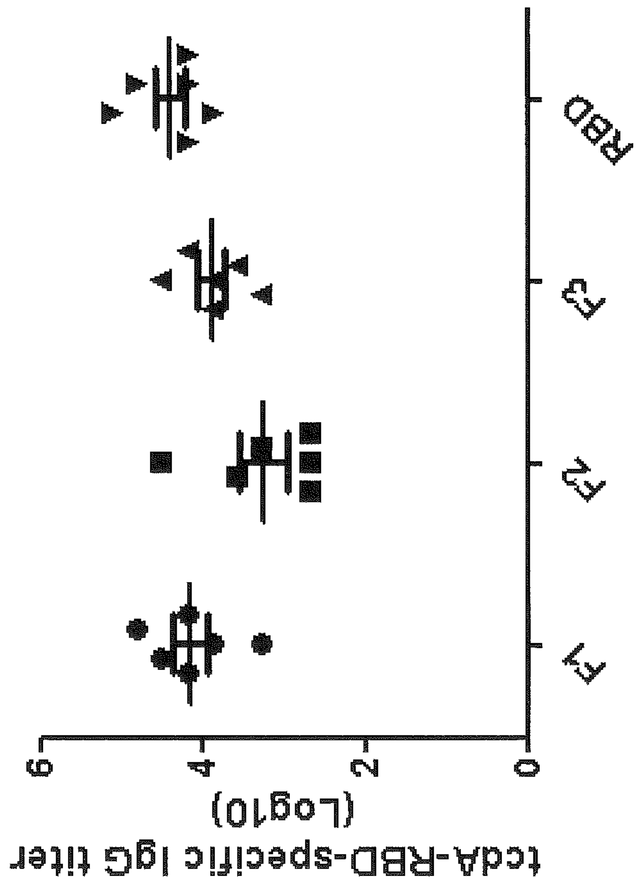
FIG. 20 is a plot showing the biological and immunological functions of antisera generated from mice immunized with RBD fragments.

RBD-F1, -F2 and -F3 were designed to have the same number of repetitive sequences derived from the N-terminus, middle region and the C-terminus of RBD, respectively, but each fragment had different level of functions and biophysical characterization as described above. We assess their immunogenicity and the immunological properties of the elicited antibodies. Mouse immunogenicity study was performed with individual RBD fragment at 30 μg dose. RBD-F1 and -F3 fragments were found to be as potent as rRBD in the mouse immunogenicity studies. See FIG. 20. RBD-F2 was less immunogenic as compared to the other RBD fragments ($p<0.05$). Although RBD fragments could elicit good IgG antibody responses, the biological function of these antibodies as determined by the Toxin A neutralization assay ($TCID_{50}$) was found to be less effective than that of anti-rRBD antibodies. See Table 7. The best titer obtained from anti-RBD-F3 sera was 16, whereas the titer of 256 was obtained from anti-rRBD antibodies. Nevertheless, these results suggest that RBD fragments can be used individually or in combination as vaccine candidates against Cd infection.

TABLE 7

| Immunization | Toxin A neutralization titer ($TCID_{50}$) |
|---|---|
| F1 | 8 |
| F2 | 4 |
| F3 | 16 |
| rRBD | 256 |

Figure 21:
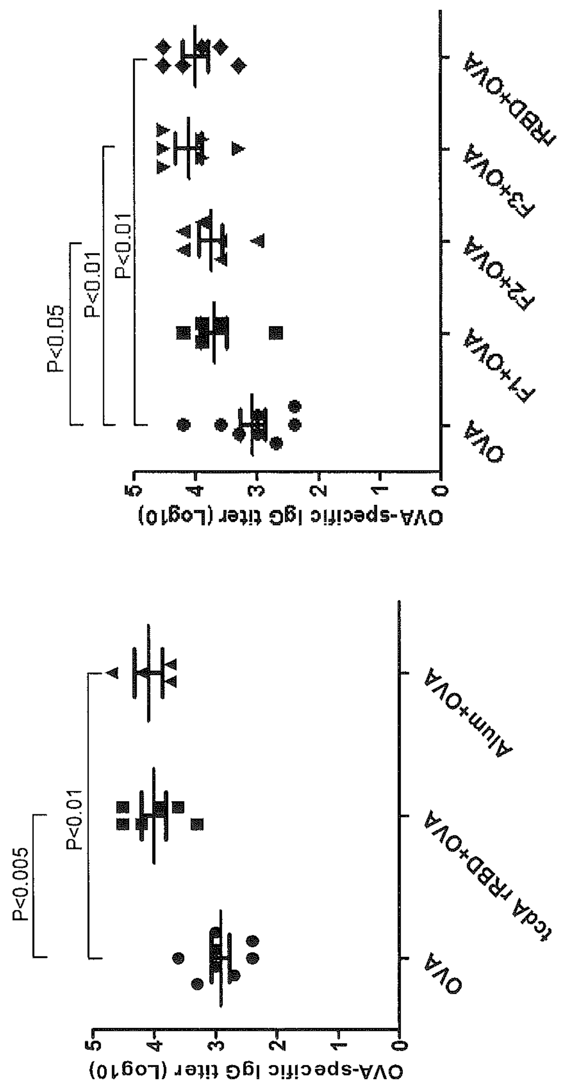
FIG. 21 is a set of plots showing the adjuvant activities of rRBD and its truncated fragments.

(13) RBD Fragments can Act as Immuno-Stimulators to Enhance Immune Responses Against Poor Immunogenic Antigen We tested whether the RBD fragments could enhance immune responses against non-immunogenic proteins. OVA was again used as model protein for this study. Different groups of mice (6 in each group) were immunized with OVA alone (10 μg), or with OVA formulated either with alum, rRBD (10 μg), or different RBD fragment (30 μg each). Interestingly, RBD and its fragments could effectively increase IgG antibody responses against OVA. See FIG. 21. We also tested the adjuvant effect of each RDB fragment at 10 μg dose. These results indicate that all RBD fragments can function as adjuvants to enhance the immune responses against poorly immunogenic antigens.

Figure 22:
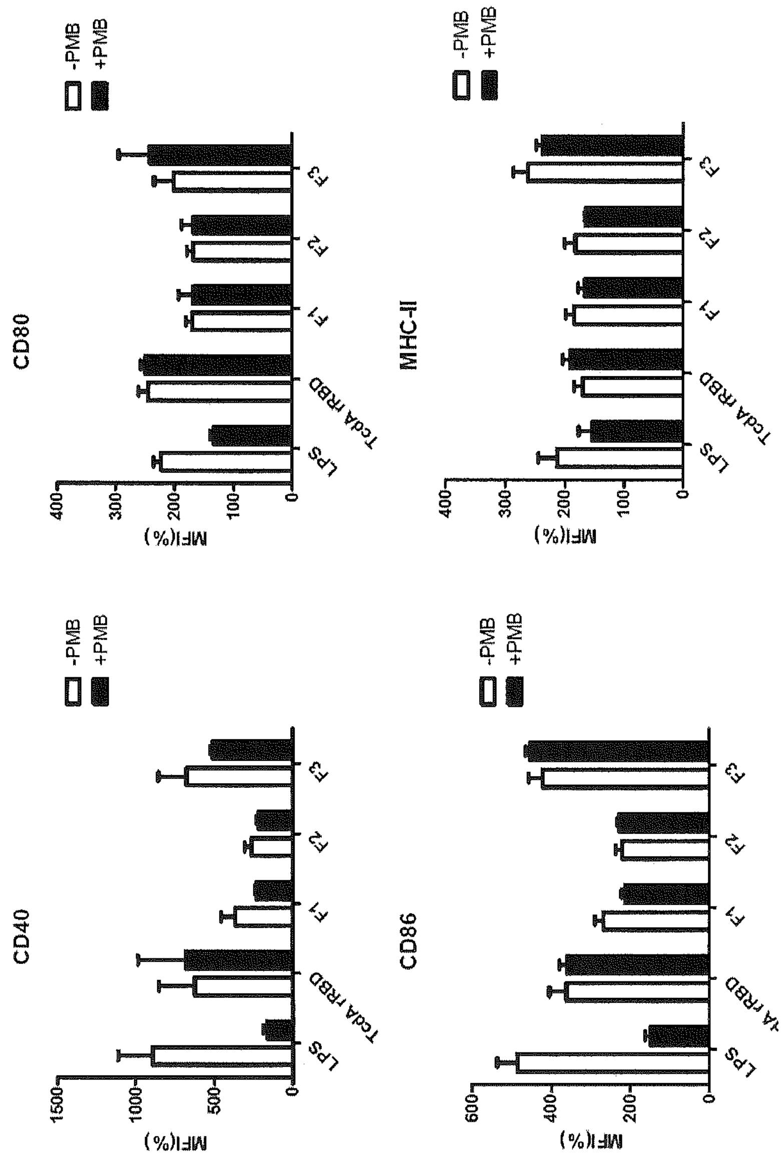
FIG. 22 is a set of graphs showing that rRBD and its fragments up-regulated T-cell effector biomarkers in a dendritic cell activation study.
Figure 23:
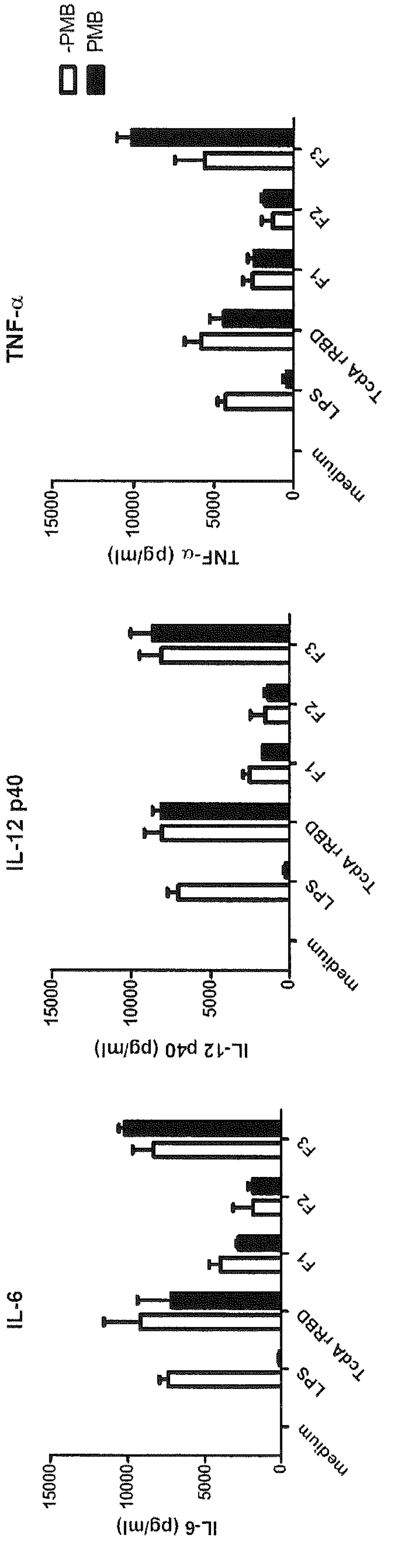
FIG. 23 is a set of graphs showing that rRBD and its fragments up-regulated pro-inflammatory cytokines in a dendritic cell activation study.

(14) Dendritic Cell Maturation could be Triggered Either by rRBD or RBD Fragments Cd toxin A has been reported to up-regulate surface effect molecules and expression of chemokine CXCL2 of dendritic cells (DCs). We tested whether rRBD and its fragments could promote maturation of DCs, which are important antigen-presenting cells that modulate the immune system. After BMDCs from C57BL/6 were treated with rRBD, DC maturation markers (CD40, CD80, CD86, and MHC-II) correlated with T-cell activity and proinflammatory cytokines (IL-6, IL-12, and TNF-α) were analyzed. Indeed, significantly up-regulation of surface T-cell effector molecules and high level of pro-inflammatory cytokines (IL-6, IL-12, and TNF-α) from culture medium could be detected after rRBD treatment. See FIG. 22 and FIG. 23.

In order to preclude LPS contamination, LPS in the rRBD solution was limited to 0.03 EU/μg. Additionally, every test received polymyxin B to neutralize LPS function to rule out DC activation by LPS through the Toll-like receptor 4 pathway.

The results also demonstrated that there were no significant differences between polymyxin B-treated and non-treated rRBD. In addition, we also boiled both rRBD solution and LPS to denature and destroy biological functions of rRBD. DC activity was not significantly affected in the LPS only treatment, but impeded to the same extend as the medium control in boiled rRBD. Overall, these data clearly demonstrate that the observed DC activity was is attributed to rRBD.

The DC activation studies were also performed with individual RBD fragments. The results were found to be similar to those obtained with rRBD. See FIG. 22 and FIG. 23. RBD-F3 was found to be the most potent as compared with the other fragments.

Taking these results together, we conclude that the activation of DCs at the immunization site could contribute to the immunological potency of rRBD and its truncated fragments.

(15) Immunogenic Peptides Identified from Other Regions of tcdA

To prepare an effective diagnostic kit for detecting Cd infection and diseases associated with it, polypeptides (CdTx-CP, CdTx-GT1, CdTx-GT2, CdTx-GT3, CdTx-TM1, CdTx-TM2, and CdTx-TM3) including other functional domains of tcdA (see Table 1 above) were synthesized and tested in guinea pigs to determine whether these peptides can elicit antibody responses recognizing tcdA from patient samples. As shown in Table 8, the peptide mixture from each region (GT, CP and TM) was found to induce regional specific anti-peptide antibody responses with titer >10,000. These antisera were found to specifically react with tcdA and not RBD in a Western blot analysis. The results showed that these peptides have the capability to elicit antibody responses that recognize tcdA from patient samples, and can be used to effectively diagnose Cd infection and diseases caused by the infection.

TABLE 8

| | | Guinea pig anti-peptide ELISA Titer | | | | | |
|---|---|---|---|---|---|---|---|
| | | GT-mixture | | CP | | TM-mixture | |
| | | 1 | 2 | 1 | 2 | 1 | 2 |
| Coating | GT-1 | 4.41 | 4.41 | 2.60 | 2.60 | 2.60 | 2.60 |
| | GT-2 | 3.81 | 3.81 | 2.60 | 2.60 | 2.60 | 2.60 |
| | GT-3 | 5.01 | 5.61 | 2.60 | 2.60 | 2.60 | 2.60 |
| | CP | 3.20 | 3.20 | 5.01 | 5.01 | 3.20 | 3.20 |
| | TM-1 | 2.60 | 2.60 | 2.60 | 2.60 | 5.61 | 5.01 |
| | TM-2 | 2.60 | 2.60 | 2.60 | 2.60 | 5.01 | 5.01 |
| | TM-3 | 2.60 | 2.60 | 2.60 | 2.60 | 5.61 | 5.61 |
| | tcdA-rRBD | 2.60 | 3.20 | 3.20 | 3.20 | 2.60 | 2.60 |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the embodiments described herein, and without departing from the spirit and scope thereof, can make various changes and modifications of the described embodiments to adapt them to various usages and conditions. Thus, other embodiments are also within the claims.

What is claimed is:

1. An isolated polypeptide comprising the amino acid sequence of SEQ ID NO:2 or 4, and an N-terminal lipidating sequence that includes the amino acid sequence of SEQ ID NO:20.

2. The isolated polypeptide of claim 1, wherein the polypeptide includes the amino acid sequence of SEQ ID NO:24 or 28.

3. The polypeptide of claim 1, wherein the polypeptide has the sequence of SEQ ID NO: 2 and an N-terminal lapidating sequence that includes the amino acid sequence of SEQ ID NO:20.

4. An immunogenic composition comprising the isolated polypeptide of claim 1, and a carrier.

5. The immunogenic composition of claim 4, wherein the carrier is a pharmaceutical acceptable carrier.

6. A method of inducing an immune response in a subject, comprising administering to the subject the immunogenic composition of claim 4.

7. The immunogenic composition of claim 4, wherein the polypeptide has the sequence of SEQ ID NO: 2 and an N-terminal lapidating sequence that includes the amino acid sequence of SEQ ID NO:20.

8. The immunogenic composition of claim 7, further comprising another antigen.

* * * * *